US011160823B2

(12) United States Patent
Jones et al.

(10) Patent No.: US 11,160,823 B2
(45) Date of Patent: Nov. 2, 2021

(54) THERAPEUTIC TARGETS FOR FACIOSCAPULOHUMERAL MUSCULAR DYSTROPHY

(71) Applicant: University of Massachusetts, Boston, MA (US)

(72) Inventors: Peter L. Jones, Carson City, NV (US); Michael R. Green, Boylston, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 16/347,688

(22) PCT Filed: Nov. 7, 2017

(86) PCT No.: PCT/US2017/060410
§ 371 (c)(1),
(2) Date: May 6, 2019

(87) PCT Pub. No.: WO2018/085842
PCT Pub. Date: May 11, 2018

(65) Prior Publication Data
US 2019/0343865 A1 Nov. 14, 2019

Related U.S. Application Data

(60) Provisional application No. 62/490,783, filed on Apr. 27, 2017, provisional application No. 62/418,694, filed on Nov. 7, 2016.

(51) Int. Cl.
| A61K 31/713 | (2006.01) |
| C12N 15/113 | (2010.01) |
| A61K 31/7105 | (2006.01) |
| A61K 45/06 | (2006.01) |
| C12N 15/90 | (2006.01) |

(52) U.S. Cl.
CPC ........ *A61K 31/7105* (2013.01); *A61K 31/713* (2013.01); *A61K 45/06* (2013.01); *C12N 15/113* (2013.01); *C12N 15/90* (2013.01); *C12N 2310/11* (2013.01); *C12N 2310/14* (2013.01); *C12N 2310/20* (2017.05); *C12N 2740/16043* (2013.01)

(58) Field of Classification Search
None
See application file for complete search history.

(56) References Cited

U.S. PATENT DOCUMENTS

| 2015/0087636 | A1 | 3/2015 | Sverdrup | |
| 2019/0298727 | A1 * | 10/2019 | Rickard | A61K 31/52 |
| 2020/0017842 | A1 * | 1/2020 | Jones | C12N 15/11 |

FOREIGN PATENT DOCUMENTS

| WO | WO-2014071340 A1 * | 5/2014 | ......... G01N 33/6893 |
| WO | WO 2014/144169 A1 | 9/2014 | |
| WO | WO 2014/144455 A1 | 9/2014 | |
| WO | WO 2016/044604 A1 | 3/2016 | |
| WO | WO 2016/044641 A2 | 3/2016 | |
| WO | WO 2016/044650 A1 | 3/2016 | |
| WO | WO 2016/115490 A1 | 7/2016 | |
| WO | WO 2016/195493 A1 | 12/2016 | |
| WO | 2017/201585 | 11/2017 | |

OTHER PUBLICATIONS

Lim et al. Human Molecular Genetics 24, Sep. 2015, 4817-4828 (Year: 2015).*
Drew et al. Scientific Reports 7:17993, pp. 1-13 (Year: 2017).*
Partial European Search Report for Application No. EP 17867141.8, dated May 7, 2020.
Balog et al., Increased DUX4 expression during muscle differentiation correlates with decreased SMCHD1 protein levels at D4Z4 [published correction appears in Epigenetics. 2016;11(2):175]. Epigenetics. 2015;10(12):1133-1142. doi:10.1080/15592294.2015.1113798.
Extended European Search Report for Application No. EP 17867141.8, dated Aug. 14, 2020.
Lemmers et al., A unifying genetic model for facioscapulohumeral muscular dystrophy. Science. Sep. 24, 2010;329(5999):1650-3. doi: 10.1126/science.1189044. Epub Aug. 19, 2010. Author Manuscript.
Pang et al., Loss of CARM1 is linked to reduced HuR function in replicative senescence. BMC Mol Biol. Jul. 9, 2013;14:15. doi: 10.1186/1471-2199-14-15.
Rickard et al., Endogenous DUX4 expression in FSHD myotubes is sufficient to cause cell death and disrupts RNA splicing and cell migration pathways. Hum Mol Genet. Oct. 15, 2015;24(20):5901-14. doi: 10.1093/hmg/ddv315. Epub Aug. 5, 2015.
Shishkova et al., Global mapping of CARM1 substrates defines enzyme specificity and substrate recognition. Nat Commun. May 24, 2017;8:15571. doi: 10.1038/ncomms15571.
Wallace et al., DUX4, a candidate gene for facioscapulohumeral muscular dystrophy, causes p53-dependent myopathy in vivo. Ann Neurol. Mar. 2011;69(3):540-52. doi: 10.1002/ana.22275. Epub Dec. 8, 2010. Author Manuscript.
Yao et al., DUX4-induced gene expression is the major molecular signature in FSHD skeletal muscle. Hum Mol Genet. Oct. 15, 2014;23(20):5342-52. doi: 10.1093/hmg/ddu251. Epub May 26, 2014.
Himeda et al., CRISPR/dCas9-mediated Transcriptional Inhibition Ameliorates the Epigenetic Dysregulation at D4Z4 and Represses DUX4-fl in FSH Muscular Dystrophy. Mol Ther. Mar. 2016;24(3):527-35. doi:10.1038/mt.2015.200. Epub Nov. 3, 2015.
Extended European Search Report for Application No. EP 21161592.7, dated Sep. 17, 2021.

(Continued)

Primary Examiner — Brian Whiteman
(74) Attorney, Agent, or Firm — Wolf, Greenfield & Sacks, P.C.

(57) ABSTRACT

The disclosure relates to methods and compositions for regulating expression of DUX4. In some aspects, methods described by the disclosure are useful for treating a disease associated with aberrant DUX4 expression (e.g., facioscapulohumeral muscular dystrophy).

8 Claims, 25 Drawing Sheets

Specification includes a Sequence Listing.

(56) References Cited

OTHER PUBLICATIONS

El Messaoudi et al., Coactivator-associated arginine methyltransferase 1 (CARM1) is a positive regulator of the Cyclin E1 gene. Proc Natl Acad Sci USA. Sep. 5, 2006;103(36): 13351-6. doi: 10.1073/pnas. 0605692103. Epub Aug. 28, 2006.

Feng et al., Biochemical control of CARM1 enzymatic activity by phosphorylation. J Biol Chem. Dec. 25, 2009;284(52):36167-36174. doi: 10.1074/jbc.M109.065524. Epub Oct. 20, 2009.

Frietze et al., CARM1 regulates estrogen-stimulated breast cancer growth through upregulation of E2F1. Cancer Res. Jan. 1, 2008;68(1):301-6. doi: 10.1158/0008-5472.CAN-07-1983.

\* cited by examiner

SEQUENCE LISTING

<160> NUMBER OF SEQ ID NOS: 55

<210> SEQ ID NO 1
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 1
ccgggcctct gacatgcgat ttgaactcga gttcaaatcg catgtcagag gcttttt        57

<210> SEQ ID NO 2
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 2
ccgggcagag agtaatggtg tgttactcga gtaacacacc attactctct gcttttt        57

<210> SEQ ID NO 3
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 3
ccgggcccaa gtcttggtat gctatctcga gatagcatac caagacttgg gcttttt        57

```
<210> SEQ ID NO 4
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 4
ccggcgacat aaacttgaca tctttctcga gaaagatgtc aagtttatgt cgttttt       57

<210> SEQ ID NO 5
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 5
ccggcctgcc aaataccata agaaactcga gtttcttatg gtatttggca ggttttt       57

<210> SEQ ID NO 6
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 6
ccggcgtact ttgtttatcc cagaactcga gttctgggat aaacaaagta cgttttt       57

<210> SEQ ID NO 7
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 7
ccgggttctt taatttacgg gtcttctcga gaagacccgt aaattaaaga acttttt       57

<210> SEQ ID NO 8
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 8
ccggccgggc aaatagattc gagtactcga gtactcgaat ctatttgccc ggttttt       57

<210> SEQ ID NO 9
<211> LENGTH: 58
<212> TYPE: DNA
<213> ORGANISM: Artificial Sequence
<220> FEATURE:
<223> OTHER INFORMATION: Synthetic Polynucleotide

<400> SEQUENCE: 9
ccgggcgatg aagaagaagg tcaaactcga gtttgacctt cttcttcatc gcttttttg    58

<210> SEQ ID NO 10
<211> LENGTH: 57
<212> TYPE: DNA
<213> ORGANISM: Artificial Sequence
<220> FEATURE:
<223> OTHER INFORMATION: Synthetic Polynucleotide
```

```
<400> SEQUENCE: 10 ccggccctttt gctgtgacac ttcttctcga gaagaagtgt cacagcaaag ggttttt        57

<210> SEQ ID NO 11
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 11
ccgggccctc tttacgtgat tcaaactcga gtttgaatca cgtaaagagg gcttttt        57

<210> SEQ ID NO 12
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 12
cgttaccggg gtggagcctc ggaat                                            25

<210> SEQ ID NO 13
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 13
cttgcccgga agcgctggct ggggt                                            25

<210> SEQ ID NO 14
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 14
gccaaagcag ggaaacggga ggggt                                            25

<210> SEQ ID NO 15
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 15
atacaagtta aatcgtaatt ggaat                                            25

<210> SEQ ID NO 16
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 16
ttgactacac gatgggaaaa gggat                                            25
```

-continued

```
<210> SEQ ID NO 17
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 17
aaaaccgtga gacttcactt ggggt                                          25

<210> SEQ ID NO 18
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 18
tgtgtcttct gtgcctgaca ggggt                                          25

<210> SEQ ID NO 19
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 19
gccctcacgc gtaccttcaa cgg                                            23

<210> SEQ ID NO 20
<211> LENGTH: 1082
<212> TYPE: PRT
<213> ORGANISM: Artificial Sequence
<220> FEATURE:
<223> OTHER INFORMATION: Synthetic Polypeptide

<400> SEQUENCE: 20

Met Ala Pro Lys Lys Lys Arg Lys Val Gly Ile His Gly Val Pro Ala
1               5                   10                  15

Ala Lys Arg Asn Tyr Ile Leu Gly Leu Asp Ile Gly Ile Thr Ser Val
            20                  25                  30

Gly Tyr Gly Ile Ile Asp Tyr Glu Thr Arg Asp Val Ile Asp Ala Gly
        35                  40                  45

Val Arg Leu Phe Lys Glu Ala Asn Val Glu Asn Asn Glu Gly Arg Arg
    50                  55                  60

Ser Lys Arg Gly Ala Arg Arg Leu Lys Arg Arg Arg Arg His Arg Ile
65                  70                  75                  80

Gln Arg Val Lys Lys Leu Leu Phe Asp Tyr Asn Leu Leu Thr Asp His
                85                  90                  95

Ser Glu Leu Ser Gly Ile Asn Pro Tyr Glu Ala Arg Val Lys Gly Leu
            100                 105                 110

Ser Gln Lys Leu Ser Glu Glu Phe Ser Ala Ala Leu Leu His Leu
        115                 120                 125

Ala Lys Arg Arg Gly Val His Asn Val Asn Glu Val Glu Glu Asp Thr
    130                 135                 140

Gly Asn Glu Leu Ser Thr Lys Glu Gln Ile Ser Arg Asn Ser Lys Ala
145                 150                 155                 160

Leu Glu Glu Lys Tyr Val Ala Glu Leu Gln Leu Glu Arg Leu Lys Lys
                165                 170                 175
```

```
Asp Gly Glu Val Arg Gly Ser Ile Asn Arg Phe Lys Thr Ser Asp Tyr
            180                 185                 190

Val Lys Glu Ala Lys Gln Leu Leu Lys Val Gln Lys Ala Tyr His Gln
        195                 200                 205

Leu Asp Gln Ser Phe Ile Asp Thr Tyr Ile Asp Leu Leu Glu Thr Arg
        210                 215                 220

Arg Thr Tyr Tyr Glu Gly Pro Gly Glu Gly Ser Pro Phe Gly Trp Lys
225                 230                 235                 240

Asp Ile Lys Glu Trp Tyr Glu Met Leu Met Gly His Cys Thr Tyr Phe
                245                 250                 255

Pro Glu Glu Leu Arg Ser Val Lys Tyr Ala Tyr Asn Ala Asp Leu Tyr
            260                 265                 270

Asn Ala Leu Asn Asp Leu Asn Asn Leu Val Ile Thr Arg Asp Glu Asn
        275                 280                 285

Glu Lys Leu Glu Tyr Tyr Glu Lys Phe Gln Ile Ile Glu Asn Val Phe
        290                 295                 300

Lys Gln Lys Lys Lys Pro Thr Leu Lys Gln Ile Ala Lys Glu Ile Leu
305                 310                 315                 320

Val Asn Glu Glu Asp Ile Lys Gly Tyr Arg Val Thr Ser Thr Gly Lys
                325                 330                 335

Pro Glu Phe Thr Asn Leu Lys Val Tyr His Asp Ile Lys Asp Ile Thr
            340                 345                 350

Ala Arg Lys Glu Ile Ile Glu Asn Ala Glu Leu Leu Asp Gln Ile Ala
        355                 360                 365

Lys Ile Leu Thr Ile Tyr Gln Ser Ser Glu Asp Ile Gln Glu Glu Leu
        370                 375                 380

Thr Asn Leu Asn Ser Glu Leu Thr Gln Glu Glu Ile Glu Gln Ile Ser
385                 390                 395                 400

Asn Leu Lys Gly Tyr Thr Gly Thr His Asn Leu Ser Leu Lys Ala Ile
                405                 410                 415

Asn Leu Ile Leu Asp Glu Leu Trp His Thr Asn Asp Asn Gln Ile Ala
            420                 425                 430

Ile Phe Asn Arg Leu Lys Leu Val Pro Lys Lys Val Asp Leu Ser Gln
        435                 440                 445

Gln Lys Glu Ile Pro Thr Thr Leu Val Asp Asp Phe Ile Leu Ser Pro
        450                 455                 460

Val Val Lys Arg Ser Phe Ile Gln Ser Ile Lys Val Ile Asn Ala Ile
465                 470                 475                 480

Ile Lys Lys Tyr Gly Leu Pro Asn Asp Ile Ile Ile Glu Leu Ala Arg
                485                 490                 495

Glu Lys Asn Ser Lys Asp Ala Gln Lys Met Ile Asn Glu Met Gln Lys
            500                 505                 510

Arg Asn Arg Gln Thr Asn Glu Arg Ile Glu Glu Ile Ile Arg Thr Thr
        515                 520                 525

Gly Lys Glu Asn Ala Lys Tyr Leu Ile Glu Lys Ile Lys Leu His Asp
        530                 535                 540

Met Gln Glu Gly Lys Cys Leu Tyr Ser Leu Glu Ala Ile Pro Leu Glu
545                 550                 555                 560

Asp Leu Leu Asn Asn Pro Phe Asn Tyr Glu Val Asp His Ile Ile Pro
                565                 570                 575

Arg Ser Val Ser Phe Asp Asn Ser Phe Asn Asn Lys Val Leu Val Lys
            580                 585                 590
```

-continued

Gln Glu Glu Asn Ser Lys Lys Gly Asn Arg Thr Pro Phe Gln Tyr Leu
            595                 600                 605

Ser Ser Ser Asp Ser Lys Ile Ser Tyr Glu Thr Phe Lys Lys His Ile
610                 615                 620

Leu Asn Leu Ala Lys Gly Lys Gly Arg Ile Ser Lys Thr Lys Lys Glu
625                 630                 635                 640

Tyr Leu Leu Glu Glu Arg Asp Ile Asn Arg Phe Ser Val Gln Lys Asp
                645                 650                 655

Phe Ile Asn Arg Asn Leu Val Asp Thr Arg Tyr Ala Thr Arg Gly Leu
            660                 665                 670

Met Asn Leu Leu Arg Ser Tyr Phe Arg Val Asn Asn Leu Asp Val Lys
        675                 680                 685

Val Lys Ser Ile Asn Gly Gly Phe Thr Ser Phe Leu Arg Arg Lys Trp
690                 695                 700

Lys Phe Lys Lys Glu Arg Asn Lys Gly Tyr Lys His His Ala Glu Asp
705                 710                 715                 720

Ala Leu Ile Ile Ala Asn Ala Asp Phe Ile Phe Lys Glu Trp Lys Lys
                725                 730                 735

Leu Asp Lys Ala Lys Lys Val Met Glu Asn Gln Met Phe Glu Glu Lys
            740                 745                 750

Gln Ala Glu Ser Met Pro Glu Ile Glu Thr Glu Gln Glu Tyr Lys Glu
        755                 760                 765

Ile Phe Ile Thr Pro His Gln Ile Lys His Ile Lys Asp Phe Lys Asp
770                 775                 780

Tyr Lys Tyr Ser His Arg Val Asp Lys Lys Pro Asn Arg Glu Leu Ile
785                 790                 795                 800

Asn Asp Thr Leu Tyr Ser Thr Arg Lys Asp Asp Lys Gly Asn Thr Leu
                805                 810                 815

Ile Val Asn Asn Leu Asn Gly Leu Tyr Asp Lys Asp Asn Asp Lys Leu
            820                 825                 830

Lys Lys Leu Ile Asn Lys Ser Pro Glu Lys Leu Leu Met Tyr His His
        835                 840                 845

Asp Pro Gln Thr Tyr Gln Lys Leu Lys Leu Ile Met Glu Gln Tyr Gly
850                 855                 860

Asp Glu Lys Asn Pro Leu Tyr Lys Tyr Glu Glu Thr Gly Asn Tyr
865                 870                 875                 880

Leu Thr Lys Tyr Ser Lys Lys Asp Asn Gly Pro Val Ile Lys Lys Ile
                885                 890                 895

Lys Tyr Tyr Gly Asn Lys Leu Asn Ala His Leu Asp Ile Thr Asp Asp
            900                 905                 910

Tyr Pro Asn Ser Arg Asn Lys Val Val Lys Leu Ser Leu Lys Pro Tyr
        915                 920                 925

Arg Phe Asp Val Tyr Leu Asp Asn Gly Val Tyr Lys Phe Val Thr Val
930                 935                 940

Lys Asn Leu Asp Val Ile Lys Lys Glu Asn Tyr Tyr Glu Val Asn Ser
945                 950                 955                 960

Lys Cys Tyr Glu Glu Ala Lys Lys Leu Lys Lys Ile Ser Asn Gln Ala
                965                 970                 975

Glu Phe Ile Ala Ser Phe Tyr Asn Asn Asp Leu Ile Lys Ile Asn Gly
            980                 985                 990

Glu Leu Tyr Arg Val Ile Gly Val Asn Asn Asp Leu Leu Asn Arg Ile
        995                 1000                1005

```
Glu Val Asn Met Ile Asp Ile Thr Tyr Arg Glu Tyr Leu Glu Asn
    1010                1015                1020

Met Asn Asp Lys Arg Pro Pro Arg Ile Ile Lys Thr Ile Ala Ser
    1025                1030                1035

Lys Thr Gln Ser Ile Lys Lys Tyr Ser Thr Asp Ile Leu Gly Asn
    1040                1045                1050

Leu Tyr Glu Val Lys Ser Lys His Pro Gln Ile Ile Lys Lys
    1055                1060                1065

Gly Lys Arg Pro Ala Ala Thr Lys Lys Ala Gly Gln Ala Lys
    1070                1075                1080

<210> SEQ ID NO 21
<211> LENGTH: 1158
<212> TYPE: PRT
<213> ORGANISM: Artificial Sequence
<220> FEATURE:
<223> OTHER INFORMATION: Synthetic Polypeptide

<400> SEQUENCE: 21

Met Ala Pro Lys Lys Lys Arg Lys Val Gly Ile His Gly Val Pro Ala
1               5                   10                  15

Ala Lys Arg Asn Tyr Ile Leu Gly Leu Ala Ile Gly Ile Thr Ser Val
            20                  25                  30

Gly Tyr Gly Ile Ile Asp Tyr Glu Thr Arg Asp Val Ile Asp Ala Gly
        35                  40                  45

Val Arg Leu Phe Lys Glu Ala Asn Val Glu Asn Asn Glu Gly Arg Arg
    50                  55                  60

Ser Lys Arg Gly Ala Arg Arg Leu Lys Arg Arg Arg Arg His Arg Ile
65                  70                  75                  80

Gln Arg Val Lys Lys Leu Leu Phe Asp Tyr Asn Leu Leu Thr Asp His
                85                  90                  95

Ser Glu Leu Ser Gly Ile Asn Pro Tyr Glu Ala Arg Val Lys Gly Leu
            100                 105                 110

Ser Gln Lys Leu Ser Glu Glu Phe Ser Ala Ala Leu Leu His Leu
        115                 120                 125

Ala Lys Arg Arg Gly Val His Asn Val Asn Glu Val Glu Glu Asp Thr
    130                 135                 140

Gly Asn Glu Leu Ser Thr Lys Glu Gln Ile Ser Arg Asn Ser Lys Ala
145                 150                 155                 160

Leu Glu Glu Lys Tyr Val Ala Glu Leu Gln Leu Glu Arg Leu Lys Lys
                165                 170                 175

Asp Gly Glu Val Arg Gly Ser Ile Asn Arg Phe Lys Thr Ser Asp Tyr
            180                 185                 190

Val Lys Glu Ala Lys Gln Leu Leu Lys Val Gln Lys Ala Tyr His Gln
        195                 200                 205

Leu Asp Gln Ser Phe Ile Asp Thr Tyr Ile Asp Leu Leu Glu Thr Arg
    210                 215                 220

Arg Thr Tyr Tyr Glu Gly Pro Gly Glu Gly Ser Pro Phe Gly Trp Lys
225                 230                 235                 240

Asp Ile Lys Glu Trp Tyr Glu Met Leu Met Gly His Cys Thr Tyr Phe
                245                 250                 255

Pro Glu Glu Leu Arg Ser Val Lys Tyr Ala Tyr Asn Ala Asp Leu Tyr
            260                 265                 270

Asn Ala Leu Asn Asp Leu Asn Asn Leu Val Ile Thr Arg Asp Glu Asn
        275                 280                 285
```

-continued

```
Glu Lys Leu Glu Tyr Tyr Glu Lys Phe Gln Ile Ile Glu Asn Val Phe
290                 295                 300

Lys Gln Lys Lys Lys Pro Thr Leu Lys Gln Ile Ala Lys Glu Ile Leu
305                 310                 315                 320

Val Asn Glu Glu Asp Ile Lys Gly Tyr Arg Val Thr Ser Thr Gly Lys
                325                 330                 335

Pro Glu Phe Thr Asn Leu Lys Val Tyr His Asp Ile Lys Asp Ile Thr
            340                 345                 350

Ala Arg Lys Glu Ile Ile Glu Asn Ala Glu Leu Leu Asp Gln Ile Ala
        355                 360                 365

Lys Ile Leu Thr Ile Tyr Gln Ser Ser Glu Asp Ile Gln Glu Glu Leu
370                 375                 380

Thr Asn Leu Asn Ser Glu Leu Thr Gln Glu Glu Ile Glu Gln Ile Ser
385                 390                 395                 400

Asn Leu Lys Gly Tyr Thr Gly Thr His Asn Leu Ser Leu Lys Ala Ile
                405                 410                 415

Asn Leu Ile Leu Asp Glu Leu Trp His Thr Asn Asp Asn Gln Ile Ala
            420                 425                 430

Ile Phe Asn Arg Leu Lys Leu Val Pro Lys Lys Val Asp Leu Ser Gln
        435                 440                 445

Gln Lys Glu Ile Pro Thr Thr Leu Val Asp Asp Phe Ile Leu Ser Pro
450                 455                 460

Val Val Lys Arg Ser Phe Ile Gln Ser Ile Lys Val Ile Asn Ala Ile
465                 470                 475                 480

Ile Lys Lys Tyr Gly Leu Pro Asn Asp Ile Ile Ile Glu Leu Ala Arg
                485                 490                 495

Glu Lys Asn Ser Lys Asp Ala Gln Lys Met Ile Asn Glu Met Gln Lys
            500                 505                 510

Arg Asn Arg Gln Thr Asn Glu Arg Ile Glu Glu Ile Ile Arg Thr Thr
        515                 520                 525

Gly Lys Glu Asn Ala Lys Tyr Leu Ile Glu Lys Ile Lys Leu His Asp
530                 535                 540

Met Gln Glu Gly Lys Cys Leu Tyr Ser Leu Glu Ala Ile Pro Leu Glu
545                 550                 555                 560

Asp Leu Leu Asn Asn Pro Phe Asn Tyr Glu Val Asp His Ile Ile Pro
                565                 570                 575

Arg Ser Val Ser Phe Asp Asn Ser Phe Asn Asn Lys Val Leu Val Lys
            580                 585                 590

Gln Glu Glu Ala Ser Lys Lys Gly Asn Arg Thr Pro Phe Gln Tyr Leu
        595                 600                 605

Ser Ser Ser Asp Ser Lys Ile Ser Tyr Glu Thr Phe Lys Lys His Ile
610                 615                 620

Leu Asn Leu Ala Lys Gly Lys Gly Arg Ile Ser Lys Thr Lys Lys Glu
625                 630                 635                 640

Tyr Leu Leu Glu Glu Arg Asp Ile Asn Arg Phe Ser Val Gln Lys Asp
                645                 650                 655

Phe Ile Asn Arg Asn Leu Val Asp Thr Arg Tyr Ala Thr Arg Gly Leu
            660                 665                 670

Met Asn Leu Leu Arg Ser Tyr Phe Arg Val Asn Asn Leu Asp Val Lys
        675                 680                 685

Val Lys Ser Ile Asn Gly Gly Phe Thr Ser Phe Leu Arg Arg Lys Trp
690                 695                 700
```

-continued

```
Lys Phe Lys Lys Glu Arg Asn Lys Gly Tyr Lys His His Ala Glu Asp
705                 710                 715                 720

Ala Leu Ile Ile Ala Asn Ala Asp Phe Ile Phe Lys Glu Trp Lys Lys
            725                 730                 735

Leu Asp Lys Ala Lys Lys Val Met Glu Asn Gln Met Phe Glu Glu Lys
        740                 745                 750

Gln Ala Glu Ser Met Pro Glu Ile Glu Thr Glu Gln Glu Tyr Lys Glu
    755                 760                 765

Ile Phe Ile Thr Pro His Gln Ile Lys His Ile Lys Asp Phe Lys Asp
770                 775                 780

Tyr Lys Tyr Ser His Arg Val Asp Lys Lys Pro Asn Arg Glu Leu Ile
785                 790                 795                 800

Asn Asp Thr Leu Tyr Ser Thr Arg Lys Asp Asp Lys Gly Asn Thr Leu
            805                 810                 815

Ile Val Asn Asn Leu Asn Gly Leu Tyr Asp Lys Asp Asn Asp Lys Leu
        820                 825                 830

Lys Lys Leu Ile Asn Lys Ser Pro Glu Lys Leu Leu Met Tyr His His
    835                 840                 845

Asp Pro Gln Thr Tyr Gln Lys Leu Lys Leu Ile Met Glu Gln Tyr Gly
850                 855                 860

Asp Glu Lys Asn Pro Leu Tyr Lys Tyr Tyr Glu Glu Thr Gly Asn Tyr
865                 870                 875                 880

Leu Thr Lys Tyr Ser Lys Lys Asp Asn Gly Pro Val Ile Lys Lys Ile
            885                 890                 895

Lys Tyr Tyr Gly Asn Lys Leu Asn Ala His Leu Asp Ile Thr Asp Asp
        900                 905                 910

Tyr Pro Asn Ser Arg Asn Lys Val Val Lys Leu Ser Leu Lys Pro Tyr
    915                 920                 925

Arg Phe Asp Val Tyr Leu Asp Asn Gly Val Tyr Lys Phe Val Thr Val
930                 935                 940

Lys Asn Leu Asp Val Ile Lys Lys Glu Asn Tyr Tyr Glu Val Asn Ser
945                 950                 955                 960

Lys Cys Tyr Glu Glu Ala Lys Lys Leu Lys Lys Ile Ser Asn Gln Ala
            965                 970                 975

Glu Phe Ile Ala Ser Phe Tyr Asn Asn Asp Leu Ile Lys Ile Asn Gly
        980                 985                 990

Glu Leu Tyr Arg Val Ile Gly Val Asn Asn Asp Leu Leu Asn Arg Ile
    995                 1000                1005

Glu Val Asn Met Ile Asp Ile Thr Tyr Arg Glu Tyr Leu Glu Asn
    1010                1015                1020

Met Asn Asp Lys Arg Pro Pro Arg Ile Ile Lys Thr Ile Ala Ser
    1025                1030                1035

Lys Thr Gln Ser Ile Lys Lys Tyr Ser Thr Asp Ile Leu Gly Asn
    1040                1045                1050

Leu Tyr Glu Val Lys Ser Lys Lys His Pro Gln Ile Ile Lys Lys
    1055                1060                1065

Gly Lys Arg Pro Ala Ala Thr Lys Lys Ala Gly Gln Ala Lys Lys
    1070                1075                1080

Lys Lys Gly Ser Asp Ala Lys Ser Leu Thr Ala Trp Ser Arg Thr
    1085                1090                1095

Leu Val Thr Phe Lys Asp Val Phe Val Asp Phe Thr Arg Glu Glu
    1100                1105                1110
```

```
Trp Lys Leu Leu Asp Thr Ala Gln Gln Ile Val Tyr Arg Asn Val
    1115            1120                1125

Met Leu Glu Asn Tyr Lys Asn Leu Val Ser Leu Gly Tyr Gln Leu
    1130            1135                1140

Thr Lys Pro Asp Val Ile Leu Arg Leu Glu Lys Gly Glu Glu Pro
    1145            1150                1155

<210> SEQ ID NO 22
<211> LENGTH: 1483
<212> TYPE: PRT
<213> ORGANISM: Artificial Sequence
<220> FEATURE:
<223> OTHER INFORMATION: Synthetic Polypeptide

<400> SEQUENCE: 22

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65              70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320
```

-continued

```
Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735
```

```
Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
   1010                1015                1020

Lys Ser Glu Gln Glu Ile Gly Lys Ala Thr Ala Lys Tyr Phe Phe
   1025                1030                1035

Tyr Ser Asn Ile Met Asn Phe Phe Lys Thr Glu Ile Thr Leu Ala
   1040                1045                1050

Asn Gly Glu Ile Arg Lys Arg Pro Leu Ile Glu Thr Asn Gly Glu
   1055                1060                1065

Thr Gly Glu Ile Val Trp Asp Lys Gly Arg Asp Phe Ala Thr Val
   1070                1075                1080

Arg Lys Val Leu Ser Met Pro Gln Val Asn Ile Val Lys Lys Thr
   1085                1090                1095

Glu Val Gln Thr Gly Gly Phe Ser Lys Glu Ser Ile Leu Pro Lys
   1100                1105                1110

Arg Asn Ser Asp Lys Leu Ile Ala Arg Lys Lys Asp Trp Asp Pro
   1115                1120                1125

Lys Lys Tyr Gly Gly Phe Asp Ser Pro Thr Val Ala Tyr Ser Val
   1130                1135                1140
```

Leu Val Val Ala Lys Val Glu Lys Gly Lys Ser Lys Lys Leu Lys
1145                1150                1155

Ser Val Lys Glu Leu Leu Gly Ile Thr Ile Met Glu Arg Ser Ser
1160                1165                1170

Phe Glu Lys Asn Pro Ile Asp Phe Leu Glu Ala Lys Gly Tyr Lys
1175                1180                1185

Glu Val Lys Lys Asp Leu Ile Ile Lys Leu Pro Lys Tyr Ser Leu
1190                1195                1200

Phe Glu Leu Glu Asn Gly Arg Lys Arg Met Leu Ala Ser Ala Gly
1205                1210                1215

Glu Leu Gln Lys Gly Asn Glu Leu Ala Leu Pro Ser Lys Tyr Val
1220                1225                1230

Asn Phe Leu Tyr Leu Ala Ser His Tyr Glu Lys Leu Lys Gly Ser
1235                1240                1245

Pro Glu Asp Asn Glu Gln Lys Gln Leu Phe Val Glu Gln His Lys
1250                1255                1260

His Tyr Leu Asp Glu Ile Ile Glu Gln Ile Ser Glu Phe Ser Lys
1265                1270                1275

Arg Val Ile Leu Ala Asp Ala Asn Leu Asp Lys Val Leu Ser Ala
1280                1285                1290

Tyr Asn Lys His Arg Asp Lys Pro Ile Arg Glu Gln Ala Glu Asn
1295                1300                1305

Ile Ile His Leu Phe Thr Leu Thr Asn Leu Gly Ala Pro Ala Ala
1310                1315                1320

Phe Lys Tyr Phe Asp Thr Thr Ile Asp Arg Lys Arg Tyr Thr Ser
1325                1330                1335

Thr Lys Glu Val Leu Asp Ala Thr Leu Ile His Gln Ser Ile Thr
1340                1345                1350

Gly Leu Tyr Glu Thr Arg Ile Asp Leu Ser Gln Leu Gly Gly Asp
1355                1360                1365

Gly Thr Gly Gly Pro Lys Lys Lys Arg Lys Val Tyr Pro Tyr Asp
1370                1375                1380

Val Pro Asp Tyr Ala Gly Tyr Pro Tyr Asp Val Pro Asp Tyr Ala
1385                1390                1395

Gly Ser Tyr Pro Tyr Asp Val Pro Asp Tyr Ala Gly Ser Met Asp
1400                1405                1410

Ala Lys Ser Leu Thr Ala Trp Ser Arg Thr Leu Val Thr Phe Lys
1415                1420                1425

Asp Val Phe Val Asp Phe Thr Arg Glu Glu Trp Lys Leu Leu Asp
1430                1435                1440

Thr Ala Gln Gln Ile Val Tyr Arg Asn Val Met Leu Glu Asn Tyr
1445                1450                1455

Lys Asn Leu Val Ser Leu Gly Tyr Gln Leu Thr Lys Pro Asp Val
1460                1465                1470

Ile Leu Arg Leu Glu Lys Gly Glu Glu Pro
1475                1480

<210> SEQ ID NO 23
<211> LENGTH: 1069
<212> TYPE: PRT
<213> ORGANISM: Artificial Sequence
<220> FEATURE:
<223> OTHER INFORMATION: Synthetic Polypeptide

<400> SEQUENCE: 23

```
Met Ala Pro Lys Lys Arg Lys Val Gly Ile His Gly Val Pro Ala
1               5                   10                  15

Ala Lys Arg Asn Tyr Ile Leu Gly Leu Ala Ile Gly Ile Thr Ser Val
            20                  25                  30

Gly Tyr Gly Ile Ile Asp Tyr Glu Thr Arg Asp Val Ile Asp Ala Gly
        35                  40                  45

Val Arg Leu Phe Lys Glu Ala Asn Val Glu Asn Asn Glu Gly Arg Arg
50                  55                  60

Ser Lys Arg Gly Ala Arg Arg Leu Lys Arg Arg Arg His Arg Ile
65                  70                  75                  80

Gln Arg Val Lys Lys Leu Leu Phe Asp Tyr Asn Leu Leu Thr Asp His
                85                  90                  95

Ser Glu Leu Ser Gly Ile Asn Pro Tyr Glu Ala Arg Val Lys Gly Leu
            100                 105                 110

Ser Gln Lys Leu Ser Glu Glu Phe Ser Ala Ala Leu Leu His Leu
        115                 120                 125

Ala Lys Arg Arg Gly Val His Asn Val Asn Glu Val Glu Glu Asp Thr
130                 135                 140

Gly Asn Glu Leu Ser Thr Lys Glu Gln Ile Ser Arg Asn Ser Lys Ala
145                 150                 155                 160

Leu Glu Glu Lys Tyr Val Ala Glu Leu Gln Leu Glu Arg Leu Lys Lys
                165                 170                 175

Asp Gly Glu Val Arg Gly Ser Ile Asn Arg Phe Lys Thr Ser Asp Tyr
            180                 185                 190

Val Lys Glu Ala Lys Gln Leu Leu Lys Val Gln Lys Ala Tyr His Gln
        195                 200                 205

Leu Asp Gln Ser Phe Ile Asp Thr Tyr Ile Asp Leu Leu Glu Thr Arg
210                 215                 220

Arg Thr Tyr Tyr Glu Gly Pro Gly Glu Gly Ser Pro Phe Gly Trp Lys
225                 230                 235                 240

Asp Ile Lys Glu Trp Tyr Glu Met Leu Met Gly His Cys Thr Tyr Phe
                245                 250                 255

Pro Glu Glu Leu Arg Ser Val Lys Tyr Ala Tyr Asn Ala Asp Leu Tyr
            260                 265                 270

Asn Ala Leu Asn Asp Leu Asn Asn Leu Val Ile Thr Arg Asp Glu Asn
        275                 280                 285

Glu Lys Leu Glu Tyr Tyr Glu Lys Phe Gln Ile Ile Glu Asn Val Phe
290                 295                 300

Lys Gln Lys Lys Lys Pro Thr Leu Lys Gln Ile Ala Lys Glu Ile Leu
305                 310                 315                 320

Val Asn Glu Glu Asp Ile Lys Gly Tyr Arg Val Thr Ser Thr Gly Lys
                325                 330                 335

Pro Glu Phe Thr Asn Leu Lys Val Tyr His Asp Ile Lys Asp Ile Thr
            340                 345                 350

Ala Arg Lys Glu Ile Ile Glu Asn Ala Glu Leu Leu Asp Gln Ile Ala
        355                 360                 365

Lys Ile Leu Thr Ile Tyr Gln Ser Ser Glu Asp Ile Gln Glu Glu Leu
370                 375                 380

Thr Asn Leu Asn Ser Glu Leu Thr Gln Glu Glu Ile Glu Gln Ile Ser
385                 390                 395                 400

Asn Leu Lys Gly Tyr Thr Gly Thr His Asn Leu Ser Leu Lys Ala Ile
                405                 410                 415
```

-continued

Asn Leu Ile Leu Asp Glu Leu Trp His Thr Asn Asp Asn Gln Ile Ala
            420                 425                 430

Ile Phe Asn Arg Leu Lys Leu Val Pro Lys Lys Val Asp Leu Ser Gln
            435                 440                 445

Gln Lys Glu Ile Pro Thr Thr Leu Val Asp Asp Phe Ile Leu Ser Pro
        450                 455                 460

Val Val Lys Arg Ser Phe Ile Gln Ser Ile Lys Val Ile Asn Ala Ile
465                 470                 475                 480

Ile Lys Lys Tyr Gly Leu Pro Asn Asp Ile Ile Glu Leu Ala Arg
                485                 490                 495

Glu Lys Asn Ser Lys Asp Ala Gln Lys Met Ile Asn Glu Met Gln Lys
            500                 505                 510

Arg Asn Arg Gln Thr Asn Glu Arg Ile Glu Glu Ile Arg Thr Thr
            515                 520                 525

Gly Lys Glu Asn Ala Lys Tyr Leu Ile Glu Lys Ile Lys Leu His Asp
        530                 535                 540

Met Gln Glu Gly Lys Cys Leu Tyr Ser Leu Glu Ala Ile Pro Leu Glu
545                 550                 555                 560

Asp Leu Leu Asn Asn Pro Phe Asn Tyr Glu Val Asp His Ile Ile Pro
                565                 570                 575

Arg Ser Val Ser Phe Asp Asn Ser Phe Asn Asn Lys Val Leu Val Lys
            580                 585                 590

Gln Glu Glu Ala Ser Lys Lys Gly Asn Arg Thr Pro Phe Gln Tyr Leu
        595                 600                 605

Ser Ser Ser Asp Ser Lys Ile Ser Tyr Glu Thr Phe Lys Lys His Ile
610                 615                 620

Leu Asn Leu Ala Lys Gly Lys Gly Arg Ile Ser Lys Thr Lys Lys Glu
625                 630                 635                 640

Tyr Leu Leu Glu Glu Arg Asp Ile Asn Arg Phe Ser Val Gln Lys Asp
                645                 650                 655

Phe Ile Asn Arg Asn Leu Val Asp Thr Arg Tyr Ala Thr Arg Gly Leu
            660                 665                 670

Met Asn Leu Leu Arg Ser Tyr Phe Arg Val Asn Asn Leu Asp Val Lys
            675                 680                 685

Val Lys Ser Ile Asn Gly Gly Phe Thr Ser Phe Leu Arg Arg Lys Trp
        690                 695                 700

Lys Phe Lys Lys Glu Arg Asn Lys Gly Tyr Lys His His Ala Glu Asp
705                 710                 715                 720

Ala Leu Ile Ile Ala Asn Ala Asp Phe Ile Phe Lys Glu Trp Lys Lys
                725                 730                 735

Leu Asp Lys Ala Lys Lys Val Met Glu Asn Gln Met Phe Glu Glu Lys
            740                 745                 750

Gln Ala Glu Ser Met Pro Glu Ile Glu Thr Glu Gln Glu Tyr Lys Glu
        755                 760                 765

Ile Phe Ile Thr Pro His Gln Ile Lys His Ile Lys Asp Phe Lys Asp
770                 775                 780

Tyr Lys Tyr Ser His Arg Val Asp Lys Lys Pro Asn Arg Glu Leu Ile
785                 790                 795                 800

Asn Asp Thr Leu Tyr Ser Thr Arg Lys Asp Asp Lys Gly Asn Thr Leu
                805                 810                 815

Ile Val Asn Asn Leu Asn Gly Leu Tyr Asp Lys Asp Asn Asp Lys Leu
            820                 825                 830

Lys Lys Leu Ile Asn Lys Ser Pro Glu Lys Leu Leu Met Tyr His His
835                 840                 845

Asp Pro Gln Thr Tyr Gln Lys Leu Lys Leu Ile Met Glu Gln Tyr Gly
850                 855                 860

Asp Glu Lys Asn Pro Leu Tyr Lys Tyr Glu Glu Thr Gly Asn Tyr
865                 870                 875                 880

Leu Thr Lys Tyr Ser Lys Lys Asp Asn Gly Pro Val Ile Lys Lys Ile
                885                 890                 895

Lys Tyr Tyr Gly Asn Lys Leu Asn Ala His Leu Asp Ile Thr Asp Asp
                900                 905                 910

Tyr Pro Asn Ser Arg Asn Lys Val Val Lys Leu Ser Leu Lys Pro Tyr
                915                 920                 925

Arg Phe Asp Val Tyr Leu Asp Asn Gly Val Tyr Lys Phe Val Thr Val
                930                 935                 940

Lys Asn Leu Asp Val Ile Lys Lys Glu Asn Tyr Tyr Glu Val Asn Ser
945                 950                 955                 960

Lys Cys Tyr Glu Glu Ala Lys Lys Leu Lys Lys Ile Ser Asn Gln Ala
                965                 970                 975

Glu Phe Ile Ala Ser Phe Tyr Asn Asn Asp Leu Ile Lys Ile Asn Gly
                980                 985                 990

Glu Leu Tyr Arg Val Ile Gly Val Asn Asn Asp Leu Leu Asn Arg Ile
                995                 1000                1005

Glu Val Asn Met Ile Asp Ile Thr Tyr Arg Glu Tyr Leu Glu Asn
        1010                1015                1020

Met Asn Asp Lys Arg Pro Pro Arg Ile Ile Lys Thr Ile Ala Ser
        1025                1030                1035

Lys Thr Gln Ser Ile Lys Lys Tyr Ser Thr Asp Ile Leu Gly Asn
        1040                1045                1050

Leu Tyr Glu Val Lys Ser Lys His Pro Gln Ile Ile Lys Lys
        1055                1060                1065

Gly

<210> SEQ ID NO 24
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 24
atgcttcgtg atgacc                                                       16

<210> SEQ ID NO 25
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 25
atcagcctta attcga                                                       16

<210> SEQ ID NO 26
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 26
cagcgtcgga aggtgg                                                    16

<210> SEQ ID NO 27
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 27
aacacgtcta tacgc                                                     15

<210> SEQ ID NO 28
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 28
gctctgctgg aggagcttta gga                                            23

<210> SEQ ID NO 29
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 29
gcaggtctgc wggtacctgg                                                20

<210> SEQ ID NO 30
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 30
tcgtggacag catcacagt                                                 19

<210> SEQ ID NO 31
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 31
cttcctagca tcagggcag                                                 19

<210> SEQ ID NO 32
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 32
gtagcaggtg taaccgtaac c                                              21

```
<210> SEQ ID NO 33
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 33
cagagataaa tacagcccca gg                                              22

<210> SEQ ID NO 34
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 34
acagaagcgc aatgttgaag                                                 20

<210> SEQ ID NO 35
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 35
cacctttgct tgcagtttgt                                                 20

<210> SEQ ID NO 36
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 36
tctacagaga cgtaggctgt ca                                              22

<210> SEQ ID NO 37
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 37
cttgagcacg agcttggtag                                                 20

<210> SEQ ID NO 38
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 38
agtaagtgcg ggtcataagc t                                               21

<210> SEQ ID NO 39
<211> LENGTH: 22
<212> TYPE: DNA
<213> ORGANISM: Artificial Sequence
<220> FEATURE:
<223> OTHER INFORMATION: Synthetic Polynucleotide
```

<400> SEQUENCE: 39
cctcactaaa ccatccaatc gg								22

<210> SEQ ID NO 40
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 40
tgcgacagtg tattcgcaac								20

<210> SEQ ID NO 41
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 41
ggctttggtc ctcgtttctt								20

<210> SEQ ID NO 42
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 42
gctcattcca gcaccaattc								20

<210> SEQ ID NO 43
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 43
ccattcatcc acaccctcat								20

<210> SEQ ID NO 44
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 44
aaacactcaa gccatccaca								20

<210> SEQ ID NO 45
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 45
gcttttctaa ttcccgcttt t								21

```
<210> SEQ ID NO 46
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 46
caccgaaagc cgtttgtgag                                              20

<210> SEQ ID NO 47
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 47
tctacccgtc acagcacaac                                              20

<210> SEQ ID NO 48
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 48
tctgctggag gagctttag                                               19

<210> SEQ ID NO 49
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 49
gaatggcagt tctccgcg                                                18

<210> SEQ ID NO 50
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 50 cctatacccca ccagcttctt                                             20

<210> SEQ ID NO 51
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 51
gatgtgattc cccttctttc                                              20

<210> SEQ ID NO 52
<211> LENGTH: 20
<212> TYPE: DNA
<213> ORGANISM: Artificial Sequence
<220> FEATURE:
<223> OTHER INFORMATION: Synthetic Polynucleotide
```

```
<400> SEQUENCE: 52
atctggttgt ggtagtgtgc                                                    20

<210> SEQ ID NO 53
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 53
tgagggtgtc tgaaagaatg                                                    20

<210> SEQ ID NO 54
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 54
tgggaaatac ctgctacgtg                                                    20

<210> SEQ ID NO 55
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 55
gtgacgatga cacgtttgag                                                    20
```

THERAPEUTIC TARGETS FOR FACIOSCAPULOHUMERAL MUSCULAR DYSTROPHY

CROSS-REFERENCE TO RELATED APPLICATIONS

This application is a National Stage Application of PCT/US2017/060410, filed Nov. 7, 2017, entitled "THERAPEUTIC TARGETS FOR FACIOSCAPULOHUMERAL MUSCULAR DYSTROPHY", which claims the benefit under 35 U.S.C. § 119(e) of the filing date of U.S. provisional application serial numbers U.S. Ser. No. 62/418,694, filed Nov. 7, 2016, entitled "IDENTIFICATION OF THERAPEUTIC TARGETS FOR FACIOSCAPULOHUMERAL MUSCULAR DYSTROPHY," and 62/490,783, filed Apr. 27, 2017, entitled "IDENTIFICATION OF THERAPEUTIC TARGETS FOR FACIOSCAPULOHUMERAL MUSCULAR DYSTROPHY", the contents of each application which are incorporated by reference herein.

GOVERNMENT SUPPORT

This invention was made with government support under AR062587 awarded by the National Institutes of Health. The government has certain rights in the invention.

BACKGROUND

Facioscapulohumeral muscular dystrophy (FSHD) is caused by the aberrant expression of the DUX4 gene from an epigenetically dysregulated D4Z4 array at chromosome 4q35. This gene is generally not expressed, or expressed at very low levels, in healthy individuals. In FSHD patients, DUX4 gene is aberrantly expressed at higher levels in the skeletal muscles. This aberrant expression ultimately leads to muscle pathology, atrophy, and clinical weakness. Most therapies being developed target the DUX4 mRNA or protein.

Several therapeutic agents that target DUX4 mRNA of protein have been investigated for treatment of FSHD. However, effective human treatments remain needed. To date, no specific therapy exists for FSHD, and current treatments are only directed to improve behavioral symptoms. Thus, there is a general need for the development of novel compositions and methods for treating FSHD.

SUMMARY

In some aspects, the disclosure relates to compositions and methods useful for the treatment of diseases associated with aberrant expression of DUX4 (e.g., facioscapulohumeral muscular dystrophy, FSHD). In some embodiments, epigenetic modulators disclosed herein are useful because they epigenetically regulate (e.g., inhibit) aberrant expression of DUX4. In some embodiments, reduction of DUX4 expression by epigenetic modulators (e.g., selective inhibitors) in subjects having diseases characterized by aberrant expression of DUX4 (e.g., FSHD) is expected to result in reduced expression of the pathogenic DUX4-FL protein and thereby decrease disease symptomatology or reverse disease symptoms. In some embodiments, the epigenetic modulator reduces ZSCAN4 gene expression in a subject.

Aspects of the disclosure relate to the discovery that inhibition of DUX4 gene expression by epigenetic modulators (e.g., selective inhibitors) results in reduction in DUX4 gene expression and/or reduction of DUX4 protein (e.g., DUX4-FL) protein production. For example, selective inhibition of genes encoding certain Bromodomain-containing proteins (e.g., BRD2, BAZ1A, etc.), histone demethylases (e.g., KDM4C), certain methyltransferases (e.g., ASH1L), and chromatin remodeling proteins (e.g., SMARCA5, SMARCB1, etc.) results in reduction of DUX4 gene expression (e.g., epigenetic silencing of the DUX4 gene). Thus, in some embodiments, selective epigenetic modulators of DUX4 gene reduce production of pathogenic DUX4-FL protein and are useful for treating FSHD.

In some aspects the disclosure provides a method for treating facioscapulohumeral muscular dystrophy (FSHD) in a subject in need thereof. In some embodiments, the methods comprises: administering to the subject a therapeutically effective amount of an epigenetic modulator of DUX4 gene expression. In some embodiments, the epigenetic modulator reduces DUX4 expression in the muscle cells, muscle progenitor cells, or muscle stem cells of the subject.

In some embodiments, the epigenetic modulator of DUX4 is not an interfering nucleic acid that hybridizes to DUX4.

In some embodiments, the epigenetic modulator of DUX4 is an inhibitor of a demethylase enzyme. In some embodiments, the demethylase is a lysine-specific demethylase. In some embodiments, the lysine-specific demethylase is selected from the group consisting of: KDM4A, KDM4B, KDM4C, KDM4D, KDM6A, KDM6B, and PHF2. In some embodiments, the lysine-specific demethylase is KDMC4C and the epigenetic modulator specifically inhibits KDM4C.

In some embodiments, the epigenetic modulator is an inhibitor of a bromodomain-containing protein (BRD). In some embodiments, the BRD protein is BRD2, BRD3, BRDT, ASH1L, BRPF1, BRPF3, BPTF, BAZ1A, BAZ1B, or BAZ2A. In some embodiments, the BRD protein is BRD2 and the epigenetic modulator specifically inhibits BRD2. In some embodiments, the BRD protein is BAZ1A and the epigenetic modulator specifically inhibits BAZ1A.

In some embodiments, the epigenetic modulator is an inhibitor of a chromatin remodeling protein. In some embodiments, the chromatin remodeling protein is SMARCA5 or SMARCB1.

In some embodiments, the protein involved with chromatin remodeling is SMARCA5 and the epigenetic modulator specifically inhibits SMARCA5.

In some embodiments, the epigenetic modulator of DUX4 is an inhibitor of a methyltransferase enzyme. In some embodiments, the methyltransferase is CARM1, DOT1L, KMT2A, KMT2C, KMT2E, PRMT1, SETD1A, SETD1B, SMYD3, or ASH1L. In some embodiments, the methyltransferase is ASH1L and the epigenetic modulator specifically inhibits ASH1L.

In some embodiments, the epigenetic modulator of DUX4 is a nucleic acid, polypeptide, or small molecule.

In some embodiments, the epigenetic modulator of DUX4 is a nucleic acid. In some embodiments, the nucleic acid is an interfering nucleic acid selected from the group consisting of: double stranded RNA (dsRNA), siRNA, shRNA, miRNA, and antisense oligonucleotide (ASO). In some embodiments, the epigenetic modulator of DUX4 is an interfering nucleic acid having a sequence as listed in Table 1.

In some embodiments, the epigenetic modulator of DUX4 is a polypeptide. In some embodiments, wherein the polypeptide is an antibody.

In some embodiments, the epigenetic modulator of DUX4 is a small molecule. Aspects of the disclosure relate, in part, on the discovery that small molecules that alter DUX4 expression by altering myogenic differentiation (e.g., JQ1) are not, in some embodiments, viable candidates for treatment of FSHD. Accordingly, in some embodiments, the small molecule inhibits DUX4 expression without altering or substantially altering one or more myogenic regulatory genes in the cells of the subject. In some embodiments, the one or more myogenic regulatory genes are selected from the group consisting of myogenin (Myog), MyoD, and myosin heavy chain (MyHC). In some embodiments, the small molecule does not inhibit myodifferentiation in the cells of the subject. In some embodiments, the epigenetic modulator of DUX4 is not JQ1, or an analogue of JQ1.

In some embodiments, the muscle cells are differentiated muscle cells, optionally terminally differentiated muscle cells. In some embodiments, the effective amount is administered to a muscle cell of the subject ex vivo.

In some embodiments, the muscle cell comprises an epigenetically dysregulated D4Z4 array at chromosome 4q35. In some embodiments, the epigenetically dysregulated D4Z4 array comprises fewer than 11 repeat units.

In some embodiments, the method further comprises assessing the DUX4 expression level of the subject before and/or after the administering, wherein a change in the DUX4 expression level indicates effectiveness of the treatment.

In some aspects, the disclosure provides a method for identifying an epigenetic modulator of DUX4 gene expression. In some embodiments, the method comprises (i) contacting a cell characterized by expression of DUX4 with a candidate agent for modulating expression or activity of a putative chromatin modifier of DUX4; (ii) detecting expression level of DUX4 in the cell; and, (iii) identifying the candidate agent as an epigenetic modulator of DUX4 when the expression level of DUX4 decreases relative to a control cell after contact with the candidate agent.

In some embodiments, the cell and/or the control cell is a muscle cell, such as a terminally differentiated muscle cell. In some embodiments, the cell comprises an epigenetically dysregulated D4Z4 array. In some embodiments, a corresponding control cell does not comprise an epigenetically dysregulated D4Z4 array.

In some embodiments, a candidate agent is selected from a compound library. In some embodiments, the library comprises or consists of demethylase inhibitors. In some embodiments, the demethylase inhibitors are lysine-specific demethylase inhibitors. In some embodiments, the library comprises or consists of bromodomain inhibitors. In some embodiments, the library comprises or consists of inhibitors of chromatin remodeling proteins (e.g., SMARCA5 inhibitors, etc.). In some embodiments, the library comprises or consists of methyltransferase inhibitors (e.g., ASH1L inhibitors).

In some embodiments, a candidate agent is a nucleic acid, polypeptide, or small molecule.

In some embodiments, a candidate agent is a nucleic acid. In some embodiments, the nucleic acid is an interfering nucleic acid selected from the group consisting of: double stranded RNA (dsRNA), siRNA, shRNA, miRNA, and antisense oligonucleotide (ASO).

In some embodiments, a candidate agent is a polypeptide. In some embodiments, the polypeptide is an antibody.

In some embodiments, a candidate agent is a small molecule.

In some embodiments, expression levels of DUX4 are detected using a hybridization-based assay, Western blot, flow cytometry, quantitative real-time polymerase chain reaction (qRT-PCR) or FACS.

Aspects of the disclosure relate to the development of gene editing complexes and/or molecules that are useful for bringing about a reduction in DUX4 gene expression. Thus, in some aspects, the disclosure provides a method for inhibiting DUX4 gene expression in a cell that involves contacting the cell with an effective amount of a recombinant gene editing complex, in which the gene editing complex brings about a reduction in expression of a lysine-specific demethylase, a BRD protein, a methyltransferase, or another chromatin remodeling protein in the cell.

In some embodiments, a recombinant gene editing complex does not hybridize or bind directly to DUX4.

In some embodiments, a recombinant gene editing complex comprises a Cas protein, a zinc finger nuclease (ZFN), a Transcription activator-like effector nuclease (TALEN), or a nuclease (e.g., a meganuclease).

In some embodiments, the Cas protein is a Cas9 protein, Cpf1 protein, or a variant thereof. In some embodiments, the Cas protein is a dead Cas9 (dCas9) protein, such as, for example a dCas9 protein comprising the sequence set forth in SEQ ID NO: 31.

In some embodiments, a recombinant gene editing complex further comprises a transcriptional repressor domain. In some embodiments, the transcriptional repressor domain is a KRAB domain. In some embodiments, a gene editing complex comprises a sequence set forth in SEQ ID NO: 29.

In some embodiments, a recombinant gene editing complex further comprises a guide RNA (gRNA), optionally a single-stranded guide RNA (sgRNA). In some embodiments, the gRNA or sgRNA hybridizes specifically to a gene encoding: a lysine-specific demethylase, a BRD protein, a methyltransferase, or a protein involved with chromatin remodeling. In some embodiments, the lysine-specific demethylase is KDM4C. In some embodiments, the BRD protein is BRD2. In some embodiments, the BRD protein is BAZ1A. In some embodiments, the chromatin remodeling protein is SMARCA5. In some embodiments, the methyltransferase is ASH1L.

In some embodiments, the recombinant gene editing complex is delivered to the cell by a viral vector, such as, for example, a lentiviral vector or a recombinant adeno-associated virus (rAAV) vector.

In some embodiments, a cell is a muscle cell, optionally a terminally differentiated muscle cell.

In some aspects, the disclosure provides a composition comprising a recombinant gene editing complex comprising (i) a recombinant gene editing protein; and, (ii) a guide RNA (gRNA) that specifically hybridizes to a lysine-specific demethylase, a BRD protein, a methyltransferase, or a protein involved with chromatin remodeling, in which binding of the guide strand to a target gene in a cell results in inhibition of DUX4 gene expression in the cell.

In some aspects, the disclosure provides a composition comprising a recombinant gene editing complex as described herein. In some embodiments, the composition comprises a viral vector (e.g., a lentiviral vector or a rAAV vector) encoding a gene editing complex as described by the disclosure. In some embodiments, the composition further comprises a pharmaceutically acceptable excipient.

In some aspects, the disclosure provides a method for treating facioscapulohumeral muscular dystrophy (FSHD) in a subject in need thereof, the method comprising: administering to the subject a therapeutically effective amount of a recombinant gene editing complex as described by the disclosure or a composition as described by the disclosure.

In some embodiments, the subject is a mammal, optionally a human.

In some embodiments, the recombinant gene editing complex is administered to the subject by injection, optionally intramuscular injection or intravenous injection.

In some embodiments, the recombinant gene editing complex is administered to muscle cells of the subject, optionally terminally differentiated muscle cells, muscle stem cells, muscle satellite cells, or myoblasts of the subject.

BRIEF DESCRIPTION OF DRAWINGS

FIG. 4A shows knockdown of ASH1L using 3 different shRNAs. FIG. 4B shows knockdown of BRD2 using two different shRNAs. FIG. 4C shows knockdown of KDM4C using three different shRNAs. FIG. 4D shows knockdown of SMARCA5 using two different shRNAs. FIG. 4E shows knockdown of BAZ1A using two different shRNAs.

FIG. 11F shows shRNAs to ASH1L (16169), BRD2 (6308), KDM4C (22058), or SMARCA5 (13214) reduce DUX4-fl expression across several FSHD cohorts (05Abic, 18Abic, and 17Abic). In all panels, relative mRNA expression for mock or control-infected cells is set to 1. Data are plotted as the mean+SD value of technical replicates.

Figure 15:
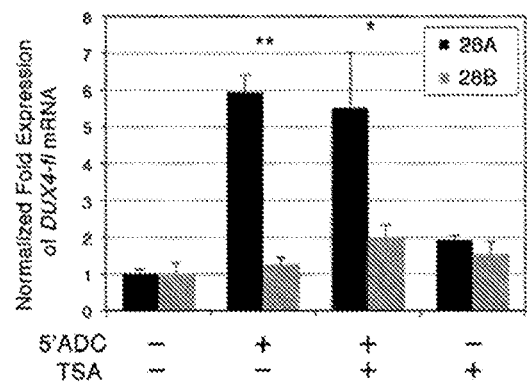
Figure 15:
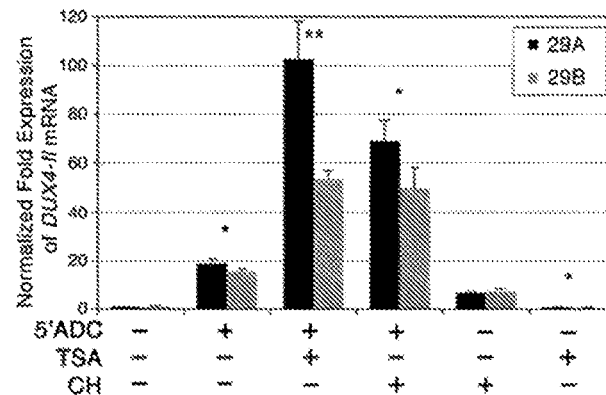
Figure 15:
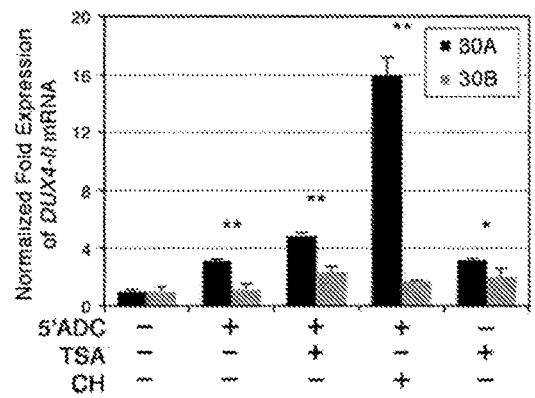
Figure 15:
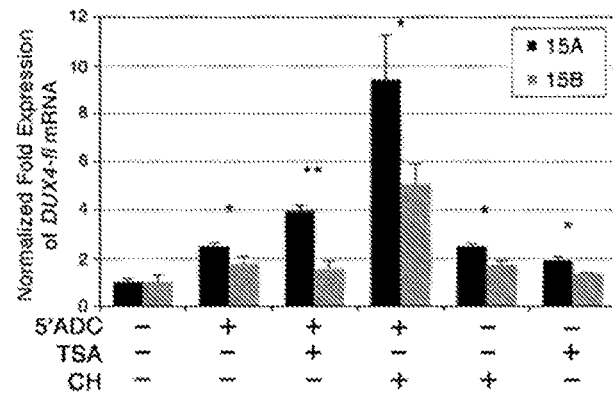

FIG. 15 shows treatment of primary myoblasts isolated from FSHD1-affected (A) and FSHD-asymptomatic (B) patients with small molecules alone or in combination that affect the epigenetic state of the D4Z4 affect DUX4 expression.

Figure 16:
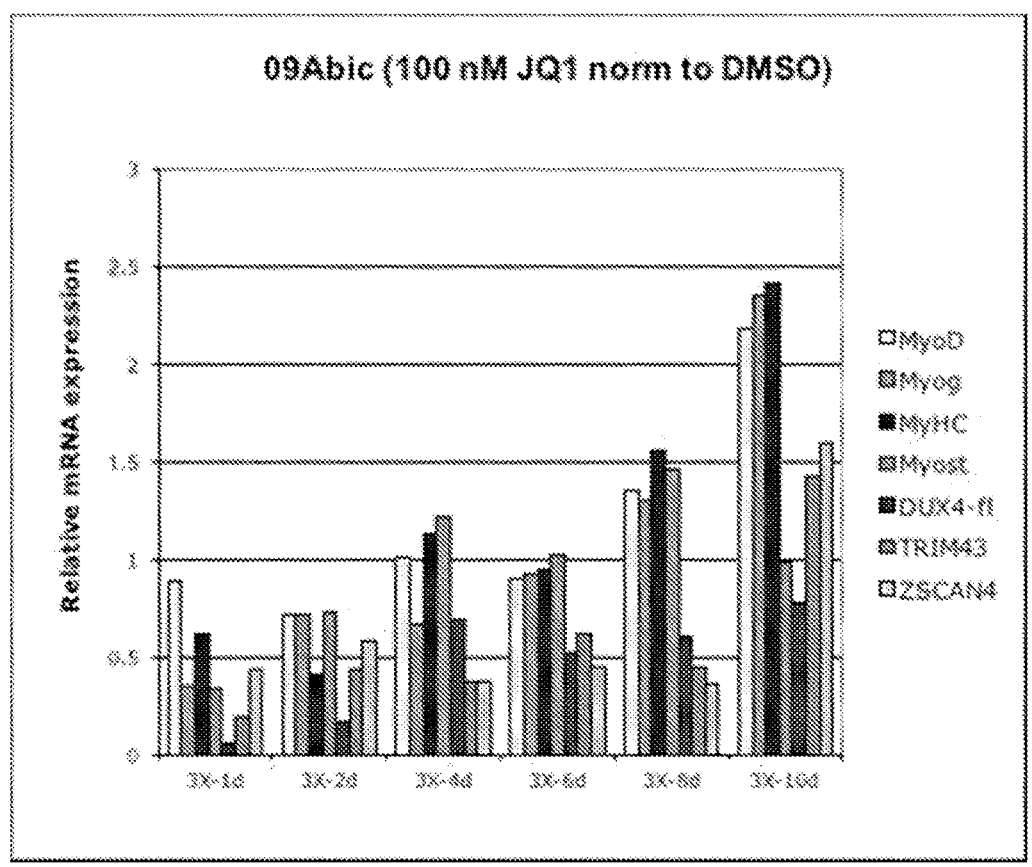

FIG. 16 shows JQ1 regulation of DUX4 is indirect and achieved by inhibiting the expression of several key myogenic regulatory genes myogenin (Myog), myoD, myosin heavy chain (MyHC), and myostatin (Myost).

Figure 17:
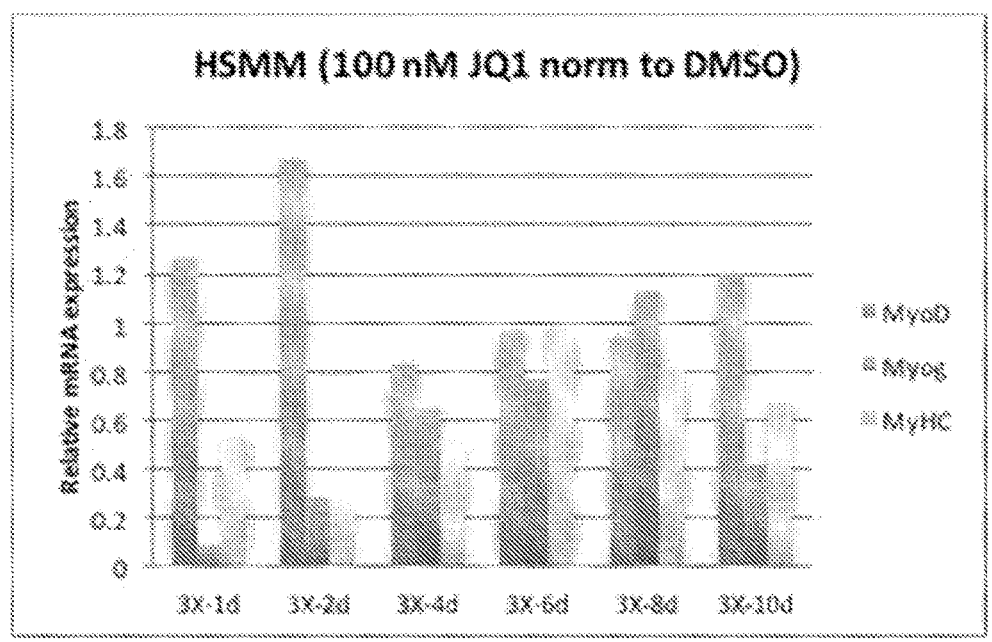

FIG. 17 shows that myogenic genes myogenin (Myog), myoD, myosin heavy chain (MyHC), are misregulated by JQ1 in both FSHD and healthy human skeletal muscle myoblasts (HSMM).

Figure 18:
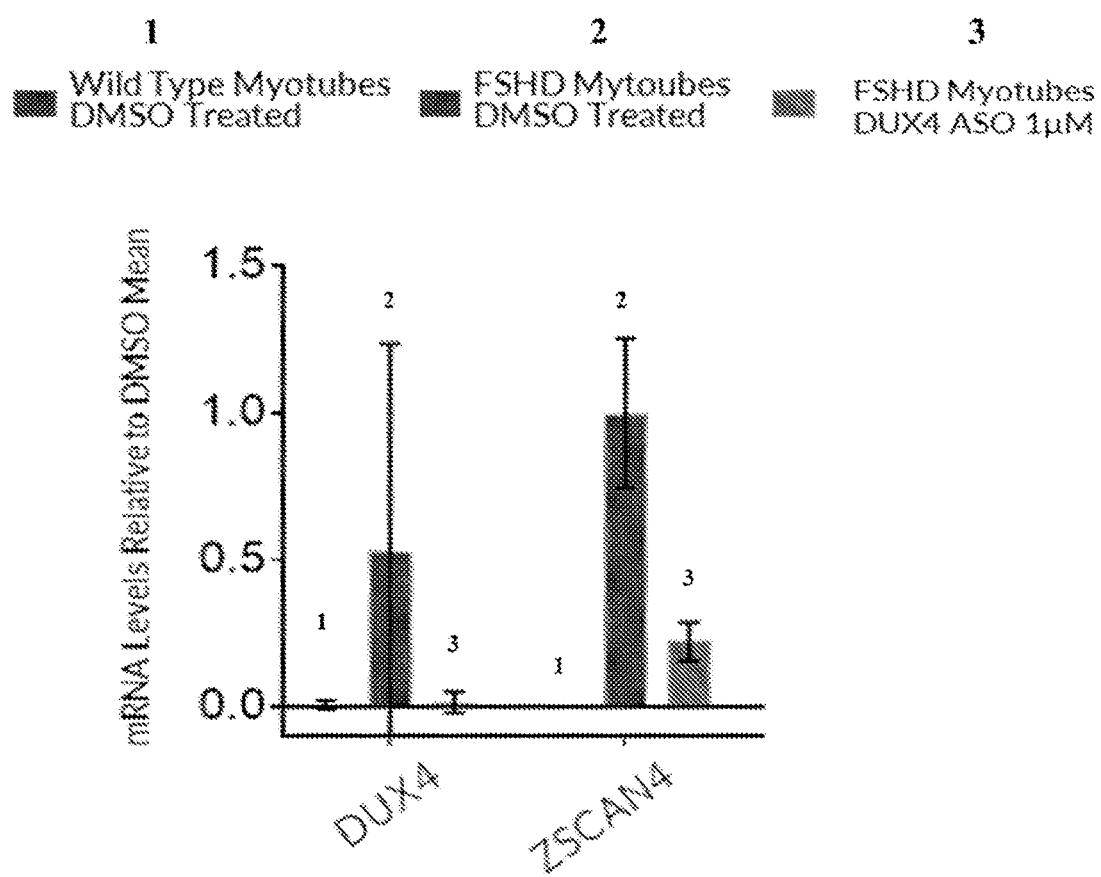

FIG. 18 shows representative data for ZSCAN4 expression in FSHD skeletal muscle myotubes in the absence and presence of DUX-4 antisense oligonucleotides. Relative gene expression of DUX-4 and ZSCAN4 are shown.

Figure 19:
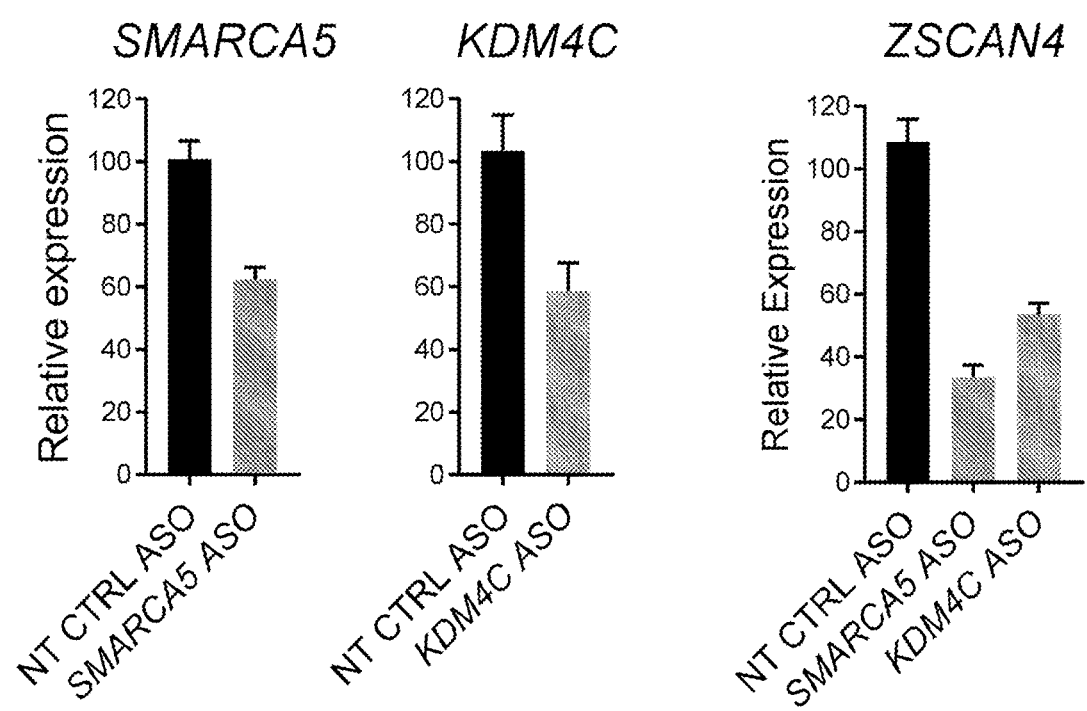

FIG. 19 shows representative data for ZSCAN4 expression in FSHD skeletal muscle myotubes in the absence and presence of SMARCA5 and KDM4C antisense oligonucleotides. Relative gene expression of SMARCA5, KDM4C and ZSCAN4 are shown.

DETAILED DESCRIPTION

In some aspects, the disclosure relates to methods and compositions useful for the treatment of diseases associated with aberrant expression of DUX4 (e.g., facioscapulohumeral muscular dystrophy, FSHD). The disclosure is based, in part, on the surprising discovery that inhibiting DUX4 gene expression using certain epigenetic modulators (e.g., inhibitors of KDM4C, ASH1L, SMARCA5, BAZ1A, BRD2, etc.) result in decreased production of DUX4-fl protein, the pathogenic mRNA isoform associated with FSHD. In some embodiments, methods and compositions described by the disclosure inhibit—for example, through RNA interference (RNAi)-mediated knockdown, gene-editing molecule-mediated knockdown, or small molecule inhibitors—DUX4 gene expression by targeting certain regulatory factors (e.g., chromatin modifiers) of DUX4. In some embodiments, the epigenetic modulator reduces ZSCAN4 gene expression in a subject.

Aspects of the disclosure are based, in part, on the discovery that certain inhibitors (e.g., certain indirect inhibitors) of DUX4 gene expression (e.g., JQ1, or analogues of JQ1) inhibit myogenesis or myodifferentiation of cells, for example by altering the kinetics of myogenic differentiation, and/or causing aberrant expression of myogenic regulatory factors, such as myogenin (Myog), MyoD, myosin heavy chain (MyHC), and myostatin (Myost). Thus, in some embodiments, epigenetic modulators of DUX4 expression as described by the disclosure do not inhibit myogenic regulatory genes (e.g. Myog, MyoD, MyHC, Myost, etc.). In some embodiments, the epigenetic modulator of DUX4 gene expression is not JQ1, or an analogue of JQ1.

Accordingly, in some aspects the disclosure provides a method for treating facioscapulohumeral muscular dystrophy (FSHD) in a subject in need thereof. In some embodiments, the method involves administering to the subject a therapeutically effective amount of an epigenetic modulator of DUX4 gene expression, in which the epigenetic modulator reduces DUX4 expression in the muscle cells of the subject.

Facioscapulohumeral Muscular Dystrophy (FSHD)

As used herein, the term "facioscapulohumeral muscular dystrophy" or "FSHD" refers to a muscular dystrophy involving progressive loss of skeletal muscle mass and/or function, in which muscles of the face, shoulder blades and upper arms are among the most affected. FSHD is associated with aberrant expression of DUX4. In certain embodiments, FSHD results from transcriptional activation of a DUX4 gene. In some embodiments, activation of the DUX4 gene results in a toxic gain of function in the DUX4 gene (e.g., production of pathogenic DUX4-fl) and causes a range of symptoms including progressive skeletal muscle weakness (e.g., facial muscle weakness, shoulder weakness, etc.), hearing loss, abnormal heart rhythm, unequal weakening of biceps, triceps, deltoids and lower arm muscles, loss of strength in abdominal and/or leg muscles, a foot drop. In some embodiments, FSHD results in a subject requiring ventiliatotry support or wheelchair confinement.

Generally, FSHD is associated with a contraction of the D4Z4 repeat sequence at the subtelomeric region 4q35 on Chromosome 4 of the human genome. Generally, chromosome 4 of a subject not having FSHD comprises a D4Z4 repeat region having between 11 and 150 repeat units, resulting in production of an alternatively-spliced 3'-truncated DUX4 transcript (DUX4-s). In some embodiments, the DUX4 gene of a subject having a contracted D4Z4 repeat (e.g., 11 or fewer repeat units) becomes transcriptionally activated due to the loss of repeat-mediated repression, resulting in production of pathogenic full-length DUX4 (DUX4-fl) mRNA and protein.

In some aspects, the invention relates to the discovery that inhibition of certain chromatin modifiers of DUX4 (e.g., KDM4C, ASH1L, SMARCA5, BAZ1A, BRD2, etc.) reduces DUX4 (e.g., DUX4-fl) expression in a subject (e.g., in a cell of a subject). As used herein, the term "reduced DUX4 expression" refers to a decrease in levels of DUX4 mRNA and/or protein in a cell or subject compared with an appropriate control. In some embodiments, reduced DUX4 expression is associated with a change in state of a DUX4 gene from a transcriptionally active (e.g., expressed or transcribed) state to a reduced state of transcriptional activity, for example, a transcriptionally inactive (e.g., silenced) state. For example, in some embodiments, a subject (e.g., a cell in a subject) having a transcriptionally active (e.g., expressed) DUX4 gene produces DUX4-fl; knockdown (e.g., silencing) of DUX4 expression in the subject (e.g., cell in the subject), for example by administration of an inhibitor of a chromatin modifier of DUX4, leads to reduced (or inhibited) expression and production of DUX4-fl in the subject.

In some embodiments, reduction of DUX4 expression can be measured as expression level of DUX4 in a sample (e.g., a cell or a subject) after treatment with an inhibitor of a chromatin modifier of DUX4 relative to expression level of DUX4 (e.g., DUX4-fl) in the sample prior to treatment with the inhibitor of the chromatin modifier of DUX4. Generally, the expression level of DUX4 (e.g., DUX4-fl) can be measured by any suitable method known in the art, for example by hybridization-based assay (e.g., RT-PCR, qRT-PCR, Northern Blot), protein-based methods (e.g., Western blot), spectroscopic methods (e.g., mass spectrometry), and cell-based methods (e.g., flow cytometry, fluorescence activated cell sorting (FACS)).

Epigenetic Modulators of DUX4

As used herein, the term "epigenetic modulator" refers to an agent that alters the transcriptional activity of a gene (e.g., DUX4), e.g., by affecting the chromatin state of that gene (e.g., promoting a condensed chromatin state to inhibit transcription or a relaxed chromatin state to enhance transcription). In some embodiments, an epigenetic modulator is an agent that, when delivered to a cell, e.g., a muscle cell, containing an active DUX4 gene, decreases transcription of DUX4 in the cell. In some embodiments, an epigenetic modulator directly modulates DUX4 gene expression. In some embodiments, an epigenetic modulator indirectly modulates DUX4 gene expression (e.g., does not bind directly to DUX4 gene locus or a D4Z4 repeat array, or regulates expression or activity of a direct chromatin modifier of DUX4 gene expression). For example, in some embodiments an epigenetic modulator is an RNAi molecule or small molecule inhibitor that targets a positive regulator (e.g., a chromatin modifier that promotes an open chromatin state at the DUX4 locus) of DUX4 gene expression, and thereby functions as a negative epigenetic modulator of DUX4 gene expression.

Aspects of the disclosure relate to the discovery that inhibiting certain regulatory factors (e.g., chromatin modifiers, such as KDM4C, BRD2, BAZ1A, ASH1L, SMARCA5, etc.) of DUX4 gene expression, for example using RNAi or small molecule inhibitors, results in inhibition of DUX4 gene expression and thus may be useful for treatment of diseases or conditions characterized by aberrant DUX4 expression (e.g., FSHD).

The chromatin state (e.g., packaging of DNA with histone and non-histone proteins) of a cell has significant effects on gene expression. In some embodiments, the disclosure relates to chromatin modifiers (e.g., chromatin remodeling proteins and genes encoding the same) that, when knocked down, reduce expression of the DUX4 gene in cells (e.g., muscle cells, such as terminally differentiated muscle cells). In some embodiments, an epigenetic modulator of DUX4 targets a chromatin modifier. As used herein, the term "chromatin modifier" refers to an agent (e.g., an enzyme or transcription factor) that modifies DNA (e.g., by methylation) or post-translationally modifies histone proteins (for example by phosphorylation, acetylation, methylation or ubiquitination), resulting in alteration of chromatin structure and thus modified gene expression. Examples of chromatin modifiers include, but are not limited to histone demethylases (e.g., lysine demethylase enzymes), histone methyltransferases, histone deacetylases, histone acetyltransferases, certain bromodomain-containing proteins, kinases (e.g., kinases that phosphorylate histones), and actin-dependent regulators of chromatin. In some embodiments, one or more chromatin remodeling proteins is present in a chromatin structure remodeling complex (RSC). Thus, in some embodiments, a chromatin modifier of DUX4 is a component (e.g., a protein present in) an RSC.

As used herein, the term "histone demethylase" refers to an enzyme that catalyzes the removal of a methyl group from a histone protein. In some embodiments, histone demethylase enzymes comprise one or more of the following domains: Swi3, Rsc and Moira (SWIRM1) domain, Jumonji N- or C-terminal (JmjN or JmjC) domain, PHD-finger domain, Zinc-finger domain, amine oxidase domain, and Tudor domain. For example, in some embodiments, a histone deacetylase comprises at least one Tudor domain and two Jmj domains (e.g. one JmjN domain and one JmjC domain). In some embodiments, a histone demethylase is a lysine-specific histone demethylase. Non-limiting examples of lysine-specific histone demethylases include KDM4A, KDM4B, KDM4C, KDM4D, KDM6A, KDM6B, and PHF2. In some embodiments, an epigenetic modulator of DUX4 is a histone demethylase inhibitor.

As used herein, the term "bromodomain-containing protein" refers to a protein that has a bromodomain that recognizes monoacetylated lysine residues. Generally, bromodomain-containing (BRD) proteins bind to acetylated histones and, in some embodiments, mediate chromatin remodeling. In some embodiments, BRD proteins comprise at least one bromodomain (e.g., 1, 2, 3, 4, 5, or more bromodomains) and an Extra-Terminal (ET) domain. Non-limiting examples of BRD proteins include BRD2, BRD3, BRD4, BRDT, BRPF1, BRPF3, BPTF, BAZ1A, BAZ1B, and BAZ2A. In some embodiments, an epigenetic modulator of DUX4 is a BRD protein inhibitor.

As used herein, the term "actin-dependent regulator of chromatin" refers to a protein that is a member of the SWI/SNF Related Matrix Associated Actin Dependent Regulator of Chromatin family. Generally, members of the SWI/SNF protein family comprise a helicase domain and am ATPase domain and function to regulate transcription of certain genes by altering chromatin structure. In some embodiments, an actin-dependent regulator of chromatin further comprises one or more Swi3, Ada2, N-Cor, and TFIIIB (SANT) domains. In some embodiments, one or more actin-dependent regulators of chromatin are present in the chromatin remodeling and splicing factor (RSF) complex. Non-limiting examples of actin-dependent regulators of chromatin include SMARCA5, SMARCB1, SMARCA4, SMARCC1, SMARCC2, SMARCD1, SMARCD2, and SMARCD3. In some embodiments, an epigenetic modulator of DUX4 is an actin-dependent regulator of chromatin inhibitor.

As used herein, the term "histone methyltransferase" refers to an enzyme that catalyzes the transfer of at least one methyl group (e.g., 1, 2, 3, or more methyl groups) to lysine and/or arginine residues of a histone protein. Generally, histone methyltransferase enzymes are characterized as either lysine-specific or arginine-specific methyltransferases.

In some embodiments, an epigenetic modulator of DUX4 is an inhibitor of a lysine-specific methyltransferase. There are two families of lysine-specific methyltransferases: SET domain-containing methyltransferases and non-SET domain-containing methyltransferases.

Examples of lysine-specific histone methyltransferases include, but are not limited to, ASH1L, DOT1L, EHMT1, EHMT2, EZH1, EZH2, MLL, MLL2, MLL3, MLL4, MLL5, NSD1, PRDM1, KMT2A, KMT2C, KMT2E, SET, SETBP1, SETD1A, SETD2, SETD3, SETD4, SETD5, SETD6, SETD7, SETD9, SETD1B, SMYD1, SMYD2, SMYD3, SMYD4, SMYD5, SUV39H1, SUV39H2, SUV420H1, and SUV420H2. In some embodiments, an epigenetic modulator of DUX4 is a lysine-specific methyltransferase inhibitor.

In some embodiments, an epigenetic modulator of DUX4 is an inhibitor of an arginine-specific methyltransferase. Arginine-specific methyltransferases, also referred to as PRMTs, are generally classified into two groups. One group of PRMTs comprising PRMT1, PRMT3, CARM1, PRMT4, and Rmt1/Hmt1 produce monomethylarginine and asymmetric dimethylarginine residues. A second group of PRMTs comprising JBP1 and PRMT5 produces monomethyl or symmetric dimethylarginine residues. In some embodiments, an epigenetic modulator of DUX4 is an arginine-specific methyltransferase inhibitor.

In some embodiments, an epigenetic modulator of DUX4 is an inhibitor of a kinase (e.g. a serine-threonine kinase, for example NEK6), deacetylase enzyme (e.g., a histone deacetylase, for example HDAC1), splicing factor protein (e.g., a member of the splicing factor 3b protein complex, for example SF3B1), polymerase (e.g., PARP1, PARP2, PARP3, etc.), ligase (e.g., UFL1), hydrolase (e.g., BAP1), peptidase (e.g., a ubiquitin specific peptidase, for example USP3, USP7, USP16, USP21, or USP22), or a protease (e.g., a histone deubiquitinase, for example MYSM1). In some embodiments, an epigenetic modulator of DUX4 is an inhibitor of any one of the foregoing proteins (e.g., a kinase inhibitor, a deacetylase enzyme inhibitor, a splicing factor protein inhibitor, a polymerase inhibitor, a ligase inhibitor, a hydrolase inhibitor, a peptidase inhibitor, or a protease inhibitor).

Aspects of the invention relate to the discovery that inhibition of certain chromatin modifiers results in reduction in DUX4 gene expression and/or reduction of DUX4 protein (e.g., DUX4-fl) protein production. As used herein, the term "inhibitor" refers to any agent that reduces (e.g., prevents) activity or expression of a target molecule or gene (e.g., a chromatin modifier of DUX4). An inhibitor can be a nucleic acid (e.g., an interfering RNA), peptide, protein, polypeptide (e.g., antibody), small molecule, or any combination of the foregoing.

Aspects of the disclosure are based, in part, on the discovery that certain inhibitors (e.g., certain indirect inhibitors) of DUX4 gene expression inhibit myogenesis or myo-differentiation of cells, and may therefore not be suitable for treatment of FSHD. For example, in some embodiments, the small molecule JQ1 inhibits not only DUX4 gene expression but also TRIM43 and ZSCAN4 expression, and alters the kinetics of myogenic differentiation. JQ1 is a selective inhibitor of the BET family of bromodomain proteins. Analogues of JQ1 have are also known in the art, for example as described by Syeda et al. (2015) *Tetrahedron Letters* 56(23):3454-3457. Accordingly, in some embodiments, an epigenetic modulator of DUX4 gene expression as described by the disclosure does not inhibit myogenesis or myodifferentiation of cells. In some embodiments, an epigenetic modulator of DUX4 gene expression is not JQ1 or an analog of JQ1.

Certain indirect inhibitors of DUX4 gene expression (e.g., JQ1) have also been observed to cause aberrant expression of myogenic regulatory factors, such as myogenin (Myog), MyoD, myosin heavy chain (MyHC), and myostatin (Myost). Thus, in some embodiments, epigenetic modulators of DUX4 expression as described by the disclosure do not inhibit myogenic regulatory genes (e.g. Myog, MyoD, MyHC, Myost, etc.). In some embodiments, inhibition of a myogenic regulatory gene or genes is a reduction in expression of the gene or genes in a cell treated with an inhibitor of DUX4 gene expression relative to expression of the gene or genes in a cell that has not been treated with an inhibitor of DUX4 gene expression. In some embodiments, the reduction of expression of the gene or genes is about 10%, about 20%, about 30%, about 40%, about 50%, about 60%, about 70%, about 80%, about 90%, or about 99% less than the expression of the gene or genes in a cell that has not been treated with an inhibitor of DUX4 expression.

In some embodiments, an epigenetic modulator of DUX4 gene expression is a selective inhibitor. As used herein, a "selective inhibitor" or an inhibitor that is said to "selectively inhibit" refers to an inhibitor that preferentially inhibits activity or expression of a target molecule of a particular class compared with other molecules of the class. In some embodiments, a selective inhibitor of a target molecule of a particular class has half maximal inhibitory concentration (IC50) relative to the target molecule that is at least 2-fold, at least 4-fold, at least 8-fold, at least 10-fold, at least 20-fold, at least 30-fold, at least 40-fold, or at least 50-fold lower than the IC50 relative to one or more other members of the class. A selective inhibitor can be an inhibitor of: a methyltransferase (e.g., DNA methyltransferase or histone methyltransferase, such as a lysine-specific methyltransferase or an arginine-specific methyltransferase), a BRD protein, a histone demethylase, or an actin-dependent regulator of chromatin (e.g., component of chromatin structure remodeling complex (RSC)).

In some embodiments, a selective inhibitor selectively inhibits a histone demethylase. In some embodiments, a selective inhibitor of KDM4C, which is a lysine-specific histone demethylase, has half maximal inhibitory concentration (IC50) relative to KDM4C that is at least 2-fold, at least 4-fold, at least 8-fold, at least 10-fold, at least 20-fold, at least 30-fold, at least 40-fold, or at least 50-fold lower than the IC50 relative to one or more other histone demethylases.

In some embodiments, a selective inhibitor of KDM4A, which is a lysine-specific histone demethylase, has half maximal inhibitory concentration (IC50) relative to KDM4A that is at least 2-fold, at least 4-fold, at least 8-fold, at least 10-fold, at least 20-fold, at least 30-fold, at least 40-fold, or at least 50-fold lower than the IC50 relative to one or more other histone demethylases.

In some embodiments, a selective inhibitor of KDM4B, which is a lysine-specific histone demethylase, has half maximal inhibitory concentration (IC50) relative to KDM4B that is at least 2-fold, at least 4-fold, at least 8-fold, at least 10-fold, at least 20-fold, at least 30-fold, at least 40-fold, or at least 50-fold lower than the IC50 relative to one or more other histone demethylases.

In some embodiments, a selective inhibitor of KDM4D, which is a lysine-specific histone demethylase, has half maximal inhibitory concentration (IC50) relative to KDM4D that is at least 2-fold, at least 4-fold, at least 8-fold, at least 10-fold, at least 20-fold, at least 30-fold, at least 40-fold, or at least 50-fold lower than the IC50 relative to one or more other histone demethylases.

In some embodiments, a selective inhibitor of KDM6A, which is a lysine-specific histone demethylase, has half maximal inhibitory concentration (IC50) relative to KDM6A that is at least 2-fold, at least 4-fold, at least 8-fold, at least 10-fold, at least 20-fold, at least 30-fold, at least 40-fold, or at least 50-fold lower than the IC50 relative to one or more other histone demethylases.

In some embodiments, a selective inhibitor of KDM6B, which is a lysine-specific histone demethylase, has half maximal inhibitory concentration (IC50) relative to KDM6B that is at least 2-fold, at least 4-fold, at least 8-fold, at least 10-fold, at least 20-fold, at least 30-fold, at least 40-fold, or at least 50-fold lower than the IC50 relative to one or more other histone demethylases.

In some embodiments, a selective inhibitor of PHF2, which is a lysine-specific histone demethylase, has half maximal inhibitory concentration (IC50) relative to PHF2 that is at least 2-fold, at least 4-fold, at least 8-fold, at least 10-fold, at least 20-fold, at least 30-fold, at least 40-fold, or at least 50-fold lower than the IC50 relative to one or more other histone demethylases.

In some embodiments, a selective inhibitor selectively inhibits a histone methyltransferase. In some embodiments, a selective inhibitor of CARM1, which is an arginine-specific histone methyltransferase, has half maximal inhibitory concentration (IC50) relative to CARM1 that is at least 2-fold, at least 4-fold, at least 8-fold, at least 10-fold, at least 20-fold, at least 30-fold, at least 40-fold, or at least 50-fold lower than the IC50 relative to one or more lysine-specific histone methyltransferases.

In some embodiments, a selective inhibitor of ASH1L, which is a lysine-specific histone methyltransferase, has half maximal inhibitory concentration (IC50) relative to ASH1L that is at least 2-fold, at least 4-fold, at least 8-fold, at least 10-fold, at least 20-fold, at least 30-fold, at least 40-fold, or at least 50-fold lower than the IC50 relative to one or more lysine-specific histone methyltransferases.

In some embodiments, a selective inhibitor of DOT1L, which is a lysine-specific histone methyltransferase, has half maximal inhibitory concentration (IC50) relative to DOT1L that is at least 2-fold, at least 4-fold, at least 8-fold, at least 10-fold, at least 20-fold, at least 30-fold, at least 40-fold, or at least 50-fold lower than the IC50 relative to one or more lysine-specific histone methyltransferases.

In some embodiments, a selective inhibitor of KMT2A, which is a lysine-specific histone methyltransferase, has half maximal inhibitory concentration (IC50) relative to KMT2A that is at least 2-fold, at least 4-fold, at least 8-fold, at least 10-fold, at least 20-fold, at least 30-fold, at least 40-fold, or at least 50-fold lower than the IC50 relative to one or more lysine-specific histone methyltransferases.

In some embodiments, a selective inhibitor of KMT2C, which is a lysine-specific histone methyltransferase, has half maximal inhibitory concentration (IC50) relative to KMT2C that is at least 2-fold, at least 4-fold, at least 8-fold, at least 10-fold, at least 20-fold, at least 30-fold, at least 40-fold, or at least 50-fold lower than the IC50 relative to one or more lysine-specific histone methyltransferases.

In some embodiments, a selective inhibitor of KMT2E, which is a lysine-specific histone methyltransferase, has half maximal inhibitory concentration (IC50) relative to KMT2E that is at least 2-fold, at least 4-fold, at least 8-fold, at least 10-fold, at least 20-fold, at least 30-fold, at least 40-fold, or at least 50-fold lower than the IC50 relative to one or more lysine-specific histone methyltransferases.

In some embodiments, a selective inhibitor of PRMT1, which is a lysine-specific histone methyltransferase, has half maximal inhibitory concentration (IC50) relative to PRMT1 that is at least 2-fold, at least 4-fold, at least 8-fold, at least 10-fold, at least 20-fold, at least 30-fold, at least 40-fold, or at least 50-fold lower than the IC50 relative to one or more lysine-specific histone methyltransferases.

In some embodiments, a selective inhibitor of SETD1A, which is a lysine-specific histone methyltransferase, has half maximal inhibitory concentration (IC50) relative to SETD1A that is at least 2-fold, at least 4-fold, at least 8-fold, at least 10-fold, at least 20-fold, at least 30-fold, at least 40-fold, or at least 50-fold lower than the IC50 relative to one or more lysine-specific histone methyltransferases.

In some embodiments, a selective inhibitor of SETD1B, which is a lysine-specific histone methyltransferase, has half maximal inhibitory concentration (IC50) relative to SETD1B that is at least 2-fold, at least 4-fold, at least 8-fold, at least 10-fold, at least 20-fold, at least 30-fold, at least 40-fold, or at least 50-fold lower than the IC50 relative to one or more lysine-specific histone methyltransferases.

In some embodiments, a selective inhibitor of SMYD3, which is a lysine-specific histone methyltransferase, has half maximal inhibitory concentration (IC50) relative to SMYD3 that is at least 2-fold, at least 4-fold, at least 8-fold, at least 10-fold, at least 20-fold, at least 30-fold, at least 40-fold, or at least 50-fold lower than the IC50 relative to one or more lysine-specific histone methyltransferases.

In some embodiments, a selective inhibitor selectively inhibits a BRD protein. In some embodiments, a selective inhibitor of BRD2, has half maximal inhibitory concentration (IC50) relative to BRD2 that is at least 2-fold, at least 4-fold, at least 8-fold, at least 10-fold, at least 20-fold, at least 30-fold, at least 40-fold, or at least 50-fold lower than the IC50 relative to one or more BRD proteins.

In some embodiments, a selective inhibitor of BRD3, has half maximal inhibitory concentration (IC50) relative to BRD3 that is at least 2-fold, at least 4-fold, at least 8-fold, at least 10-fold, at least 20-fold, at least 30-fold, at least 40-fold, or at least 50-fold lower than the IC50 relative to one or more BRD proteins.

In some embodiments, a selective inhibitor of BRDT, has half maximal inhibitory concentration (IC50) relative to BRDT that is at least 2-fold, at least 4-fold, at least 8-fold, at least 10-fold, at least 20-fold, at least 30-fold, at least 40-fold, or at least 50-fold lower than the IC50 relative to one or more BRD proteins.

In some embodiments, a selective inhibitor of BRPF1, has half maximal inhibitory concentration (IC50) relative to BRPF1 that is at least 2-fold, at least 4-fold, at least 8-fold, at least 10-fold, at least 20-fold, at least 30-fold, at least 40-fold, or at least 50-fold lower than the IC50 relative to one or more BRD proteins.

In some embodiments, a selective inhibitor of BRPF3, has half maximal inhibitory concentration (IC50) relative to BRPF3 that is at least 2-fold, at least 4-fold, at least 8-fold, at least 10-fold, at least 20-fold, at least 30-fold, at least 40-fold, or at least 50-fold lower than the IC50 relative to one or more BRD proteins.

In some embodiments, a selective inhibitor of BRPTF, has half maximal inhibitory concentration (IC50) relative to BRPTF that is at least 2-fold, at least 4-fold, at least 8-fold, at least 10-fold, at least 20-fold, at least 30-fold, at least 40-fold, or at least 50-fold lower than the IC50 relative to one or more BRD proteins.

In some embodiments, a selective inhibitor of BAZ1A, has half maximal inhibitory concentration (IC50) relative to BAZ1A that is at least 2-fold, at least 4-fold, at least 8-fold, at least 10-fold, at least 20-fold, at least 30-fold, at least 40-fold, or at least 50-fold lower than the IC50 relative to one or more BRD proteins.

In some embodiments, a selective inhibitor of BAZ1B, has half maximal inhibitory concentration (IC50) relative to BAZ1B that is at least 2-fold, at least 4-fold, at least 8-fold, at least 10-fold, at least 20-fold, at least 30-fold, at least 40-fold, or at least 50-fold lower than the IC50 relative to one or more BRD proteins.

In some embodiments, a selective inhibitor of BAZ2A, has half maximal inhibitory concentration (IC50) relative to BAZ2A that is at least 2-fold, at least 4-fold, at least 8-fold, at least 10-fold, at least 20-fold, at least 30-fold, at least 40-fold, or at least 50-fold lower than the IC50 relative to one or more BRD proteins.

In some embodiments, a selective inhibitor selectively inhibits an actin-dependent regulator of chromatin (e.g., SMARCA5, SMARCB1). In some embodiments, a selective inhibitor of SMARCA5, has half maximal inhibitory concentration (IC50) relative to SMARCA5 that is at least 2-fold, at least 4-fold, at least 8-fold, at least 10-fold, at least 20-fold, at least 30-fold, at least 40-fold, or at least 50-fold lower than the IC50 relative to one or more actin-dependent regulators of chromatin. In some embodiments, a selective inhibitor of SMARCB1, has half maximal inhibitory concentration (IC50) relative to SMARCB1 that is at least 2-fold, at least 4-fold, at least 8-fold, at least 10-fold, at least 20-fold, at least 30-fold, at least 40-fold, or at least 50-fold lower than the IC50 relative to one or more actin-dependent regulators of chromatin.

In some embodiments, an epigenetic modulator of DUX4 is an interfering RNA. Examples of interfering RNA include, but are not limited to double stranded RNA (dsRNA), siRNA, shRNA, miRNA, and antisense oligonucleotide (ASO). Inhibitory oligonucleotides may interfere with gene expression, transcription and/or translation. Generally, inhibitory oligonucleotides bind to a target polynucleotide via a region of complementarity. For example, binding of inhibitory oligonucleotide to a target polynucleotide can trigger RNAi pathway-mediated degradation of the target polynucleotide (in the case of dsRNA, siRNA, shRNA, etc.), or can block the translational machinery (e.g., antisense oligonucleotides). Inhibitory oligonucleotides can be single-stranded or double-stranded. In some embodiments, inhibitory oligonucleotides are DNA or RNA. In some embodiments, the inhibitory oligonucleotide is selected from the group consisting of: antisense oligonucleotide, siRNA, shRNA and miRNA. In some embodiments, inhibitory oligonucleotides are modified nucleic acids.

The term "nucleotide analog" or "altered nucleotide" or "modified nucleotide" refers to a non-standard nucleotide, including non-naturally occurring ribonucleotides or deoxyribonucleotides. In some embodiments, nucleotide analogs are modified at any position so as to alter certain chemical properties of the nucleotide yet retain the ability of the nucleotide analog to perform its intended function. Examples of positions of the nucleotide which may be derivitized include the 5 position, e.g., 5-(2-amino)propyl uridine, 5-bromo uridine, 5-propyne uridine, 5-propenyl uridine, etc.; the 6 position, e.g., 6-(2-amino)propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; 0- and N-modified (e.g., alkylated, e.g., N6-methyl adenosine, or as otherwise known in the art) nucleotides; and other heterocyclically modified nucleotide analogs such as those described in Herdewijn, Antisense Nucleic Acid Drug Dev., 2000 Aug. 10(4):297-310.

Nucleotide analogs may also comprise modifications to the sugar portion of the nucleotides. For example the 2' OH— group may be replaced by a group selected from H, OR, R, F, Cl, Br, I, SH, SR, $NH_2$, NHR, $NR_2$, COOR, or OR, wherein R is substituted or unsubstituted $C_1$-$C_6$ alkyl, alkenyl, alkynyl, aryl, etc. Other possible modifications include those described in U.S. Pat. Nos. 5,858,988, and 6,291,438. A locked nucleic acid (LNA), often referred to as inaccessible RNA, is a modified RNA nucleotide. The ribose moiety of an LNA nucleotide is modified with an extra bridge connecting the 2' oxygen and 4' carbon.

The phosphate group of the nucleotide may also be modified, e.g., by substituting one or more of the oxygens of the phosphate group with sulfur (e.g., phosphorothioates), or by making other substitutions which allow the nucleotide to perform its intended function such as described in, for example, Eckstein, Antisense Nucleic Acid Drug Dev. 2000 Apr. 10(2):117-21, Rusckowski et al. Antisense Nucleic Acid Drug Dev. 2000 Oct. 10(5):333-45, Stein, Antisense Nucleic Acid Drug Dev. 2001 Oct. 11(5): 317-25, Vorobjev et al. Antisense Nucleic Acid Drug Dev. 2001 Apr. 11(2): 77-85, and U.S. Pat. No. 5,684,143. Certain of the above-referenced modifications (e.g., phosphate group modifications) preferably decrease the rate of hydrolysis of, for example, polynucleotides comprising said analogs in vivo or in vitro. In some embodiments, the inhibitory oligonucleotide is a modified inhibitory oligonucleotide. In some embodiments, the modified inhibitory oligonucleotide comprises a locked nucleic acid (LNA), phosphorothioate backbone, and/or a 2'-OMe modification. Table 1 below provides examples of interfering RNA that are modulators of DUX4 expression.

TABLE 1

Examples of Interfering RNA for Modulating DUX4 expression

| Gene | shRNA sequences | Target Gene | SEQ ID NO: |
|---|---|---|---|
| KDM4C | (PJ73) CCGGGCCTCTGACATGCGATTTGAACTCGAGTT CAAATCGCATGTCAGAGGCTTTTT | NC_000009.12 | 1 |
|  | (PJ74) CCGGGCAGAGAGTAATGGTGTGTTACTCGAGTA ACACACCATTACTCTCTGCTTTTT |  | 2 |
|  | (PJ75) CCGGGCCCAAGTCTTGGTATGCTATCTCGAGAT AGCATACCAAGACTTGGGCTTTTT |  | 3 |
| ASH1L | (PJ1) CCGGCGACATAAACTTGACATCTTTCTCGAGAA AGATGTCAAGTTTATGTCGTTTTT | NC_000001.11 | 4 |
|  | (PJ2) CCGGCCTGCCAAATACCATAAGAAACTCGAGTT TCTTATGGTATTTGGCAGGTTTTT |  | 5 |
|  | (PJ3) CCGGCGTACTTTGTTTATCCCAGAACTCGAGTTC TGGGATAAACAAAGTACGTTTTT |  | 6 |
| SMARCA5 | (PJ195) CCGGGTTCTTTAATTTACGGGTCTTCTCGAGAAG ACCCGTAAATTAAAGAACTTTTT | NC_000004.12 | 7 |
|  | (PJ196) CCGGCCGGGCAAATAGATTCGAGTACTCGAGTA CTCGAATCTATTTGCCCGGTTTTT |  | 8 |

TABLE 1-continued

Examples of Interfering RNA for Modulating DUX4 expression

| Gene | shRNA sequences | Target Gene | SEQ ID NO: |
|---|---|---|---|
| BAZ1A | (PJ152)<br>CCGGGCGATGAAGAAGAAGGTCAAACTCGAGT<br>TTGACCTTCTTCTTCATCGCTTTTTG | NC_000014.9 | 9 |
| BRD2 | (PJ11)<br>CCGGCCCTTTGCTGTGACACTTCTTCTCGAGAAG<br>AAGTGTCACAGCAAAGGGTTTTT | NC_000006.12 | 10 |
|  | (PJ12)<br>CCGGGCCCTCTTTACGTGATTCAAACTCGAGTTT<br>GAATCACGTAAAGAGGGCTTTTT |  | 11 |

Gene Editing Molecules

Aspects of the disclosure relate to the discovery that, in some embodiments, gene editing complexes (e.g., gene editing molecules) are useful as epigenetic modulators for inhibiting DUX4 gene expression. Thus, in some aspects, the disclosure provides a method for inhibiting DUX4 gene expression in a cell, the method comprising: contacting the cell with an effective amount of a recombinant gene editing complex, wherein the gene editing complex inhibits expression of a lysine-specific demethylase, a BRD protein, a methyltransferase, or a chromatin remodeling protein in the cell.

As used herein, "gene editing complex" refers to a biologically active molecule (e.g., a protein, one or more proteins, a nucleic acid, one or more nucleic acids, or any combination of the foregoing) configured for adding, disrupting or changing genomic sequences (e.g., a gene sequence), for example by causing a double stranded break (DSB) in a target DNA, or for inhibiting transcription of a target DNA sequence (e.g., using one or more components of a CRISPR/Cas system or similar system). Examples of gene editing complexes include but are not limited to Transcription Activator-like Effector Nucleases (TALENs), Zinc Finger Nucleases (ZFNs), engineered meganuclease re-engineered homing endonucleases, the CRISPR/Cas system, and meganucleases (e.g., Meganuclease I-SceI). In some embodiments, a gene editing complex comprises proteins or molecules (e.g., components) related to the CRISPR/Cas system, including but not limited to Cas9, Cas6, dCas9, Cpf1, CRISPR RNA (crRNA), trans-activating crRNA (tracrRNA), and variants thereof.

As used herein, the terms "endonuclease" and "nuclease" refer to an enzyme that cleaves a phosphodiester bond or bonds within a polynucleotide chain. Nucleases may be naturally occurring or genetically engineered. Genetically engineered nucleases are particularly useful for genome editing and are generally classified into four families: zinc finger nucleases (ZFNs), transcription activator-like effector nucleases (TALENs), meganucleases (e.g., engineered meganucleases) and CRISPR-associated proteins (Cas nucleases). In some embodiments, the nuclease is a ZFN. In some embodiments, the ZFN comprises a FokI cleavage domain. In some embodiments, the ZFN comprises Cys2His2 fold group. In some embodiments, the nuclease is a TALEN. In some embodiments, the TALEN comprises a FokI cleavage domain. In some embodiments, the nuclease is a meganuclease. Examples of meganucleases include but are not limited to I-SceI, I-CreI, I-DmoI, and combinations thereof (e.g., E-DreI, DmoCre).

The term "CRISPR" refers to "clustered regularly interspaced short palindromic repeats", which are DNA loci containing short repetitions of base sequences. CRISPR loci form a portion of a prokaryotic adaptive immune system that confers resistance to foreign genetic material. Each CRISPR loci is flanked by short segments of "spacer DNA", which are derived from viral genomic material. In the Type II CRISPR system, spacer DNA hybridizes to transactivating RNA (tracrRNA) and is processed into CRISPR-RNA (crRNA) and subsequently associates with CRISPR-associated nucleases (Cas nucleases) to form complexes that recognize and degrade foreign DNA. In certain embodiments, the nuclease is a CRISPR-associated nuclease (Cas nuclease). Examples of CRISPR nucleases include, but are not limited to Cas9, dCas9, Cas6, Cpf1, and variants thereof. In some embodiments, the nuclease is Cas9. In some embodiments, the Cas9 is derived from the bacteria Streptococcus pyogenes (e.g., SpCas9) or Staphylococcus aureus (e.g., SaCas9, for example SEQ ID NO: 28). In some embodiments, a Cas protein is modified (e.g. genetically engineered) to lack nuclease activity. For example, dead Cas9 (dCas9) protein binds to a target locus but does not cleave said locus. In some embodiments, a dCas9 protein comprises the sequence set forth in SEQ ID NO: 31. In some embodiments, a Cas protein or variant thereof does not exceed the packaging capacity of a viral vector, such as a lentiviral vector or an adeno-associated virus (AAV) vector, for example as described by Ran et al. (2015) Nature. 520(7546); 186-91. For example, in some embodiments, a nucleic acid encoding a Cas protein is less than about 4.6 kb in length.

Aspects of the disclosure relate to the use of CRISPR-mediated regulation of transcription, such as CRISPR interference, for the reduction (e.g. silencing) of DUX4 expression. For example, in some embodiments, a catalytically dead Cas9 protein (e.g., dead Cas9, "dCas9") is fused (e.g., covalently bound) to a transcriptional regulator domain to modulate (e.g., inhibit) expression of a target gene (e.g., a regulatory factor of DUX4 gene expression, e.g., chromatin modifiers such as KDM4C, ASH1L, BRD2, BAZ1A, SMARCA5, etc.), as described by Qi et al. (2013) Cell. 152(5); 1173-1183 and Gilbert et al. (2013) Cell. 154(2); 442-451. In some embodiments, dCas9 comprises a sequence set forth in SEQ ID NO: 31. Without wishing to be bound by any particular theory, dCas9 (or another catalytically dead Cas protein) mediates transcriptional repression, in some embodiments, by sterically hindering the binding of transcriptional machinery (e.g., a RNA polymerase complex) to a target sequence.

In some embodiments, a CRISPR Cas protein (e.g., dCas9) is fused to a transcriptional regulator domain. As used herein a "transcriptional regulator domain" is a protein domain that catalyzes structural or chemical changes in a chromatin molecule that results in altered transcriptional activity (e.g., transcriptional activation or transcriptional repression). In some embodiments, the transcriptional regulator domain is a transcriptional repressor domain. In some embodiments, the repressive domain comprises a Kruppel associated box domain (KRAB domain). Non-limiting examples of KRAB domains include KOX1 KRAB domain, KOX8 KRAB domain, ZNF43 KRAB domain, and ZNF184 KRAB domain. In some embodiments, the KRAB domain is a KOX1 KRAB domain. In some embodiments, the gene editing protein comprises a sequence set forth in SEQ ID NO: 29 or SEQ ID NO: 30. Further non-limiting examples of repressive domains include Chromo Shadow (CS) domain (e.g., CS domain of HP1α) and WRPW domain (e.g., WRPW domain of Hes1).

In some embodiments, the transcriptional regulator domain is a transcriptional activator domain. In some embodiments, the transcriptional activator domain comprises a transcriptional activation domain of Herpes simplex virus, such as VP16, or a variant thereof. Generally, a transcription factor may contain multiple activation domains, for example as described by Beerli et al. (1998) *Proc. Natl. Acad. Sci. U.S.A.* 95(25); 14628-33. Accordingly, in some embodiments, the transcriptional activator domain comprises 2, 3, 4, 5, 6, 7, 8, 9, or 10 activation domains. In some embodiments, the transcriptional activator domain is VP64, VP96, or VP160.

In some embodiments, a Cas protein is not fused to a transcriptional regulator domain, and is capable of modulating (e.g., inhibiting) gene expression via nuclease activity (e.g., DNA cleavage). Generally, Cas9 cleaves DNA at a site targeted by the guide RNA and then repaired by either non-homologous end joining (NHEJ), which is imprecise and often results in a small insertion or deletion (InDel) that disrupts the targeted sequence, or homology directed DNA repair, which allows for the insertion of a changed or new DNA sequence into the genome at a specific location. Without wishing to be bound by any particular theory, DNA cleavage by a Cas protein and subsequent repair introduce modifications into a target DNA sequence that may adversely affect (e.g., inhibit) gene expression. Accordingly, in some aspects, the disclosure relates to a gene editing complex comprising a functional nuclease and a guide RNA that hybridizes to and/or is complementary with a gene encoding a regulatory factor of DUX4 gene expression (e.g., KDM4C, ASH1L, BAZ1A, BRD2, SMARCA5, etc.) that is capable of inhibiting expression of the factor thus inhibiting expression of DUX4 in a subject (e.g., a cell of a subject).

For the purpose of genome editing, the CRISPR system can be modified to combine the tracrRNA and crRNA in to a single guide RNA (sgRNA) or just (gRNA). As used herein, the terms "guide RNA", "gRNA", and "sgRNA" refer to a polynucleotide sequence that is complementary to a target sequence in a cell and associates with a Cas nuclease, thereby directing the Cas nuclease to the target sequence. In some embodiments, a gRNA (e.g., sgRNA) ranges between 1 and 30 nucleotides in length. In some embodiments, a gRNA (e.g., sgRNA) ranges between 5 and 25 nucleotides in length. In some embodiments, a gRNA (e.g., sgRNA) ranges between 10 and 22 nucleotides in length. In some embodiments, a gRNA (e.g., sgRNA) ranges between 14 and 24 nucleotides in length. In some embodiments, a Cas protein and a guide RNA (e.g., sgRNA) are expressed from the same vector. In some embodiments, a Cas protein and a guide RNA (e.g., sgRNA) are expressed from separate vectors (e.g., two or more vectors). Without wishing to be bound by any particular theory, a guide RNA (e.g., a gRNA or sgRNA) hybridizes (e.g., binds specifically by Watson-Crick base pairing) to a target sequence and thus directs the CRISPR/Cas protein to the target sequence. In some embodiments, a guide RNA hybridizes to (e.g., targets) a gene (e.g., a nucleic acid sequence) encoding a chromatin modifier of DUX4. In some embodiments, a guide strand hybridizes to a gene encoding a histone demethylase (e.g., lysine demethylase enzyme), histone methyltransferase, histone deacetylase, histone acetyltransferase, bromodomain-containing protein, kinase (e.g., kinase that phosphorylates histone proteins), or an actin-dependent regulator of chromatin.

In some embodiments, a guide strand hybridizes to a gene (e.g., a nucleic acid sequence) encoding a histone demethylase. In some embodiments, the guide strand hybridizes to a lysine-specific histone demethylase, such as KDM4A, KDM4B, KDM4C, KDM4D, KDM6A, KDM6B, or PHF2. In some embodiments, the guide strand comprises a sequence set forth by SEQ ID NO: 12 (CGT-TACCGGGGTGGAGCCTCGGAAT; PAM in bold) or SEQ ID NO: 13 (CTTGCCCGGAAGCGCTGGCTGGGGT; PAM in bold).

In some embodiments, a guide strand hybridizes to a gene (e.g., a nucleic acid sequence) encoding a BRD protein, such as BRD2, BRD3, BRD4, BRDT, BRPF1, BRPF3, BPTF, BAZ1A, BAZ1B, or BAZ2A. In some embodiments, the guide strand comprises a sequence set forth by SEQ ID NO: 14 ( GCCAAAGCAGGGAAACGGGAGGGGT; PAM in bold ). In some embodiments, the guide strand comprises a sequence set forth by SEQ ID NO: 15 (ATACAAGT-TAAATCGTAATTGGAAT; PAM in bold) or SEQ ID NO: 16 (TTGACTACACGATGGGAAAAGGGAT; PAM in bold).

In some embodiments, a guide strand hybridizes to a gene (e.g., a nucleic acid sequence) encoding an actin-dependent regulator of chromatin, such as SMARCA5, SMARCB1, SMARCA4, SMARCC1, SMARCC2, SMARCD1, SMARCD2, or SMARCD3. In some embodiments, the guide strand comprises a sequence set forth by SEQ ID NO: 17 (AAAAC<u>C</u>GTGAGACTTCACTTGGGGT; PAM highlighted) or SEQ ID NO: 18 (TGTGTCTTCTGTGCCTGACAGGGGT; PAM in bold).

In some embodiments, a guide strand hybridizes to a gene (e.g., a nucleic acid sequence) encoding a lysine-specific methyltransferase, such as ASH1L, DOT1L, EHMT1, EHMT2, EZH1, EZH2, MLL, MLL2, MLL3, MLL4, MLL5, NSD1, PRDM1, KMT2A, KMT2C, KMT2E, SET, SETBP1, SETD1A, SETD2, SETD3, SETD4, SETD5, SETD6, SETD7, SETD9, SETD1B, SMYD1, SMYD2, SMYD3, SMYD4, SMYD5, SUV39H1, SUV39H2, SUV420H1, or SUV420H2. In some embodiments, the guide strand comprises a sequence set forth by SEQ ID NO: 19 ( GCCCTCACGCGTACCTTCAACGG; PAM in bold).

In some embodiments, a guide strand hybridizes to a gene (e.g., a nucleic acid sequence) encoding an arginine-specific methyltransferase, such as PRMT1, PRMT3, CARM1, PRMT4, Rmt1/Hmt1, JBP1, or PRMT5.

In some embodiments, In some embodiments, a guide strand hybridizes to a gene (e.g., a nucleic acid sequence) encoding a kinase (e.g. a serine-threonine kinase, for example NEK6), deacetylase enzyme (e.g., a histone deacetylase, for example HDAC1), splicing factor protein (e.g., a member of the splicing factor 3b protein complex, for example SF3B1), polymerase (e.g., PARP1, PARP2, PARP3, etc.), ligase (e.g., UFL1), hydrolase (e.g., BAP1), peptidase (e.g., a ubiquitin specific peptidase, for example USP3, USP7, USP16, USP21, or USP22), or a protease (e.g., a histone deubiquitinase, for example MYSM1).

Methods of Treatment

In some aspects, the disclosure provides methods for treating a subject having facioscapulohumeral muscular dystrophy (FSHD). For example, transcriptional activation of the DUX4 gene may lead to FSHD in a subject. As used herein, a "subject" is interchangeable with a "subject in need thereof", both of which may refer to a subject having FSHD, or a subject having an increased risk of developing such a disorder relative to the population at large. For example, in some embodiments, a subject has a D4Z array comprising 11 or fewer repeat units at chromosome 4q35 but does not exhibit signs or symptoms of FSHD. A subject in need thereof may be a subject having a transcriptionally active DUX4 gene (e.g., a subject expressing DUX4-fl protein). A subject can be a human, non-human primate, rat, mouse, cat, dog, or other mammal.

As used herein, the terms "treatment", "treating", and "therapy" refer to therapeutic treatment and prophylactic or preventative manipulations. The terms further include ameliorating existing symptoms, preventing additional symptoms, ameliorating or preventing the underlying causes of symptoms, preventing or reversing causes of symptoms, for example, symptoms associated with FSHD. Thus, the terms denote that a beneficial result has been conferred on a subject having FSHD, or with the potential to develop such a disorder. Furthermore, the term "treatment" is defined as the application or administration of an agent (e.g., therapeutic agent or a therapeutic composition) to a subject, or an isolated tissue or cell line from a subject, who may have a disease, a symptom of disease or a predisposition toward a disease, with the purpose to cure, heal, alleviate, relieve, alter, remedy, ameliorate, improve or affect the disease, the symptoms of disease or the predisposition toward disease.

Therapeutic agents or therapeutic compositions may include a compound in a pharmaceutically acceptable form that prevents and/or reduces the symptoms of a particular disease (e.g., FSHD). For example a therapeutic composition may be a pharmaceutical composition that prevents and/or reduces the symptoms of FSHD. It is contemplated that the therapeutic composition of the present invention will be provided in any suitable form. The form of the therapeutic composition will depend on a number of factors, including the mode of administration as described herein. The therapeutic composition may contain diluents, adjuvants and excipients, among other ingredients as described herein.

In some aspects, the disclosure provides a method for inhibiting (e.g., silencing) a transcriptionally active DUX4 gene in a cell, the method comprising: contacting the cell with an effective amount of an epigenetic modulator of DUX4, wherein the epigenetic modulator reduces DUX4 expression in the cell. In some embodiments, the cell is in vitro or ex vivo.

As used herein, "ex vivo modified cell" refers to a cell (e.g., a mammalian cell) that is removed from a subject, genetically modified (e.g., transfected or transduced with exogenous nucleic acids, or genetically reprogrammed), cultured or expanded, and optionally, returned to a subject (e.g., either the same subject, or a different subject). Generally, ex vivo modified cells are useful for autologous cell therapy, or allogeneic cell therapy. For example, cells may be removed from a subject having a disease associated with a particular genetic defect (e.g., FSHD), transfected with a gene editing complex that corrects the genetic defect (e.g. reduces expression of DUX4), and reintroduced into the subject. In another non-limiting example, cells are removed from a subject, genetically reprogrammed (e.g., dedifferentiated or transdifferentiated into muscle cells), expanded, and reintroduced into the subject.

The cell contacted with the effective amount of an epigenetic modulator of DUX4 can be any cell that has a transcriptionally active DUX4 gene. For example, the cell can be a muscle cell (e.g., a myoblast, a terminally differentiated muscle cell, a muscle satellite cell, or muscle stem cell).

A cell having a transcriptionally active DUX4 gene can also comprise a contraction of a D4Z4 repeat array at chromosome 4q35 of the DUX4 gene. The number of repeat units in the array can vary. In some embodiments, the number of repeat units in the contraction is 11 or fewer (e.g., 11, 10, 9, 8, 7, 6, 5, 4, 3, 2, 1, or 0) repeat units.

Pharmaceutical Compositions

In some aspects, the disclosure relates to pharmaceutical compositions comprising an epigenetic modulator of DUX4. In some embodiments, the composition comprises an epigenetic modulator of DUX4 and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Pharmaceutical compositions can be prepared as described below. The active ingredients may be admixed or compounded with any conventional, pharmaceutically acceptable carrier or excipient. The compositions may be sterile.

Typically, pharmaceutical compositions are formulated for delivering an effective amount of an agent (e.g., an epigenetic modulator of DUX4). In general, an "effective amount" of an active agent refers to an amount sufficient to elicit the desired biological response (e.g., transcriptional repression, such as silencing or inhibition, of the active DUX4 gene). An effective amount of an agent may vary depending on such factors as the desired biological endpoint, the pharmacokinetics of the compound, the disease being treated (e.g., FSHD), the mode of administration, and the patient.

A composition is said to be a "pharmaceutically acceptable carrier" if its administration can be tolerated by a recipient patient. Sterile phosphate-buffered saline is one example of a pharmaceutically acceptable carrier. Other suitable carriers are well-known in the art. See, for example, REMINGTON'S PHARMACEUTICAL SCIENCES, 18th Ed. (1990).

It will be understood by those skilled in the art that any mode of administration, vehicle or carrier conventionally employed and which is inert with respect to the active agent may be utilized for preparing and administering the pharmaceutical compositions of the present disclosure. Illustrative of such methods, vehicles and carriers are those described, for example, in Remington's Pharmaceutical Sciences, 4th ed. (1970), the disclosure of which is incorporated herein by reference. Those skilled in the art, having been exposed to the principles of the disclosure, will experience no difficulty in determining suitable and appropriate vehicles, excipients and carriers or in compounding the active ingredients therewith to form the pharmaceutical compositions of the disclosure.

An effective amount, also referred to as a therapeutically effective amount, of a compound (for example, an antisense nucleic acid (e.g., oligonucleotide), gene editing complex, or small molecule epigenetic modulator of DUX4) is an amount sufficient to ameliorate at least one adverse effect associated with activation (e.g., transcriptional activation), or increased expression, of the gene in a cell or in an individual in need of such modulation. In some embodiments, an effective amount is an amount sufficient to inhibit (e.g., transcriptionally repress) DUX4 gene in a cell or in an individual in need of DUX4 inhibition. The therapeutically effective amount to be included in pharmaceutical compositions depends, in each case, upon several factors, e.g., the type, size and condition of the patient to be treated, the intended mode of administration, the capacity of the patient to incorporate the intended dosage form, etc. Generally, an amount of active agent is included in each dosage form to provide from about 0.1 to about 250 mg/kg, and preferably from about 0.1 to about 100 mg/kg. One of ordinary skill in the art would be able to determine empirically an appropriate therapeutically effective amount.

Combined with the teachings provided herein, by choosing among the various active compounds and weighing factors such as potency, relative bioavailability, patient body weight, severity of adverse side-effects and selected mode of administration, an effective prophylactic or therapeutic treatment regimen can be planned which does not cause substantial toxicity and yet is entirely effective to treat the particular subject. The effective amount for any particular application can vary depending on such factors as the disease or condition being treated, the particular therapeutic agent being administered, the size of the subject, or the severity of the disease or condition. One of ordinary skill in the art can empirically determine the effective amount of a particular nucleic acid and/or other therapeutic agent without necessitating undue experimentation.

In some cases, compounds of the disclosure are prepared in a colloidal dispersion system. Colloidal dispersion systems include lipid-based systems including oil-in-water emulsions, micelles, mixed micelles, and liposomes. In some embodiments, a colloidal system of the disclosure is a liposome. Liposomes are artificial membrane vessels which are useful as a delivery vector in vivo or in vitro. It has been shown that large unilamellar vesicles (LUVs), which range in size from 0.2-4.0 µm can encapsulate large macromolecules. RNA, DNA and intact virions can be encapsulated within the aqueous interior and be delivered to cells in a biologically active form. Fraley et al. (1981) Trends Biochem Sci 6:77.

Liposomes may be targeted to a particular tissue by coupling the liposome to a specific ligand such as a monoclonal antibody, sugar, glycolipid, or protein. Ligands which may be useful for targeting a liposome to, for example, an smooth muscle cell include, but are not limited to: intact or fragments of molecules which interact with smooth muscle cell specific receptors and molecules, such as antibodies, which interact with the cell surface markers of cancer cells. Such ligands may easily be identified by binding assays well known to those of skill in the art. In still other embodiments, the liposome may be targeted to a tissue by coupling it to an antibody known in the art.

Lipid formulations for transfection are commercially available from QIAGEN, for example, as EFFECTENE™ (a non-liposomal lipid with a special DNA condensing enhancer) and SUPERFECT™ (a novel acting dendrimeric technology).

Liposomes are commercially available from Gibco BRL, for example, as LIPOFECTIN™ and LIPOFECTACE™, which are formed of cationic lipids such as N-[1-(2,3 dioleyloxy)-propyl]-N,N,N-trimethylammonium chloride (DOTMA) and dimethyl dioctadecylammonium bromide (DDAB). Methods for making liposomes are well known in the art and have been described in many publications. Liposomes also have been reviewed by Gregoriadis G (1985) Trends Biotechnol 3:235-241.

Certain cationic lipids, including in particular N-[1-(2,3 dioleoyloxy)-propyl]-N,N,N-trimethylammonium methylsulfate (DOTAP), may be advantageous when combined with the epigenetic modulators of DUX4 (e.g., interfering RNA) of the disclosure.

In some aspects of the disclosure, the use of compaction agents may also be desirable. Compaction agents also can be used alone, or in combination with, a biological or chemical/physical vector. A "compaction agent", as used herein, refers to an agent, such as a histone, that neutralizes the negative charges on the nucleic acid and thereby permits compaction of the nucleic acid into a fine granule. Compaction of the nucleic acid facilitates the uptake of the nucleic acid by the target cell. The compaction agents can be used alone, e.g., to deliver an epigenetic modulator of DUX4 in a form that is more efficiently taken up by the cell or, in combination with one or more of the above-described carriers.

Other exemplary compositions that can be used to facilitate uptake of an epigenetic modulator of DUX4 include calcium phosphate and other chemical mediators of intracellular transport, microinjection compositions, electroporation and homologous recombination compositions (e.g., for integrating a nucleic acid into a preselected location within the target cell chromosome).

The compounds may be administered alone (e.g., in saline or buffer) or using any delivery vehicle known in the art. For instance the following delivery vehicles have been described: cochleates; Emulsomes; ISCOMs; liposomes; live bacterial vectors (e.g., *Salmonella, Escherichia coli, Bacillus* Calmette-Guérin, *Shigella, Lactobacillus*); live viral vectors (e.g., Vaccinia, adenovirus, Herpes Simplex, Lentiviral); microspheres; nucleic acid vaccines; polymers (e.g., carboxymethylcellulose, chitosan); polymer rings; proteosomes; sodium fluoride; transgenic plants; virosomes; and, virus-like particles. In some embodiments, epigenetic modulators of DUX4 described by the disclosure are delivered by lentiviral vector.

The formulations of the disclosure are administered in pharmaceutically acceptable solutions, which may routinely contain pharmaceutically acceptable concentrations of salt, buffering agents, preservatives, compatible carriers, adjuvants, and optionally other therapeutic ingredients.

The term pharmaceutically-acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being commingled with the compounds of the present disclosure, and with each other, in a manner such that there is no interaction which would substantially impair the desired pharmaceutical efficiency.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

In addition to the formulations described herein, the compounds may also be formulated as a depot preparation. Such long-acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer R (1990) Science 249:1527-1533, which is incorporated herein by reference.

The compounds may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The compositions may conveniently be presented in unit dosage form and may be prepared by any of the methods well known in the art of pharmacy. All methods include the step of bringing the compounds into association with a carrier which constitutes one or more accessory ingredients. In general, the compositions are prepared by uniformly and intimately bringing the compounds into association with a liquid carrier, a finely divided solid carrier, or both, and then, if necessary, shaping the product. Liquid dose units are vials or ampoules. Solid dose units are tablets, capsules and suppositories.

Modes of Administration

The pharmaceutical compositions of the present disclosure preferably contain a pharmaceutically acceptable carrier or excipient suitable for rendering the compound or mixture administrable orally as a tablet, capsule or pill, or parenterally, intravenously, intradermally, intramuscularly or subcutaneously, or transdermally.

In some embodiments, a therapeutically effective amount of an epigenetic modulator of DUX4 is delivered to a target tissue or a target cell. In some embodiments, DUX4 (e.g., DUX4-fl) is expressed in muscle cells of a subject having FSHD. Thus, in some embodiments, an effective amount of epigenetic modulator of DUX4 is delivered to the muscle cells of a subject. In some embodiments, the muscle cells are terminally differentiated muscle cells. Examples of differentiated muscle cells include myocytes and myotubes.

The pharmaceutical compositions containing an epigenetic modulator of DUX4 and/or other compounds can be administered by any suitable route for administering medications. A variety of administration routes are available. The particular mode selected will depend, of course, upon the particular agent or agents selected, the particular condition being treated, and the dosage required for therapeutic efficacy. The methods of this disclosure, generally speaking, may be practiced using any mode of administration that is medically acceptable, meaning any mode that produces therapeutic effect without causing clinically unacceptable adverse effects. Various modes of administration are discussed herein. For use in therapy, an effective amount of the epigenetic modulator of DUX4 and/or other therapeutic agent can be administered to a subject by any mode that delivers the agent to the desired surface, e.g., systemic, intramuscular, etc.

Administering the pharmaceutical composition of the present disclosure may be accomplished by any means known to the skilled artisan. Routes of administration include but are not limited to oral, parenteral, intravenous, intramuscular, intraperitoneal, intranasal, sublingual, intratracheal, inhalation, subcutaneous, ocular, vaginal, and rectal. Systemic routes include oral and parenteral. Several types of devices are regularly used for administration by inhalation. These types of devices include metered dose inhalers (MDI), breath-actuated MDI, dry powder inhaler (DPI), spacer/holding chambers in combination with MDI, and nebulizers.

For oral administration, the compounds can be formulated readily by combining the active compound(s) with pharmaceutically acceptable carriers well known in the art. Such carriers enable the compounds of the disclosure to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present disclosure may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

Other delivery systems can include time-release, delayed release or sustained release delivery systems. Such systems can avoid repeated administrations of the compounds, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-, di-, and triglycerides; hydrogel release systems; silastic systems; peptide-based systems; wax coatings; compressed tablets using conventional binders and excipients; partially fused implants; and the like. Specific examples include, but are not limited to: (a) erosional systems in which an agent of the disclosure is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

In some embodiments, an inhibitory oligonucleotide (e.g., interfering RNA) can be delivered to the cells via an expression vector engineered to express the inhibitor oligonucleotide. An expression vector is one into which a desired sequence may be inserted, e.g., by restriction and ligation, such that it is operably joined to regulatory sequences and may be expressed as an RNA transcript. An expression vector typically contains an insert that is a coding sequence for a protein or for a inhibitory oligonucleotide such as an shRNA, a miRNA, or an miRNA. Vectors may further contain one or more marker sequences suitable for use in the identification of cells that have or have not been transformed or transfected with the vector. Markers include, for example, genes encoding proteins that increase or decrease either resistance or sensitivity to antibiotics or other compounds, genes that encode enzymes whose activities are detectable by standard assays or fluorescent proteins, etc.

As used herein, a coding sequence (e.g., protein coding sequence, miRNA sequence, shRNA sequence) and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide. It will be appreciated that a coding sequence may encode an miRNA, shRNA or miRNA.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Such 5' non-transcribed regulatory sequences will include a promoter region that includes a promoter sequence for transcriptional control of the operably joined gene. Regulatory sequences may also include enhancer sequences or upstream activator sequences as desired. The vectors of the disclosure may optionally include 5' leader or signal sequences.

In some embodiments, a virus vector for delivering a nucleic acid molecule is selected from the group consisting of adenoviruses, adeno-associated viruses, poxviruses including vaccinia viruses and attenuated poxviruses, Semliki Forest virus, Venezuelan equine encephalitis virus, retroviruses, Sindbis virus, and Ty virus-like particle. Examples of viruses and virus-like particles which have been used to deliver exogenous nucleic acids include: replication-defective adenoviruses, a modified retrovirus, a nonreplicating retrovirus, a replication defective Semliki Forest virus, canarypox virus and highly attenuated vaccinia virus derivative, non-replicative vaccinia virus, replicative vaccinia virus, Venzuelan equine encephalitis virus, Sindbis virus, lentiviral vectors and Ty virus-like particle.

Another virus useful for certain applications is the adeno-associated virus. The adeno-associated virus is capable of infecting a wide range of cell types and species and can be engineered to be replication-deficient. It further has advantages, such as heat and lipid solvent stability, high transduction frequencies in cells of diverse lineages, including hematopoietic cells, and lack of superinfection inhibition thus allowing multiple series of transductions. The adeno-associated virus can integrate into human cellular DNA in a site-specific manner, thereby minimizing the possibility of insertional mutagenesis and variability of inserted gene expression. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

In general, other useful viral vectors are based on non-cytopathic eukaryotic viruses in which non-essential genes have been replaced with the gene of interest. Non-cytopathic viruses include certain retroviruses, the life cycle of which involves reverse transcription of genomic viral RNA into DNA with subsequent proviral integration into host cellular DNA. In general, the retroviruses are replication-deficient (e.g., capable of directing synthesis of the desired transcripts, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W.H. Freeman Co., New York (1990) and Murry, E. J. Ed. "Methods in Molecular Biology," vol. 7, Humana Press, Inc., Clifton, N.J. (1991). In some embodiments, an epigenetic modulator of DUX4 (e.g., an interfering RNA or a gene editing complex) is delivered to a cell (e.g. a cell of a subject) by a lentiviral vector.

Various techniques may be employed for introducing nucleic acid molecules of the disclosure into cells, depending on whether the nucleic acid molecules are introduced in vitro or in vivo in a host. Such techniques include transfection of nucleic acid molecule-calcium phosphate precipitates, transfection of nucleic acid molecules associated with DEAE, transfection or infection with the foregoing viruses including the nucleic acid molecule of interest, liposome-mediated transfection, and the like. Other examples include: N-TER™ Nanoparticle Transfection System by Sigma-Aldrich, FectoFly™ transfection reagents for insect cells by Polyplus Transfection, Polyethylenimine "Max" by Polysciences, Inc., Unique, Non-Viral Transfection Tool by Cosmo Bio Co., Ltd., Lipofectamine™ LTX Transfection Reagent by Invitrogen, SatisFection™ Transfection Reagent by Stratagene, Lipofectamine™ Transfection Reagent by Invitrogen, FuGENE® HD Transfection Reagent by Roche Applied Science, GMP compliant in vivo-jetPEI™ transfection reagent by Polyplus Transfection, and Insect GeneJuice® Transfection Reagent by Novagen.

Screening Methods

In some aspects, the disclosure relates to methods of identifying agents that function as epigenetic modulators of DUX4. Accordingly, in some embodiments, the disclosure provides a method for identifying epigenetic modulators of DUX4, the method comprising: contacting a cell characterized by the expression of DUX4 (e.g., DUX4-fl) with a candidate agent for modulating expression or activity of a putative chromatin modifier of DUX4; detecting expression level DUX4 in the cell; and, identifying the candidate agent as an epigenetic modulator of DUX4 when the expression level of DUX4 decreases relative to a control cell after contact with the candidate agent. Exemplary candidate agents include, but are not limited to small molecules, antibodies, antibody conjugates, peptides, proteins, antisense molecules (e.g., interfering RNAs) or other nucleic acids. In some embodiments, methods described by the disclosure are useful for screening large libraries of candidate compounds (e.g., compound libraries) to identify new epigenetic modulators of DUX4. In some embodiments, compound libraries consist of candidate agents specific for a particular target nucleic acid (e.g., nucleic acid sequence) or a particular protein target, such as a histone demethylase (e.g., lysine demethylase enzyme), histone methltyransferase, histone deacetylase, histone acetyltransferase, bromodomain-containing protein, kinase (e.g., kinase that phosphorylates histone proteins), or an actin-dependent regulator of chromatin. In some embodiments, candidate agents are inhibitors of a histone demethylase (e.g., lysine demethylase enzyme), histone methltyransferase, histone deacetylase, histone acetyltransferase, bromodomain-containing protein, kinase (e.g., kinase that phosphorylates histone proteins), or an actin-dependent regulator of chromatin.

The skilled artisan recognizes several methods for contacting the cell having an activated DUX4 gene with the candidate compound. For example, automated liquid handling systems are generally utilized for high throughput drug screening. Automated liquid handling systems utilize arrays of liquid dispensing vessels, controlled by a robotic arm, to distribute fixed volumes of liquid to the wells of an assay plate. Generally, the arrays comprise 96, 384 or 1536 liquid dispensing tips. Non-limiting examples of automated liquid handling systems include digital dispensers (e.g., HP D300 Digital Dispenser) and pinning machines (e.g., MULTI-BLOT™ Replicator System, CyBio, Perkin Elmer Janus). Non-automated methods are also contemplated by the disclosure, and include but are not limited to a manual digital repeat multichannel pipette.

In some embodiments, screening methods described by the disclosure are carried out in a high throughput mode. In some embodiments, high-throughput screening is carried out in a multi-well cell culture plate. In some embodiments, the multi-well plate is plastic or glass. In some embodiments, the multi-well plate comprises an array of 6, 24, 96, 384 or 1536 wells. However, the skilled artisan recognizes that multi-well plates may be constructed into a variety of other acceptable configurations, such as a multi-well plate having a number of wells that is a multiple of 6, 24, 96, 384 or 1536. For example, in some embodiments, the multi-well plate comprises an array of 3072 wells (which is a multiple of 1536).

The expression level DUX4 in the cell can be measured by any suitable means known in the art. For example, expression level of DUX4 in a cell can be measured by a hybridization-based method. Examples of hybridization-based assays include reverse transcription polymerase chain reaction (RT-PCR), quantitative RT-PCR (qRT-PCR), Northern blot, and Southern blot. In some embodiments, the expression level DUX4 (e.g., DUX4-fl) in the cell is measured by a protein-based method. Examples of protein-based assays include, but are not limited to, Western blot, Bradford assay, Lowry protein assay, and spectroscopic methods (e.g., mass spectrometry, high pressure liquid chromatography, etc.). In some embodiments, expression level DUX4 (e.g., DUX4-fl) in the cell is determined by a cell-based method. Examples of cell-based assays include flow cytometry, fluorescent activated cell sorting (FACS), magnetic-activated cell sorting (MACS). In some embodiments, cells are modified such that DUX4 inhibition is operably linked to expression of a resistance gene, and thus inhibition (e.g., transcriptional repression) of DUX4 allows growth and selection of cells in the presence of a selection media. Additional methods of quantifying expression level DUX4 in the cell will be readily apparent to those skilled in the art.

A candidate compound can be identified as an epigenetic modulator of DUX4 if the amount of DUX4 expressed in the presence of the candidate compound is less than (e.g., reduced relative to) the amount expressed in the absence of candidate compound. The amount of DUX4 expressed in the presence of an epigenetic modulator of DUX4 can range from about 1% to about 100% less, about 5% to about 50% less (e.g., about 5%, about 10%, about 15%, about 20%, about 25%, about 30%, about 35%, about 40%, about 45%, or about 50% less), about 10% to about 40% less, or about 20% to about 30% less than the amount of DUX4 expressed in the absence of the epigenetic modulator of DUX4. In some embodiments, DUX4 is not expressed (e.g., transcriptionally inactive, or silenced) in the presence of an epigenetic modulator of DUX4 and is expressed (e.g., transcriptionally active) in the absence of an epigenetic modulator of DUX4.

EXAMPLES

Example 1

This example describes targeting the regulatory mechanism governing the aberrant increase in DUX4 transcriptions for treatment of Facioscapulohumeral muscular dystrophy (FSHD). In normal subjects (e.g., subjects not having FSHD), DUX4 expression is normally OFF. Here, the identification of regulatory factors that are causing DUX4 to be ON in muscle of subjects having FSHD is described. Such regulatory factors are, in some embodiments, targets for small molecule therapies to treat FSHD.

A screen to identify genes involved in DUX4 expression (e.g., when the expression of these genes is reduced in FSHD muscle cells, DUX4 expression also decreases) was performed. Briefly, primary differentiated myocytes derived from subjects having FSHD were treated with shRNA targeting candidate genes and the expression level of pathogenic DUX4-fl mRNA was quantified. The expression levels of other myogenic regulators (e.g., Myogenin, MyoD, MyHD) and other targets (e.g., FRG1, UTRN, and 18S) were also quantified to assess indirect effects of DUX4 knockdown. A sample screening protocol is shown below:

Example Screening Protocol

1. Expand low passage primary FSHD myoblasts.
2. Plate into 6-well plates.
3. Allow cells to reach confluence and differentiate (approximately 48 hours).
4. Infect cells with lentiviral shRNA construct and incubate for 24 hours.
5. Re-infect cells with lentiviral shRNA construct.
6. Harvest cells 4 days after second infection.
7. Extract RNA from cells and assay for expression level of DUX4-fl and other genes of interest.

A list providing non-limiting examples of candidate genes is provided in Table 2. In total, 39 candidate genes from Table 2 were screened; each candidate gene was infected with 2-3 different shRNAs, also shown in Table 2. Relative gene expression for DUX4, Myogenin, MyoD, MyHC, FRG1, UTRN, and 18S are shown in Table 3.

TABLE 2

| Locus | Name | shRNA | | SET 1-KD | SET 2-KD |
|---|---|---|---|---|---|
| TRCN0000016169 | ASH1L | PJ1 | AAD02 C 3 | x | |
| TRCN0000016168 | | PJ2 | AAD02 C 2 | x | |
| TRCN0000016172 | | PJ3 | AAD02 C 6 | | X |
| TRCN0000016818 | BPTF | PJ6 | AAD09 D 10 | | X |
| TRCN0000016819 | | PJ7 | AAD09 D 11 | | X |
| TRCN0000006308 | BRD2 | PJ11 | AAC04 H 2 | x | |
| TRCN0000006309 | | PJ12 | AAC04 H 3 | x | |
| TRCN0000006311 | | PJ14 | AAC04 H 5 | | X |
| TRCN0000021374 | BRD3 | PJ16 | AAD57 A 1 | x | |
| TRCN0000021375 | | PJ17 | AAD57 A 2 | x | |
| TRCN0000021376 | | PJ18 | AAD57 A 3 | | X |
| TRCN0000021424 | BRD4 | PJ21 | AAD57 E 3 | x | |
| TRCN0000021425 | | PJ22 | AAD57 E 4 | x | |
| TRCN0000006303 | BRDT | PJ26 | AAC04 G 9 | x | |
| TRCN0000006304 | | PJ27 | AAC04 G 10 | x | |
| TRCN0000021909 | BRPF1 | PJ31 | AAD62 H 2 | | X |
| TRCN0000021912 | | PJ32 | AAD62 H 5 | | X |
| TRCN0000021101 | BRPF3 | PJ40 | AAD53 H 4 | | X |
| TRCN0000021099 | | PJ41 | AAD53 H 2 | | X |
| TRCN0000007168 | CARM1 | PJ45 | AAC15 B 7 | x | |
| TRCN0000007167 | | PJ46 | AAC15 B 5 | x | |
| TRCN0000007169 | | PJ47 | AAC15 B 8 | | X |

TABLE 2-continued

| Locus | Name | shRNA | | SET 1-KD | SET 2-KD |
|---|---|---|---|---|---|
| TRCN0000020211 | DOT1L | PJ50 | AAD44 A 8 | | X |
| TRCN0000107760 | KDM6A | PJ55 | AAN23 C 7 | | X |
| TRCN0000107761 | | PJ56 | AAN23 C 8 | | X |
| V3LHS_301324 | KDM6B | PJ60 | 172_1333 B 3 | | X |
| V3LHS_301328 | | PJ61 | 172_1356 B 1 | | X |
| TRCN0000013493 | KDM4A | PJ62 | AAC71 E 3 | x | |
| TRCN0000013494 | | PJ63 | AAC71 E 4 | x | |
| TRCN0000018017 | KDM4B | PJ67 | AAD22 G 3 | x | |
| TRCN0000018015 | | PJ69 | AAD22 G 1 | x | |
| TRCN0000022056 | KDM4C | PJ73 | AAD64 E 5 | x | |
| TRCN0000022058 | | PJ74 | AAD64 E 7 | x | |
| TRCN0000022054 | | PJ75 | AAD64 E 3 | | X |
| TRCN0000148192 | KDM4D | PJ78 | AAQ74 F 10 | x | |
| TRCN0000147186 | | PJ79 | AAQ74 F 8 | x | |
| TRCN0000005955 | KMT2A | PJ83 | AAB99 F 3 | x | |
| TRCN0000005956 | | PJ84 | AAB99 F 4 | x | |
| TRCN0000008746 | KMT2C | PJ89 | AAC37 A 10 | | X |
| TRCN0000008744 | | PJ90 | AAC37 A 8 | | X |
| TRCN0000154711 | KMT2E | PJ94 | AAQ81 F 3 | | X |
| TRCN0000155824 | | PJ95 | AAQ81 F 5 | | X |
| TRCN0000001723 | NEK6 | PJ99 | AAB48 G 9 | | X |
| TRCN0000001724 | | PJ100 | AAB48 G 10 | | X |
| TRCN0000019184 | PHF2 | PJ104 | AAD32 F 1 | | X |
| TRCN0000019185 | | PJ105 | AAD32 F 2 | | X |
| TRCN0000035929 | PRMT1 | PJ109 | AAF20 F 6 | | X |
| TRCN0000035930 | | PJ110 | AAF20 F 7 | | X |
| TRCN0000150815 | SETD1A | PJ114 | AAR37 A 12 | | X |
| TRCN0000152242 | | PJ115 | AAR37 B 1 | | X |
| V2LHS_18585 | SETD1B | PJ119 | 172_0404 B 9 | | X |
| V3LHS_316056 | | PJ120 | 172_1039 B 1 | | X |
| TRCN0000123289 | SMYD3 | PJ121 | AAO79 C 12 | | X |
| TRCN0000123292 | | PJ122 | AAO79 D 3 | | X |
| TRCN0000013338 | BAZ1B | PJ142 | AAC69 G 4 | x | |
| TRCN0000013339 | | PJ143 | AAC69 G 5 | x | |
| TRCN0000004814 | HDAC1 | PJ147 | AAB86 C 2 | | |
| TRCN0000034279 | BAZ1A | PJ152 | AAF02 C 12 | x | |
| TRCN0000034280 | | PJ153 | AAF02 D 1 | x | |
| TRCN0000034281 | | PJ154 | AAF02 D 2 | | X |
| TRCN0000015568 | BAZ2A | PJ157 | AAC94 E 8 | x | |
| TRCN0000015569 | | PJ158 | AAC94 E 9 | x | |
| TRCN0000000075 | SF3B1 | PJ162 | AAA01 G 5 | | X |
| TRCN0000000076 | | PJ163 | AAA01 G 6 | | X |
| TRCN0000007928 | PARP1 | PJ167 | AAC25 B 9 | | |
| TRCN0000007933 | PARP2 | PJ172 | AAC25 C 2 | | |
| TRCN0000052938 | PARP3 | PJ177 | AAH09 C 12 | | |
| TRCN0000122062 | UFL1 | PJ182 | AAQ11 A 10 | | X |
| TRCN0000122630 | | PJ183 | AAQ11 A 7 | | X |
| TRCN0000010503 | SMARCB1 | PJ187 | BH-004 G 8 | x | |
| TRCN0000039583 | | PJ188 | AAF61 A 11 | | X |
| TRCN0000010504 | | PJ190 | BH-004 G 9 | x | |
| TRCN0000013213 | SMARCA5 | PJ195 | AAC68 D 5 | x | x |
| TRCN0000013214 | | PJ196 | AAC68 D 6 | x | |
| TRCN0000013215 | | PJ197 | AAC68 D 7 | | X |
| TRCN0000007370 | BAP1 | PJ200 | AAC17 F 1 | x | |
| TRCN0000007371 | | PJ201 | AAC17 F 2 | x | |
| TRCN0000007604 | USP3 | PJ205 | AAC20 C 2 | | |
| TRCN0000007608 | | PJ209 | AAC20 C 6 | | X |
| TRCN0000010845 | USP7 | PJ210 | AAB77 A 11 | | X |
| TRCN0000007594 | USP16 | TS30 | AAC20 B 4 | | X |
| TRCN0000007595 | | TS31 | AAC20 B 5 | | X |
| TRCN0000004347 | USP21 | TS6 | AAB80 E 8 | | |
| TRCN0000046924 | USP22 | TS143 | AAG41 F 7 | | |
| V3LHS_311636 | MYSM1 | TS190 | 172_1593 B 4 | | X |
| V2LHS_87333 | | TS191 | 172_0592 C 6 | | X |
| V3LHS_311640 | | TS192 | 172_1393 D 4 | | |
| TRCN control | TRCN control | | | X | X |
| No virus mock | No virus mock | | | | x |

TABLE 3

| 05Abic | | D4-fl | Myog | MyoD | MyHC | FRG1 | Utr | 18S |
|---|---|---|---|---|---|---|---|---|
| ASH1L | PJ1 | 0.339864916 | 1.795183167 | 0.723770281 | 1.065673257 | 1.051082754 | 0.699398352 | 1.372396234 |
| | PJ2 | 0.137087067 | 0.884454216 | 0.850293889 | 0.722058184 | 1.172117454 | 0.814964952 | 1.310589724 |
| | PJ3 | 0.243399646 | 0.721807474 | 0.989491359 | 1.341208221 | 1.140980999 | 1.128078955 | 1.18473858 |

TABLE 3-continued

| 05Abic | | D4-fl | Myog | MyoD | MyHC | FRG1 | Utr | 18S |
|---|---|---|---|---|---|---|---|---|
| BRD2 | PJ11 | 0.124003902 | 1.026423141 | 0.927702908 | 0.734217035 | 1.249955089 | 0.606707767 | 1.111712256 |
| | PJ12 | 0.11270391 | 1.087513313 | 0.903981253 | 0.792653631 | 1.177865629 | 0.675476924 | 1.099042238 |
| | PJ14 | 1.569559486 | 0.291130929 | 0.950277519 | 1.097925476 | 0.91354105 | 0.82051485 | 0.832829365 |
| BRD3 | PJ16 | 0.073308504 | 0.588032277 | 0.659660138 | 0.400760054 | 1.064750605 | 0.61837148 | 0.779623083 |
| | PJ17 | 0.139921704 | 1.20855815 | 0.865477595 | 0.633576884 | 1.202664941 | 0.697405138 | 0.922625539 |
| | PJ18 | 0.199308304 | 0.256805957 | 1.020418879 | 1.321564191 | 1.042463976 | 0.86120469 | 0.704754346 |
| BRD4 | PJ21 | 0.586975241 | 1.797809057 | 0.849640707 | 0.853974583 | 1.244427436 | 0.706568049 | 0.998072459 |
| | PJ22 | 0.392497933 | 2.123199302 | 0.939840515 | 0.74989233 | 1.233460535 | 0.630999335 | 0.858984128 |
| BRDT | PJ26 | 0.182233541 | 1.647598037 | 0.869932672 | 0.675990268 | 0.991533271 | 0.716637895 | 1.183553643 |
| | PJ27 | 0.39409226 | 1.184659362 | 0.75864719 | 0.3912232 | 1.141864481 | 0.673184416 | 1.083000707 |
| CARM1 | PJ45 | 0.108241628 | 0.345409202 | 0.884104443 | 0.34384743 | 1.100175048 | 0.682696489 | 0.954703793 |
| | PJ46 | 0.150324814 | 0.985263418 | 0.974628758 | 0.517851974 | 0.936585175 | 0.686617911 | 1.085577325 |
| | PJ47 | 0.468247646 | 1.661923124 | 0.978851217 | 1.130851995 | 1.193312199 | 1.355174788 | 1.494285831 |
| KDM4A | PJ62 | 0.426541187 | 0.676601566 | 0.962821736 | 0.552724982 | 1.013914728 | 0.711841551 | 0.790506216 |
| | PJ63 | 0.08675943 | 1.020997568 | 0.806759564 | 0.755325783 | 1.099330519 | 0.803152975 | 0.888975846 |
| KDM4B | PJ67 | 0.286994951 | 1.431846337 | 0.959265959 | 0.546698746 | 1.014645521 | 0.843096956 | 0.852762632 |
| | PJ69 | 0.582612869 | 1.103597624 | 0.81591101 | 0.51460761 | 1.058393612 | 0.666273446 | 0.793717254 |
| KDM4C | PJ73 | 0.110105085 | 1.337908478 | 0.904501387 | 0.796780248 | 1.043171089 | 0.639320374 | 1.253018728 |
| | PJ74 | 0.088012999 | 1.810313807 | 0.762119329 | 0.764225297 | 1.210660137 | 0.712059103 | 1.12920813 |
| | PJ75 | 0.181231368 | 1.318365665 | 1.048477015 | 0.982589446 | 0.776565473 | 1.017900514 | 0.978062388 |
| KDM4D | PJ78 | 0.144577649 | 0.958008541 | 0.893532182 | 0.420034943 | 0.946288614 | 0.584311635 | 0.943638793 |
| | PJ79 | 0.087273652 | 0.330498385 | 0.712642262 | 0.272765272 | 1.10889068 | 0.632335355 | 1.185206261 |
| KMT2A | PJ83 | 0.297635255 | 0.848764546 | 0.888701658 | 0.444414898 | 0.940745416 | 0.507323792 | 1.086741033 |
| | PJ84 | 0.214732055 | 0.41663781 | 0.750070477 | 0.321423293 | 1.032027996 | 0.535478448 | 1.075179933 |
| BAZ1B | PJ142 | 0.320102383 | 0.892311433 | 0.806914582 | 0.487302003 | 1.037467533 | 0.600594634 | 0.989367297 |
| | PJ143 | 0.175941092 | 0.744950932 | 0.765959818 | 0.408717935 | 0.917156321 | 0.635906852 | 0.793088613 |
| BAZ1A | PJ152 | 0.18918597 | 1.317628835 | 0.991031696 | 0.850315179 | 0.904681646 | 0.954007328 | 1.312164074 |
| | PJ153 | 0.266404431 | 1.583787478 | 0.959111923 | 1.368107943 | 1.215016404 | 0.935474645 | 1.424058282 |
| | PJ154 | 0.628471886 | 0.503660235 | 0.840463254 | 1.57238077 | 1.231852169 | 1.25972346 | 1.097606432 |
| BAZ2A | PJ157 | 0.450227643 | 0.75628977 | 1.079852527 | 0.731142973 | 1.074586647 | 0.876043058 | 1.130700205 |
| | PJ158 | 0.102728776 | 0.841755833 | 0.878376729 | 0.749914044 | 1.022222937 | 0.833687955 | 1.094352491 |
| SMARCB1 | PJ187 | 0.149552771 | 1.016336933 | 0.939840515 | 0.655898598 | 1.025120796 | 0.666070461 | 1.038033989 |
| | PJ188 | 1.1293311 | 3.56373827 | 1.212760975 | 1.144165153 | 0.904361535 | 1.098546976 | 0.793253449 |
| | PJ190 | 1.087974504 | 1.158982971 | 0.9200568 | 0.76057949 | 0.844097822 | 1.00700364 | 1.068475609 |
| SMARCA5 | PJ195 | 0.168001339 | 0.800281293 | 0.898085556 | 0.780342703 | 0.98647348 | 1.023684011 | 0.990512326 |
| | PJ196 | 0.108533259 | 0.924670334 | 0.721965982 | 0.469023371 | 0.897351593 | 0.826143034 | 0.98074374 |
| | PJ196(repeat) | 0.196691569 | 0.929251089 | 0.910255442 | 0.592649529 | 0.920929641 | 1.231136865 | 1.047732055 |
| | PJ197 | 0.759851475 | 3.20850592 | 1.290950658 | 0.600207491 | 1.20282491 | 1.086519425 | 1.060370731 |
| BAP1 | PJ200 | 0.212467816 | 1.759563167 | 0.941014407 | 1.711392816 | 0.984321925 | 0.534605168 | 0.845146883 |
| | PJ201 | 0.148130686 | 0.610314851 | 1.11293147 | 0.922039855 | 0.930531976 | 1.09067825 | 1.042772209 |
| | PJ202 | 0.510554576 | 0.537384483 | 0.999101867 | 1.014196772 | 1.060064726 | 0.800039661 | 1.422790092 |
| BPTF | PJ6 | 0.228481901 | 0.619358718 | 1.209276723 | 0.994229145 | 1.132881945 | 1.036153723 | 1.105612584 |
| | PJ7 | 8.84566039 | 0.710024754 | 1.091582222 | 1.602193581 | 1.006635556 | 0.985193449 | 0.955521898 |
| BRPF1 | PJ31 | 0.16564683 | 0.550832652 | 1.053943685 | 0.64261253 | 1.149110327 | 1.113301155 | 0.871727828 |
| | PJ32 | 1.199737759 | 0.654927934 | 1.090011508 | 1.01068546 | 1.088378081 | 1.147487899 | 1.038249306 |
| BRPF3 | PJ40 | 0.434389237 | 0.98976198 | 1.141214284 | 0.820548576 | 1.06855752 | 0.81469057 | 1.032118072 |
| | PJ41 | 0.256716096 | 1.011753695 | 1.210059043 | 1.053079053 | 1.162242786 | 1.145393054 | 1.401916912 |
| KDM6A | PJ55 | 0.226084689 | 1.309479185 | 1.337150168 | 1.404742944 | 0.972653282 | 1.248450517 | 1.339243894 |
| | PJ56 | 0.287660242 | 0.985635843 | 0.926583425 | 0.930421992 | 0.958453588 | 1.12238212 | 1.117295273 |
| KDM6B | PJ60 | 0.679110105 | 0.607373393 | 0.999035001 | 1.227193435 | 0.976997415 | 0.960958518 | 0.983234894 |
| | PJ61 | 0.212640692 | 1.242673545 | 1.100282377 | 1.198420473 | 1.046064301 | 1.18681485 | 1.207438468 |
| KMT2C | PJ89 | 0.157680244 | 2.463045313 | 1.29662295 | 1.050299486 | 0.939764596 | 0.962212923 | 1.172252104 |
| | PJ90 | 0.341522916 | 0.350124817 | 1.099702159 | 1.090341551 | 1.129267588 | 0.989264411 | 1.051504267 |
| KMT2E | PJ94 | 0.291530232 | 1.177674813 | 1.063138748 | 1.2259326 | 1.037253338 | 1.298194358 | 1.086507919 |
| | PJ95 | 0.54276446 | 0.642339495 | 0.967114224 | 1.142362888 | 1.08300571 | 0.989549583 | 1.065809554 |
| NEK6 | PJ99 | 0.192094471 | 0.789435776 | 0.942129271 | 1.250790527 | 0.818057845 | 1.024273754 | 0.917126328 |
| | PJ100 | 0.237130444 | 0.654268485 | 0.850154988 | 1.461879519 | 0.933031394 | 0.916750689 | 0.689753562 |
| PHF2 | PJ104 | 0.151333308 | 0.560545139 | 0.834101718 | 1.063690799 | 0.861653342 | 0.913827211 | 0.924436924 |
| | PJ105 | 0.171838437 | 0.759976425 | 1.081702597 | 1.20853231 | 1.129104856 | 1.328039558 | 1.010877389 |
| PRMT1 | PJ109 | 0.295747472 | 0.640034943 | 1.094725915 | 0.988176188 | 1.227450266 | 1.105611022 | 1.101251698 |
| | PJ110 | 0.183760248 | 0.560388696 | 0.995512843 | 1.383420734 | 1.275295342 | 1.174906589 | 1.137296184 |
| SETD1A | PJ114 | 0.143188509 | 1.486481641 | 1.244942519 | 0.913727589 | 1.120507539 | 1.042108905 | 1.390811066 |
| | PJ115 | 0.172598238 | 0.544693539 | 1.027787877 | 0.828241032 | 1.129755831 | 1.198104075 | 1.126120475 |
| SETD1B | PJ119 | 0.213909702 | 0.588365643 | 1.070533463 | 0.949087984 | 0.992253381 | 0.936659482 | 1.034675878 |
| | PJ120 | 0.188838685 | 0.542621182 | 0.951512975 | 0.941922794 | 1.169091123 | 1.021005865 | 0.992527445 |
| SMYD3 | PJ121 | 0.918747691 | 0.707428191 | 0.999101867 | 0.736027478 | 1.079304166 | 1.647567517 | 1.093749887 |
| | PJ122 | 0.717941338 | 0.752490768 | 1.324312717 | 0.82739557 | 1.133099667 | 1.172947662 | 1.148706718 |
| SF3B1 | PJ162 | 0.270115821 | 1.90743841 | 1.130076786 | 0.644089947 | 1.181217607 | 1.278632217 | 1.296056991 |
| | PJ163 | 0.493760658 | 0.623550066 | 0.999035001 | 1.005539781 | 1.288475022 | 1.245360936 | 1.270320361 |
| UFL1 | PJ182 | 0.270757616 | 1.567331031 | 1.21380994 | 0.845469383 | 1.283018046 | 1.234449695 | 1.227814695 |
| | PJ183 | 0.200269298 | 1.209332663 | 0.968197459 | 0.845712955 | 1.12265253 | 1.338240664 | 0.990406606 |
| USP3 | PJ209 | 0.233387444 | 1.195860264 | 1.100709575 | 1.063485913 | 1.156769563 | 1.179748175 | 1.020798907 |
| USP7 | PJ211 | 0.415591698 | 1.259502206 | 1.389686068 | 0.736378535 | 1.189433625 | 1.208407515 | 1.14707669 |
| USP16 | TS30 | 0.413693083 | 1.792221738 | 1.364813371 | 1.225638253 | 1.22554702 | 1.202891394 | 1.060829187 |
| | TS31 | 0.279686747 | 1.396516052 | 0.989823935 | 1.003899904 | 0.989075362 | 0.958843611 | 0.936981743 |
| MYSM1 | TS190 | 0.172394942 | 0.343070554 | 0.96192541 | 1.362229766 | 1.062094011 | 0.928224743 | 0.980744789 |
| | TS191 | 0.185232585 | 0.604956142 | 1.026998347 | 1.089313656 | 1.058616325 | 0.905360288 | 0.942276403 |

TABLE 3-continued

| 05Abic | | D4-fl | Myog | MyoD | MyHC | FRG1 | Utr | 18S |
|---|---|---|---|---|---|---|---|---|
| CTL | TRN/TRCNS Mock | 0.963383755 1 | 0.322830129 1 | 0.981712992 1 | 0.869489182 1 | 1.149662323 1 | 0.969458381 1 | 0.966238572 1 |

Figure 1:
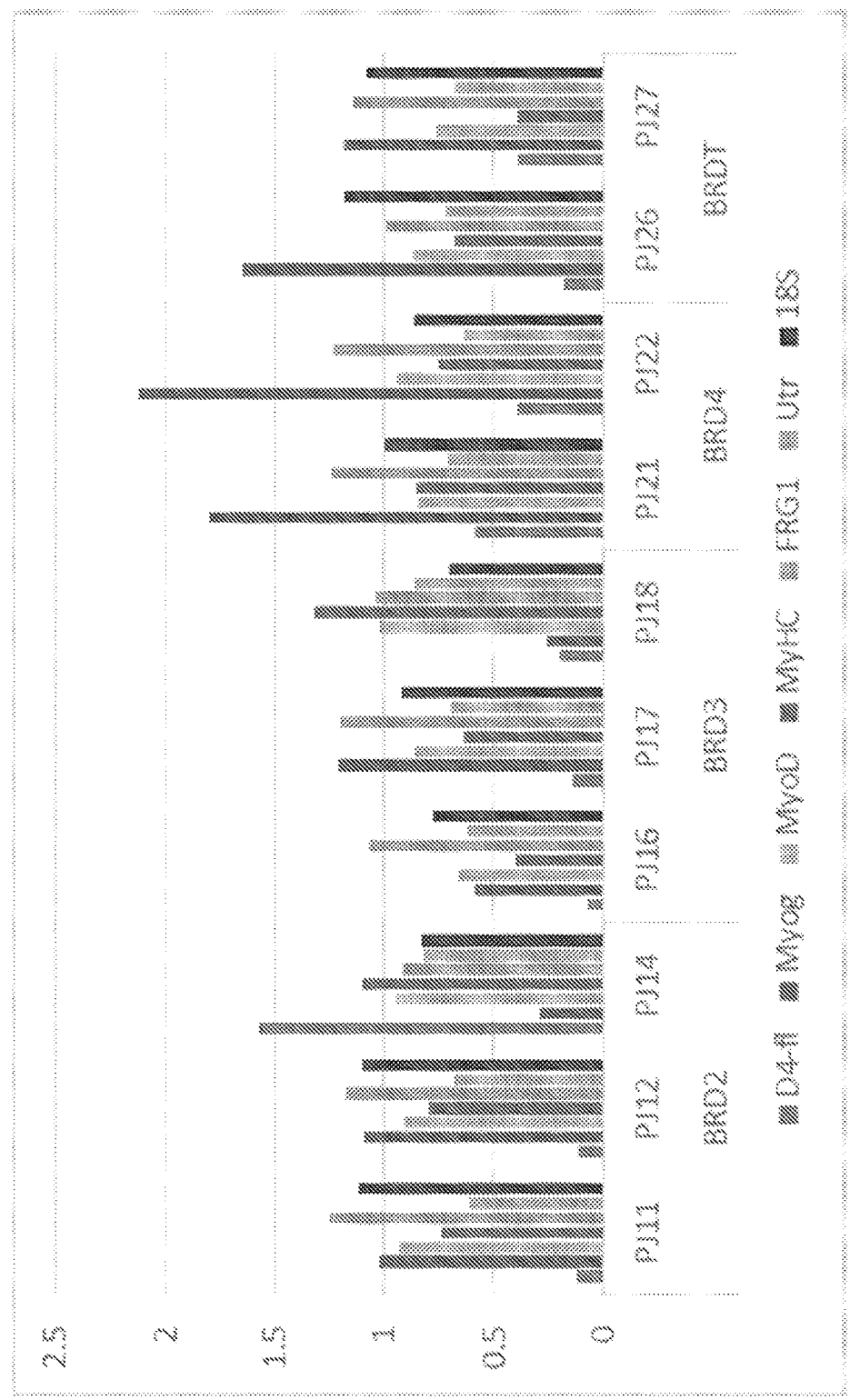
FIG. 1 shows effects of shRNA knockdown of Bromodomain-containing protein (BRD) family members BRD2, BRD3, BRD4, and BRDT, on expression of Dux4 (DUX4-fl), other myogenic factors (Myogenin, MyoD, MyHC), FSHD Region Gene 1 (FRG1), Utrophin (UTRN), and 18S. Each BRD gene was knocked down with two different lentivirally-expressed shRNAs.

FIG. 1 shows effects of shRNA knockdown of BRD2, BRD3, BRD4, and BRDT, on expression of Dux4 (DUX4-fl), other myogenic factors (Myogenin, MyoD, MyHC), FRG1, UTRN, and 18S. Data indicate that knockdown of BRD2 with two different shRNAs reduces DUX4-fl expression. However, knockdown of BRD4 has little effect on DUX4 expression.

Figure 2:
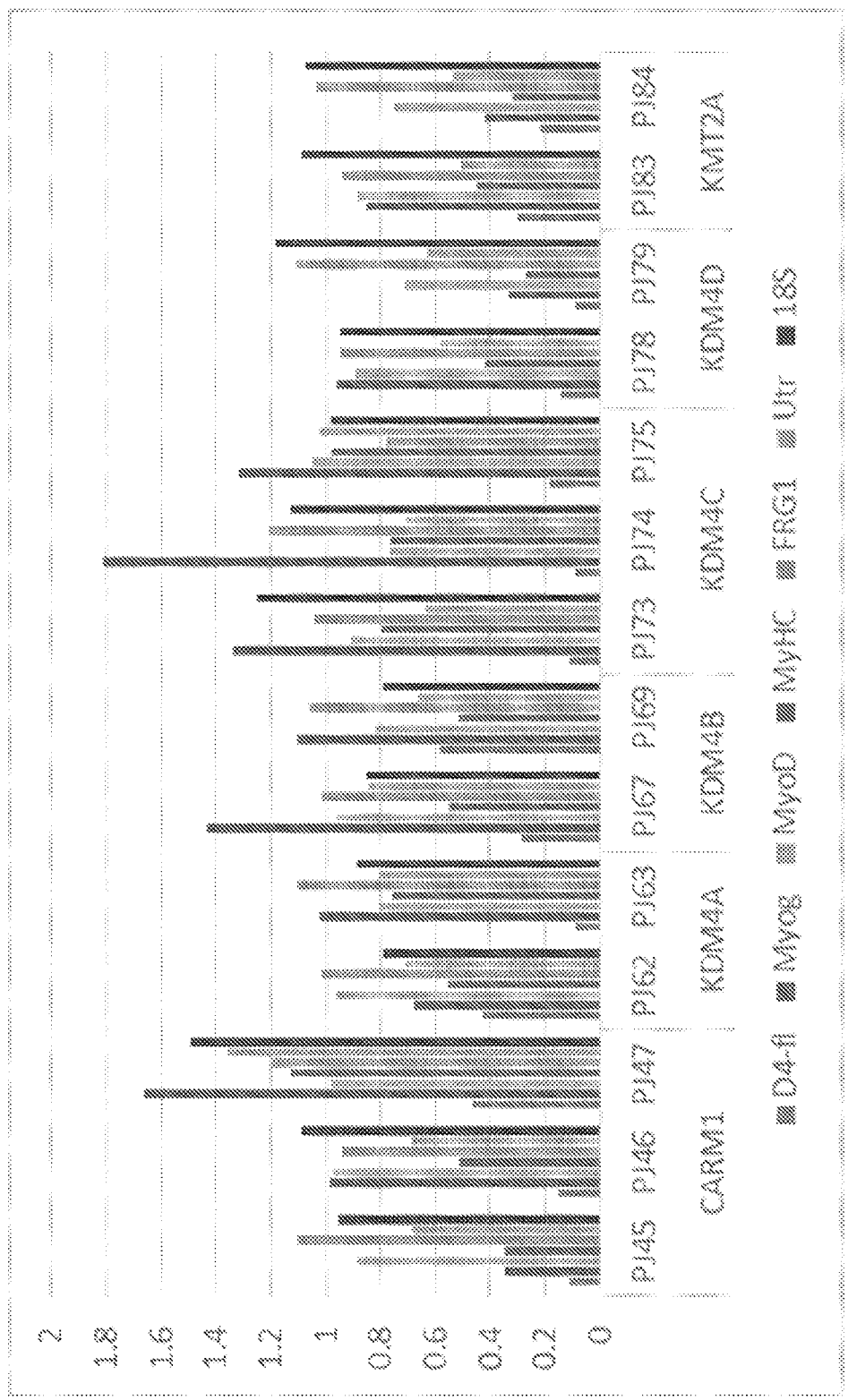
FIG. 2 shows effects of shRNA knockdown of methylase family members Coactivator Associated Arginine Methyltransferase 1 (CARM1) and Lysine Methyltransferase 2A (KMT2A), and Lysine demethylase 4A (KDM4A), Lysine demethylase 4B (KDM4B), Lysine demethylase 4C (KDM4C), and Lysine demethylase 4D (KDM4D), on expression of Dux4 (DUX4-fl), other myogenic factors (Myogenin, MyoD, MyHC), FSHD Region Gene 1 (FRG1), Utrophin (UTRN), and 18S. Each gene was knocked down with two different lentivirally-expressed shRNAs.

FIG. 2 shows effects of shRNA knockdown of CARM1, KMT2A, and KDM4A-4D, on expression of Dux4 (DUX4-fl) and a panel of additional genes of interest (Myogenin, MyoD, MyHC, FRG1, UTRN, and 18S). Data indicate that knockdown of CARM1 with two different shRNAs each results in reduction of DUX4-fl expression. A third shRNA targeting CARM1 did not result in reduction of DUX4-fl expression. Knockdown of KDM4C using three different shRNAs resulted in reduction of DUX4-fl expression.

Figure 3:
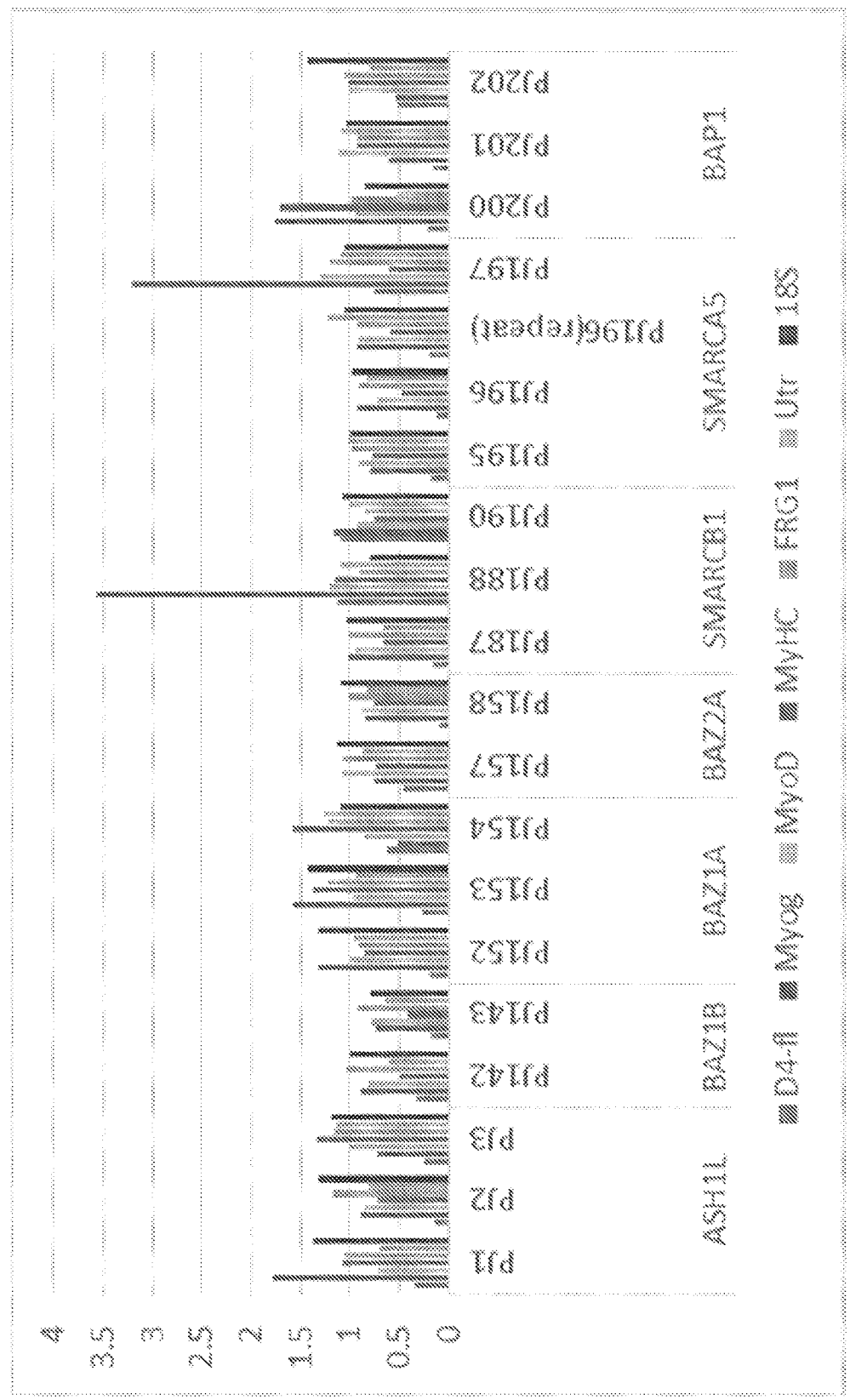
FIG. 3 shows effects of shRNA knockdown of Bromodomain Adjacent To Zinc Finger Domain 1B (BAZ1B), Bromodomain Adjacent To Zinc Finger Domain 1A (BAZ1A), Bromodomain Adjacent To Zinc Finger Domain 2A (BAZ2A), SWI/SNF-related matrix-associated actin-dependent regulator of chromatin subfamily B member 1 (SMARCB1), SWI/SNF-related matrix-associated actin-dependent regulator of chromatin subfamily A member 5 (SMARCA5), BRCA1 Associated Protein 1 (BAP1), and ASH1-like protein (ASH1L), on expression of Dux4 (DUX4-fl), other myogenic factors (Myogenin, MyoD, MyHC), FSHD Region Gene 1 (FRG1), Utrophin (UTRN), and 18S. Each gene was knocked down with two different lentivirally-expressed shRNAs.
Figure 4A:
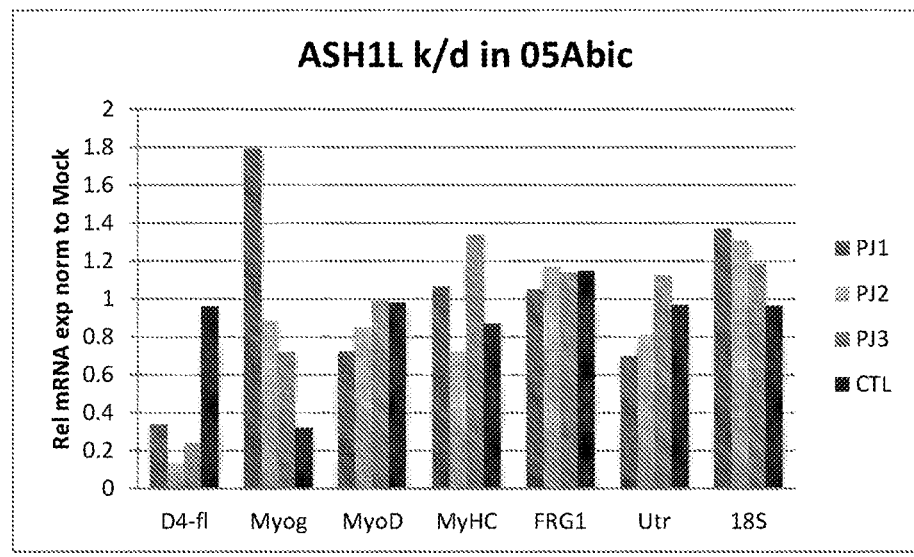
FIGS. 4A-4E show shRNA knockdown of candidate target genes.
Figure 4B:
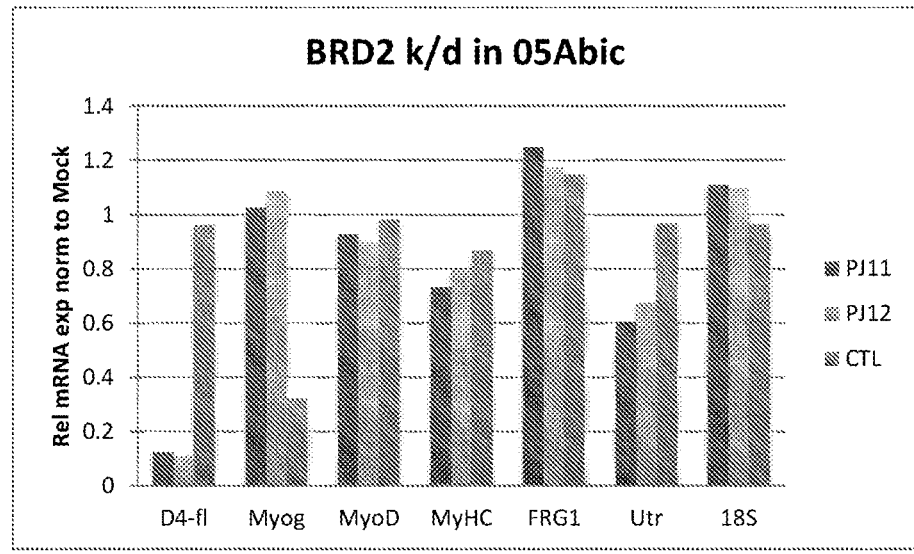
Figure 4C:
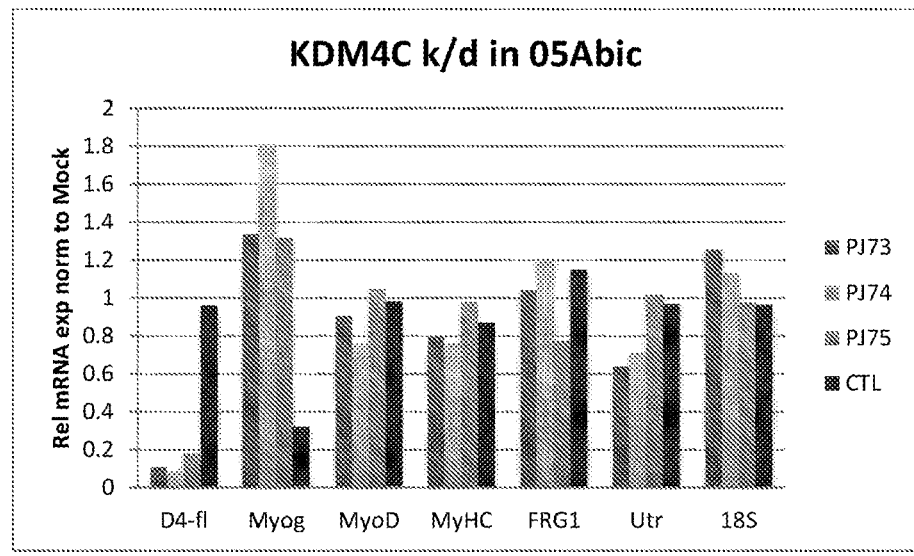
Figure 4D:
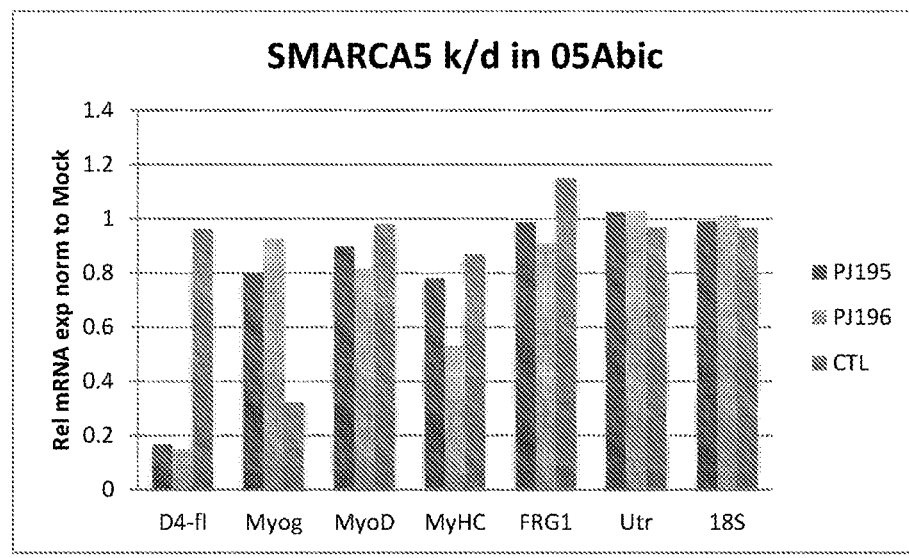
Figure 4E:
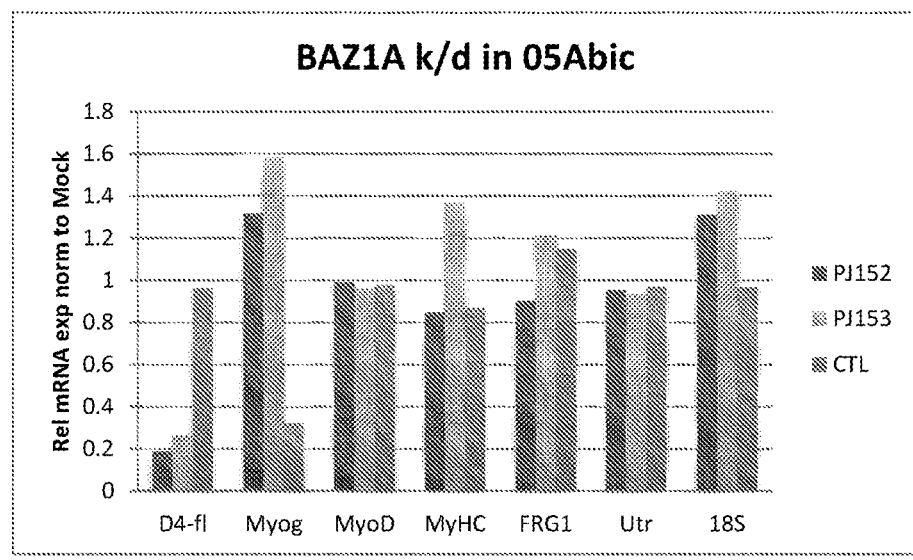

FIG. 3 shows effects of shRNA knockdown of Bromodomain Adjacent To Zinc Finger Domain 1B (BAZ1B), Bromodomain Adjacent To Zinc Finger Domain 1A (BAZ1A), Bromodomain Adjacent To Zinc Finger Domain 2A (BAZ2A), SWI/SNF-related matrix-associated actin-dependent regulator of chromatin subfamily B member 1 (SMARCB1), SWI/SNF-related matrix-associated actin-dependent regulator of chromatin subfamily A member 5 (SMARCA5), BRCA1 Associated Protein 1 (BAP1), and ASH1-like protein (ASH1L), on expression of Dux4 (DUX4-fl), other myogenic factors (Myogenin, MyoD, MyHC), FSHD Region Gene 1 (FRG1), Utrophin (UTRN), and 18S. Each gene was knocked down with two different lentivirally-expressed shRNAs.

FIG. 4 shows from the screen described above, 5 candidate genes (SMARCA5, BRD2, KDM4C, ASH1L, and BAZ1A) that fit the following criteria were identified: 1) candidate genes function in separate pathways, and knocking down each gene individually decreases DUX4 expression; 2) multiple shRNAs targeting each of these candidate genes yield a similar knockdown of DUX4 expression (e.g., to minimize possible off-target effect); 3) targeting these candidate genes did not adversely affect cell morphology or the expression of muscle-specific genes; and, 4) the proteins encoded by the candidate genes contain small molecule druggable domains.

Thus, in some embodiments, the inhibition or knockdown of any one or combination of these candidate genes (or another candidate gene identified by the screening method described above) using small molecules can inhibit or decrease transcription of DUX4 and/or induce a repressive chromatin environment at D4Z4 repeat arrays.

To the best of the inventors' knowledge, the genes identified in this screen are previously unrecognized regulators of DUX4 expression and therapeutic targets for FSHD. In addition, the screen described in this example incorporates several important experimental aspects that are likely absent from other screens: 1) the use of primary muscle cells from an FSHD patient; 2) performing the screen on terminally differentiated muscle cells (as in a patient's muscles); 3) directly assaying levels of the pathogenic mRNA isoform of DUX4 (DUX4-fl) rather than a reporter or a downstream target; 4) screening out candidates that affect myogenic genes; and, 5) reverting the D4Z4 repeat array chromatin back to a nonpathogenic state, which in some embodiments renders a therapy targeting the identified candidate gene more stable and long-term.

Example 2

Figure 5:
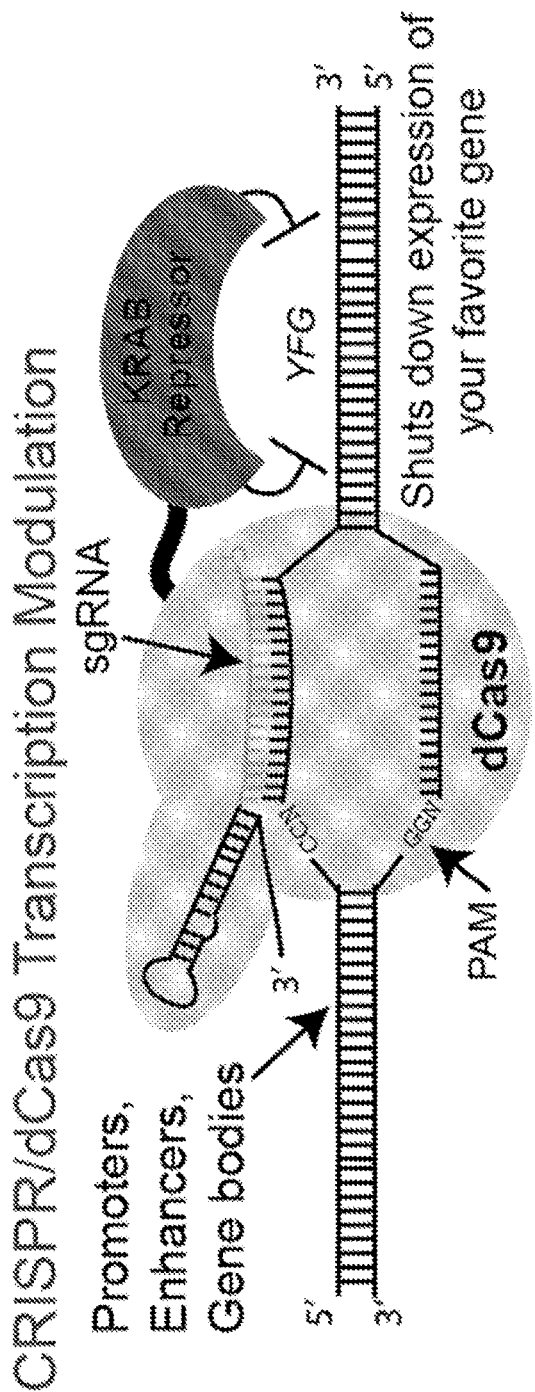
FIG. 5 shows a graphic depiction of CRISPR/dCas9/KRAB transcription modulation.

This example describes modulation of DUX4 expression by inhibition of DUX4 chromatin modifiers using a gene editing complex. Briefly, single guide RNAs (sgRNAs) targeting chromatin modifiers of DUX4 expression (e.g., KDM4C, ASH1L, SMARCA5, BAZ1A, BRD2) were used to direct transcriptional modulation of DUX4 using a gene editing molecule comprising dCas9 fused to a KRAB repressor. FIG. 5 provides a graphic depiction of the CRISPR/dCas9/KRAB transcription modulation system described in this example.

Knockdowns were performed in 17ABic cells, which are myogenic cells derived from a FSHD patient. Between six and eight sgRNAs were tested for each candidate gene. Table 4 describes examples of guide RNAs targeting chromatin modifiers of DUX4.

TABLE 4

Guide RNAs (qRNAs)

| Gene | GENE ID NO: | SEQ ID NO: | sgRNA sequences + Sa/Sp PAM (NNGRRT/ NGG) | On-target score | Off-target score | Specificity |
|---|---|---|---|---|---|---|
| KDM4C | NC_000009.12 | 12 | CGTTACCGGGGTGGAGCCTCGGAAT | 0.08 | 76 | High |
| | | 13 | CTTGCCCGGAAGCGCTGGCTGGGGT | 0.06 | 81 | High |
| SMARCA5 | NC_000004.12 | 14 | AAAACCGTGAGACTTCACTTGGGGT | 0.13 | 78 | High |
| | | 15 | TGTGTCTTCTGTGCCTGACAGGGGT | 0.01 | 59 | High |
| BAZ1A | NC_000014.9 | 16 | ATACAAGTTAAATCGTAATTGGAAT | 0.09 | 70 | High |
| | | 17 | TTGACTACACGATGGGAAAAGGGAT | 0.05 | 77 | High |
| BRD2 | NC_000006.12 | 18 | GCCAAAGCAGGGAAACGGGAGGGGT | 0.36 | 64 | High |
| ASH1L | NC_000001.11 | 19 | GCCCTCACGCGTACCTTCAACGG | | | High |

*sgRNAs target the promoter or exon 1 of each gene
** sgRNAs target sequences flanking dual PAMs recognizable by both SaCas9 and SpCas9
***scores and specificity are sgRNA Designer scores (CRISPR Design Tool; http://crispr.mit.edu)

Relative expression levels for each candidate gene, DUX4-fl (D4-fl), FRG1, MyoG, MyHC, 18S and MyoD were quantified. Generally, levels of gene-specific knockdown were consistent with CRISPR/Cas9-mediated knockdown reported in the field (e.g., as described by Radzisheuskaya et al. (2016) Nucleic Acids Research 1; doi: 10.1093/nar/gkw583).

Figure 6:
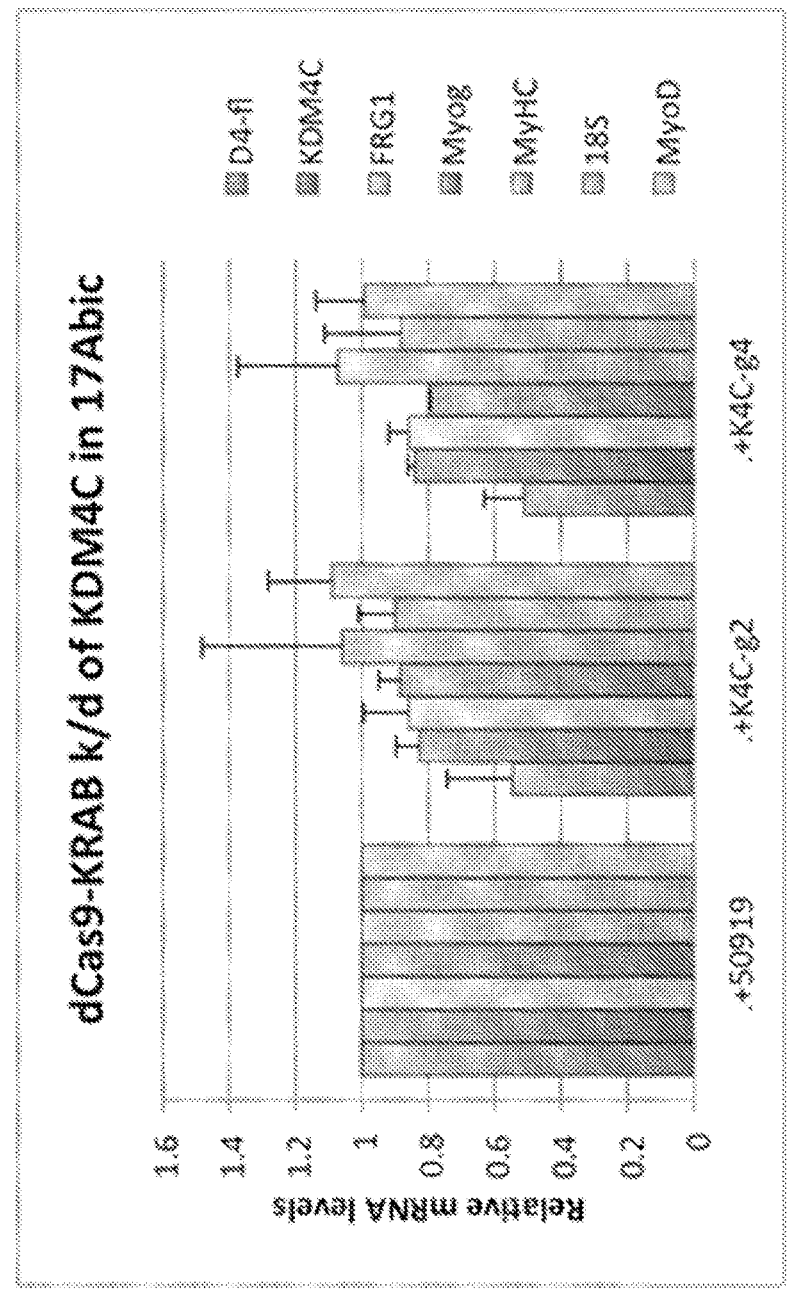
FIG. 6 shows representative data for lentiviral-based dCas9-KRAB knockdown of KDM4C in 17ABic cells. Relative gene expression of KDM4C, DUX4-fl (D4-fl), FRG1, MyoG, MyHC, 18S and MyoD are shown. Data from experiments using two different guide RNAs (gRNAs) are shown.

FIG. 6 shows representative data for lentiviral-based dCas9-KRAB knockdown of KDM4C in 17ABic cells. Data from experiments using two different guide RNAs (gRNAs) are shown. Each guide strand mediated a decrease in DUX4-fl (D4-fl). Expression levels of KDM4C were approximately 80% after knockdown, indicating that DUX4 expression is very sensitive to changes in KDM4C expression level.

Figure 7:
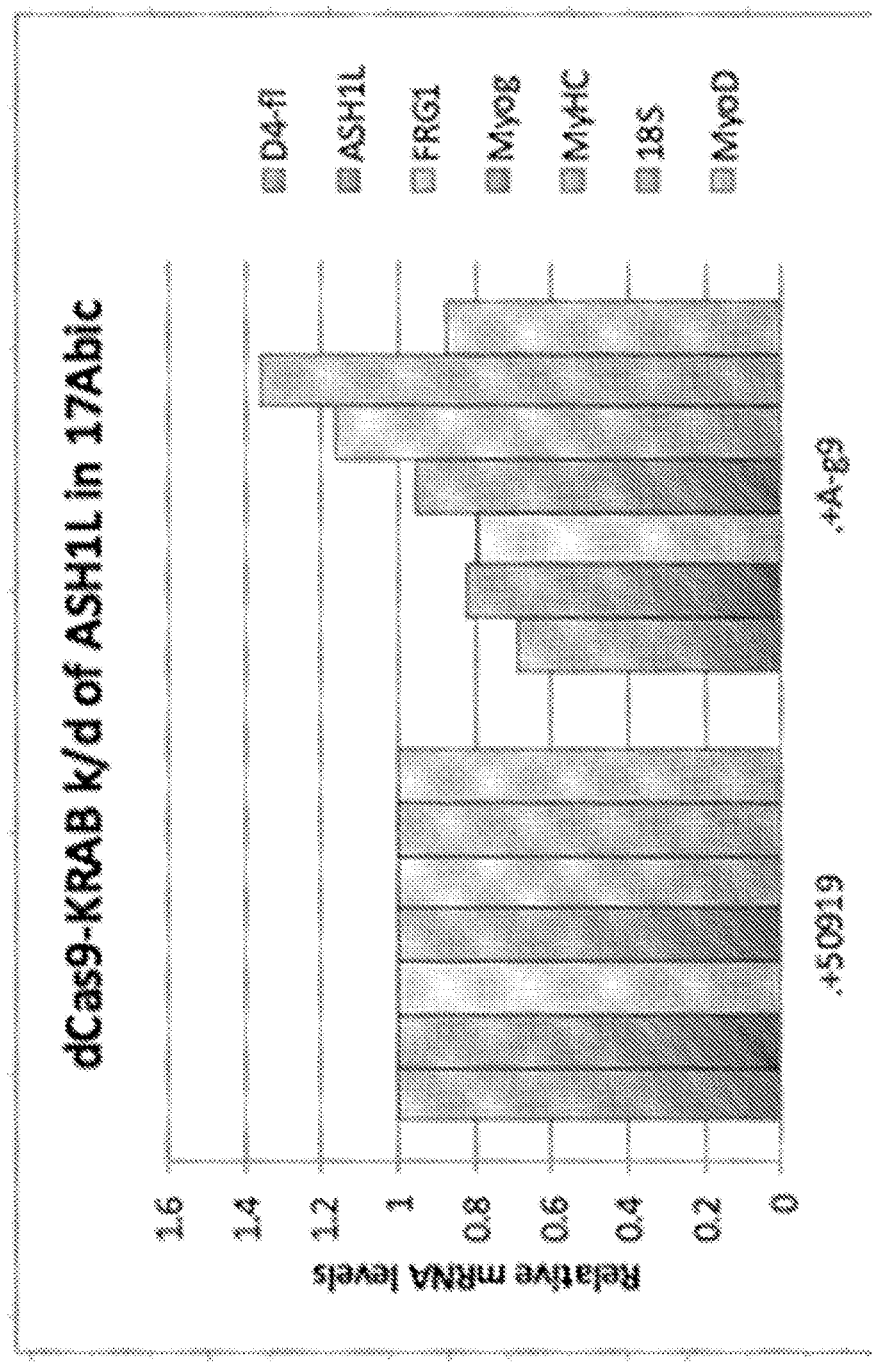
FIG. 7 shows representative data for lentiviral-based dCas9-KRAB knockdown of ASH1L in 17ABic cells. Relative gene expression of ASH1L, DUX4-fl (D4-fl), FRG1, MyoG, MyHC, 18S and MyoD are shown. Data from experiments using a single guide RNA (gRNA) are shown.

FIG. 7 shows representative data for lentiviral-based dCas9-KRAB knockdown of ASH1L in 17ABic cells. Data from experiments using a single guide RNA (gRNA) are shown. Knockdown of ASH1L (approximately 20%) resulted in a decrease of DUX4-fl expression. Expression levels of MyoG and MyoD were not significantly changed.

Figure 8:
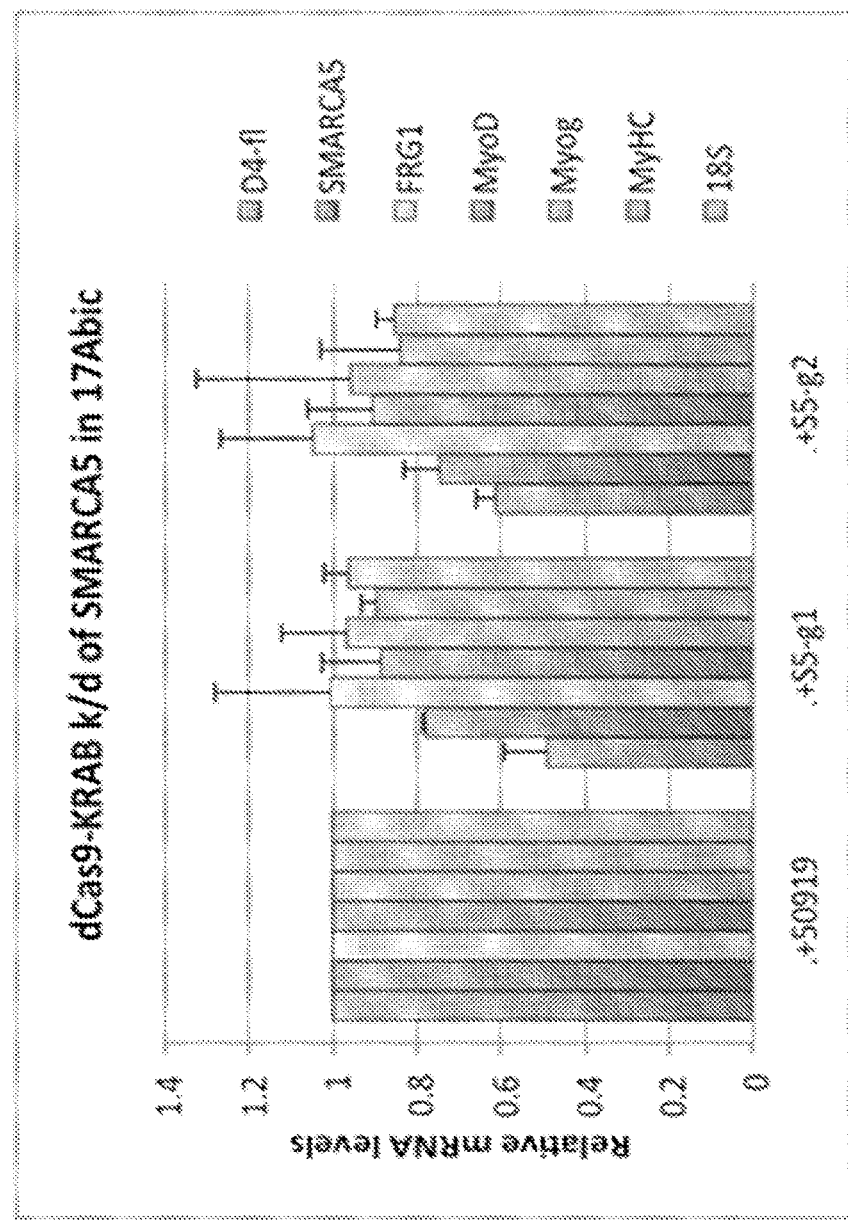
FIG. 8 shows representative data for lentiviral-based dCas9-KRAB knockdown of SMARCA5 in 17ABic cells. Relative gene expression of SMARCA5, DUX4-fl (D4-fl), FRG1, MyoG, MyHC, 18S and MyoD are shown. Data from experiments using two different guide RNAs (gRNAs) are shown.

FIG. 8 shows representative data for lentiviral-based dCas9-KRAB knockdown of SMARCA5 in 17ABic cells. Data from experiments using two different guide RNAs (gRNAs) are shown. Each guide strand mediated a decrease in DUX4-fl (D4-fl). Expression levels of SMARCA5 were approximately 75% after knockdown, indicating that DUX4 expression is very sensitive to changes in SMARCA5 expression level. Expression levels of MyoG and MyoD were not significantly changed.

Figure 9:
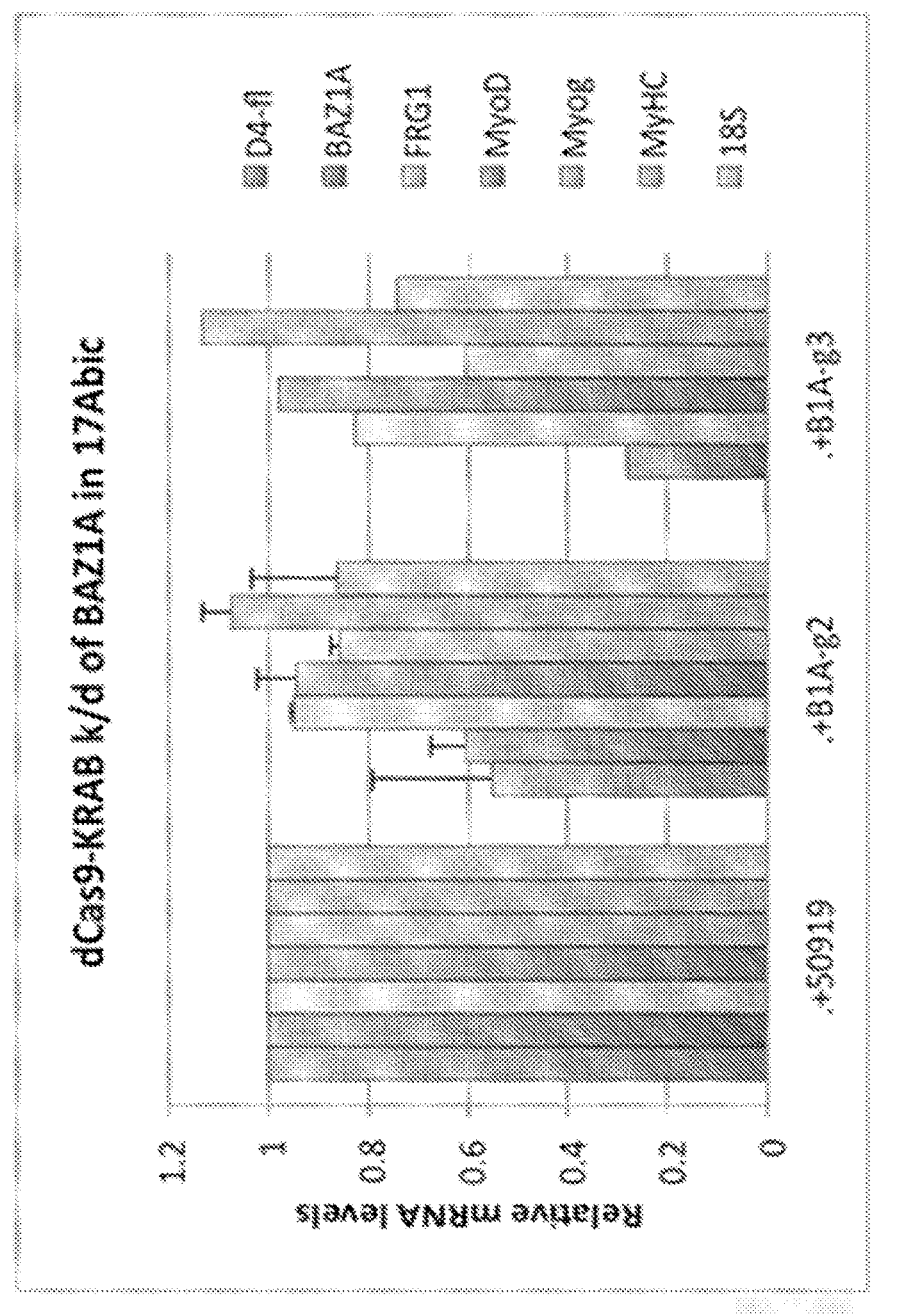
FIG. 9 shows representative data for lentiviral-based dCas9-KRAB knockdown of BAZ1A in 17ABic cells. Relative gene expression of BAZ1A, DUX4-fl (D4-fl), FRG1, MyoG, MyHC, 18S and MyoD are shown. Data from experiments using two different guide RNAs (gRNAs) are shown.

FIG. 9 shows representative data for lentiviral-based dCas9-KRAB knockdown of BAZ1A in 17ABic cells. Data from experiments using two different guide RNAs (gRNAs) are shown. Each guide strand mediated a decrease in DUX4-fl (D4-fl), which correlates with reduction of BAZ1A expression level. Knockdown of BAZ1A resulted in the largest decrease in DUX4 expression level of any gene tested.

Figure 10:
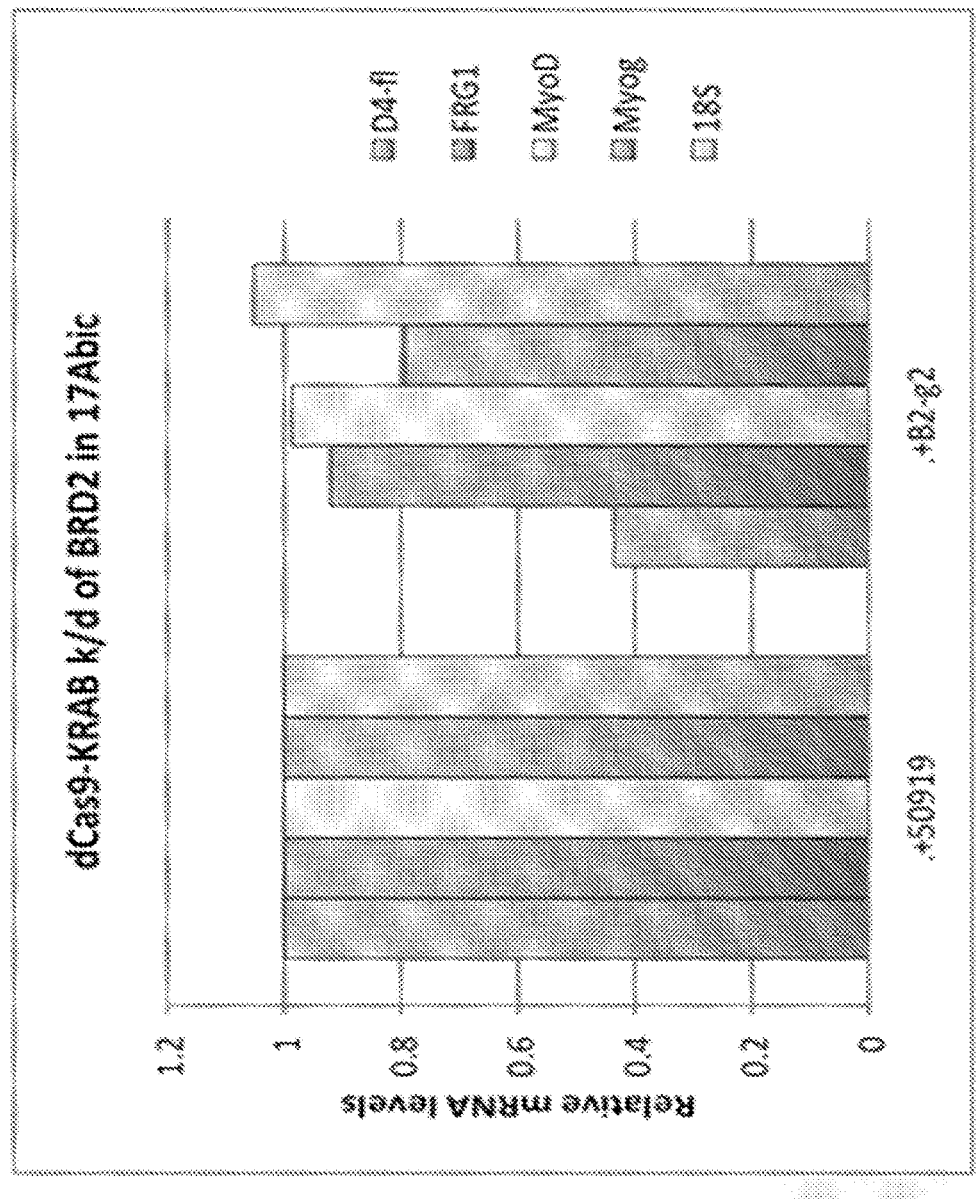
FIG. 10 shows representative data for lentiviral-based dCas9-KRAB knockdown of BRD2 in 17ABic cells. Relative gene expression of BRD2, DUX4-fl (D4-fl), FRG1, MyoG, MyHC, 18S and MyoD are shown. Data from experiments using a single guide RNA (gRNA) are shown.

FIG. 10 shows representative data for lentiviral-based dCas9-KRAB knockdown of BRD2 in 17ABic cells. Data from experiments using a single guide RNA (gRNA) are shown. A decrease in DUX4 expression level was observed.

In summary, knockdown of KDM4C, ASH1L, SMARCA5, BAZ1A, BRD2 using a gene editing complex confirms the RNAi results described Example 1 in the context of reducing DUX4 expression level by inhibiting a chromatin modifier of DUX4.

Example 3

Plasmids and Antibodies.

The pHAGE EF1-dCas9-KRAB (Addgene plasmid #50919) and pLKO.1-puro U6 sgRNA BfuAI stuffer lentiviral plasmids were obtained. The ChIP-grade antibodies used in this example, α-H3K9me3 (ab8898) and α-histone H3 (ab1791), were purchased from a commercial source.

sgRNA Design and Plasmid Construction.

A publically available sgRNA design tool was used to identify candidate single-stranded guide RNAs (sgRNAs) targeting the promoter/exon 1 regions of human BAZ1A, BRD2, KDM4C, and SMARCA5 (Table 4). To build in flexibility for experiments beyond the scope of this study, sgRNAs that target sequences flanking dual protospacer adjacent motifs (PAMs) recognizable by both SaCas9 and SpCas9 were prioritized. Predicted off-target matches were determined using the CRISPR Design Tool (http://crispr.mit.edu). Six to eight sgRNAs for each target gene were cloned individually into BfuAI sites in the pLKO.1-puro U6 sgRNA BfuAI stuffer plasmid and sequence-verified.

Cell Culture, Transient Transfections, and Lentiviral Infections.

Myogenic cultures derived from biceps muscles of unrelated FSHD1 patients (05Abic, 17Abic, and 18Abic) were grown in Ham's F-10 medium supplemented with 20% FBS (Hyclone), 0.5% chick embryo extract, 1% antibiotics & antimycotics, and 1.2 mM $CaCl_2$. 293T packaging cells were grown in DMEM+10% FBS+0.1% penicillin-streptavidin. For shRNA knockdown experiments, 293T cells were transfected with lentiviral packaging plasmid (pCMV-dR8.91), envelope plasmid (VSV-G), and SIGMA MISSION shRNA expression plasmids. Lentiviral supernatants were harvested, aliquoted, and frozen at −80° C. FSHD1 skeletal myoblasts were seeded in collagen-coated 6-well plates (for gene expression analysis) or 10-cm plates (for ChIP) and grown to confluence, then allowed to self-differentiate in growth medium for ~48 h. Cells were subjected to two rounds of infection. Briefly, lentiviral supernatants+8 μg/ml polybrene were added to cultures and the plates were incubated for 15 min at 37° C., then wrapped well with parafilm before centrifuging for 30 min at 1100 g (32° C.). Following centrifugation, the viral supernatants were replaced with growth medium. Cells were maintained in growth medium and harvested 4 d after the last round of infection. For dCas9-KRAB infections, 293T cells were transfected with lentiviral packaging plasmid (pCMV-dR8.91), envelope plasmid (VSV-G), and either dCas9-KRAB expression plasmid (#50919) or sgRNA expression plasmid using the TransIT-LT1 transfection reagent. Lentiviral supernatants were harvested at 11-h intervals from 72-108 h post-transfection. FSHD1 skeletal myoblasts were seeded in collagen-coated 6-well plates and grown to ~80% confluency, then subjected to four serial infections over two days. Cells were allowed to recover for ~8 h in growth medium prior to the next round of infection. Following the last infection, these self-differentiated cultures were maintained in growth medium for 72 h prior to harvesting.

Quantitative Reverse Transcriptase PCR (qRT-PCR).

Total RNAs were extracted using TRIzol (Invitrogen) and purified using the RNeasy Mini kit (Qiagen) after on-column DNase I digestion. Total RNA (2 μg) was used for cDNA synthesis using Superscript III Reverse Transcriptase (Invitrogen), and 200 ng of cDNA were used for qPCR analysis. Oligonucleotide primer sequences are provided in Table 5.

TABLE 5

| Primer Name | Sequence | qPCR/ChIP | SEQ ID NO: |
|---|---|---|---|
| DUX4-fl-F | GCTCTGCTGGAGGAGCTTTAGGA | qPCR | 28 |
| DUX4-fl-R | GCAGGTCTGCWGGTACCTGG | qPCR | 29 |
| Myogenin-F | TCGTGGACAGCATCACAGT | qPCR | 30 |
| Myogenin-R | CTTCCTAGCATCAGGGCAG | qPCR | 31 |
| MyoD-F | GTAGCAGGTGTAACCGTAACC | qPCR | 32 |
| MyoD-R | CAGAGATAAATACAGCCCCAGG | qPCR | 33 |
| Myosin heavy chain 1-F | ACAGAAGCGCAATGTTGAAG | qPCR | 34 |
| Myosin heavy chain 1-R | CACCTTTGCTTGCAGTTTGT | qPCR | 35 |
| FRG1-F | TCTACAGAGACGTAGGCTGTCA | qPCR | 36 |

TABLE 5-continued

| Primer Name | Sequence | qPCR/ChIP | SEQ ID NO: |
|---|---|---|---|
| FRG1-R | CTTGAGCACGAGCTTGGTAG | qPCR | 37 |
| 18S-F | AGTAAGTGCGGGTCATAAGCT | qPCR | 38 |
| 18S-R | CCTCACTAAACCATCCAATCGG | qPCR | 39 |
| SMARCA5-F | TGCGACAGTGTATTCGCAAC | qPCR | 40 |
| SMARCA5-R | GGCTTTGGTCCTCGTTTCTT | qPCR | 41 |
| KDM4C-F | GCTCATTCCAGCACCAATTC | qPCR | 42 |
| KDM4C-R | CCATTCATCCACACCCTCAT | qPCR | 43 |
| BRD2-F | AAACACTCAAGCCATCCACA | qPCR | 44 |
| BRD2-R | GCTTTTCTAATTCCCGCTTTT | qPCR | 45 |
| BAZ1A-F | CACCGAAAGCCGTTTGTGAG | qPCR | 46 |
| BAZ1A-R | TCTACCCGTCACAGCACAAC | qPCR | 47 |
| 4-spec D4Z4-F | TCTGCTGGAGGAGCTTTAG | ChIP | 48 |
| 4-spec D4Z4-R | GAATGGCAGTTCTCCGCG* | ChIP | 49 |
| Myogenin prom-F | CCTATACCCACCAGCTTCTT | ChIP | 50 |
| Myogenin prom-R | GATGTGATTCCCCTTCTTTC | ChIP | 51 |
| 5'D4Z4-flank-F | ATCTGGTTGTGGTAGTGTGC | ChIP | 52 |
| 5'D4Z4-flank-R | TGAGGGTGTCTGAAAGAATG | ChIP | 53 |
| 4p array-F | TGGGAAATACCTGCTACGTG | ChIP | 54 |
| 4p array-R | GTGACGATGACACGTTTGAG | ChIP | 55 |

*G at this position is specific to chromosome 4 (G) vs chromosome 10 (T)

Chromatin Immunoprecipitation (ChIP).

ChIP assays were performed with lentiviral-infected 17Abic differentiated myocytes using the Fast ChIP method (Nelson) with some modifications. Cells were fixed in 1% formaldehyde in DMEM for 10 min and dounced 10× prior to sonication. Cells were sonicated for 12 rounds of 15-sec pulses at 65% power output on a Branson Sonifier 450 (VWR Scientific) to shear the DNA to a ladder of ~200-800 bp, and efficiency of shearing was verified by agarose gel electrophoresis. Chromatin was immunoprecipitated using 2 μg of specific antibodies. SYBR green quantitative PCR assays were performed for 40 cycles of: 94° C. for 15 sec, 55° C. for 30 sec, and 72° C. for 30 sec. PCR products were analyzed on a 1.5% agarose gel to verify correct size of products and specificity of primer annealing. Oligonucleotide primer sequences are provided in Table 5.

Multiple Epigenetic Pathways Regulate Expression of DUX4 fl in FSHD Myocytes.

The D4Z4 macrosatellite array that encodes DUX4 is normally under strong epigenetic repression in adult somatic cells. Generally, FSHD patients exhibit a loss of this repression, displaying DNA hypomethylation at the 4q D4Z4 array and chromatin relaxation (reduced enrichment of the repressive H3K9me3 mark, HP1γ, and cohesin) at the D4Z4 arrays on both 4q and 10q. Thirty-six candidate activators of DUX4 fl were investigated as potential drug targets (Table 3). These candidates include transcriptional regulators, chromatin remodelers, and histone modifying enzymes. For the initial screen, skeletal myocytes from an FSHD1 patient (05Abic) which express consistent and relatively high levels of DUX4 fl when terminally differentiated were used. Using lentivirus-encoded shRNAs, each candidate was knocked down in terminally differentiated cultures, then cells were harvested four days later and assessed for expression of DUX4 fl and other genes.

Figure 11A:
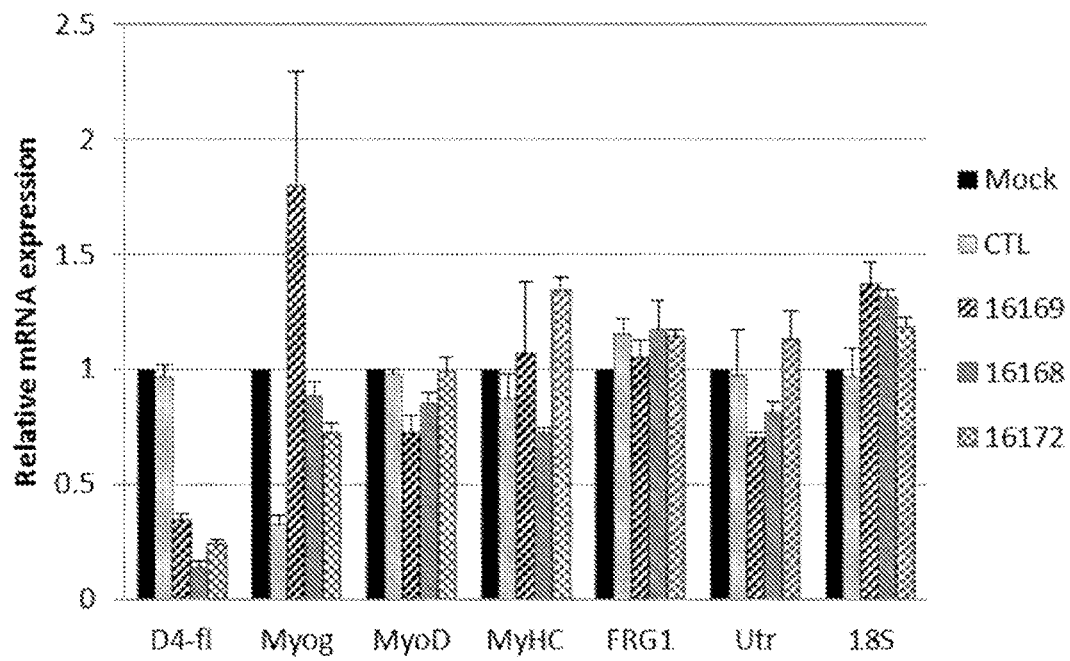
FIGS. 11A-11F show shRNA knockdown of epigenetic regulators reduces expression of DUX4-fl in FSHD myocytes. Differentiated FSHD myocytes were infected in two serial rounds with shRNAs to ASH1L (FIG. 11A), BAZ1A (FIG. 11B), BRD2 (FIG. 11C), KDM4C (FIG. 11D), SMARCA5 (FIG. 11E), or a scrambled control. Four days later, cells were harvested for analysis of the full-length DUX4 isoform (DUX4-fl), Myogenin (Myog), MyoD, Myosin heavy chain 1 (MyHC), FRG1, Utrophin (Utr), and 18S gene expression by qRT-PCR.
Figure 11B:
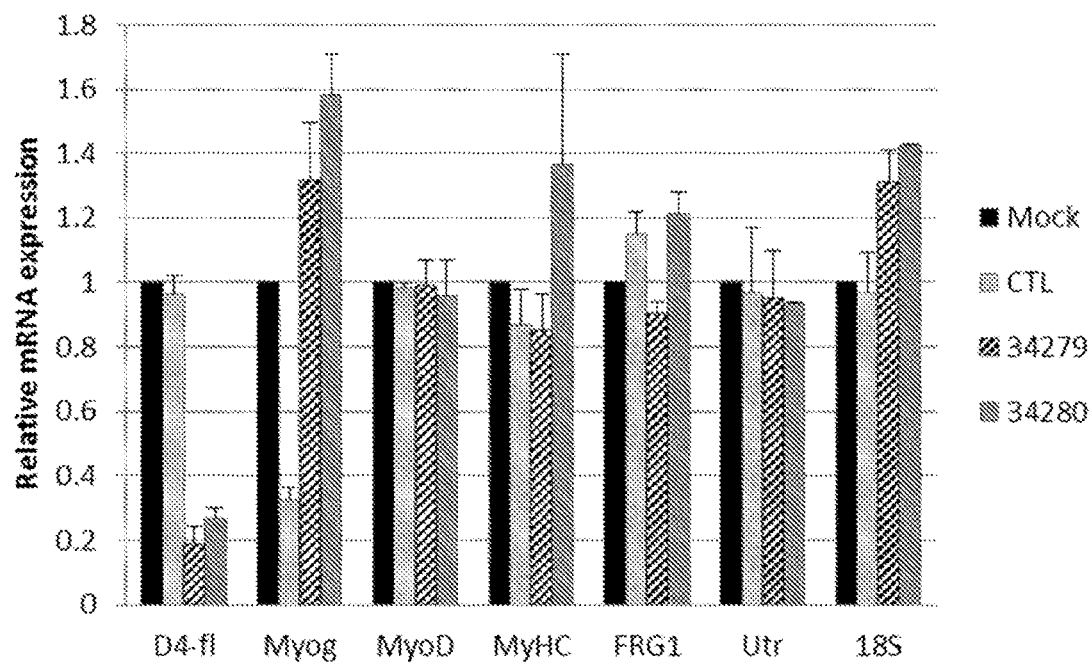
Figure 11C:
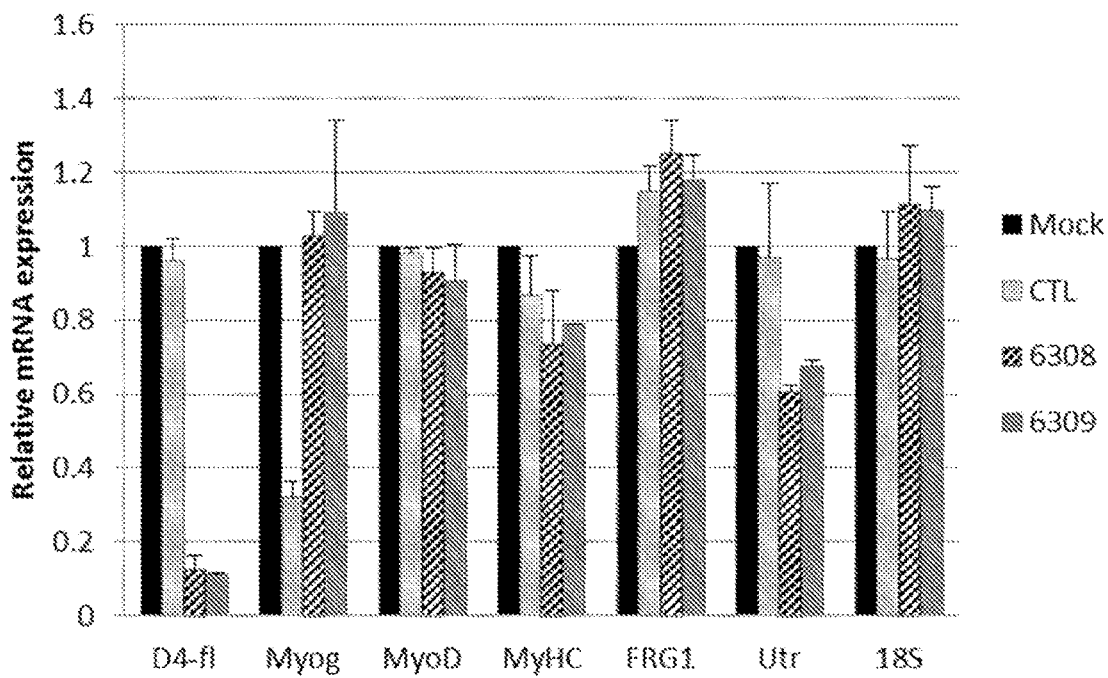
Figure 11D:
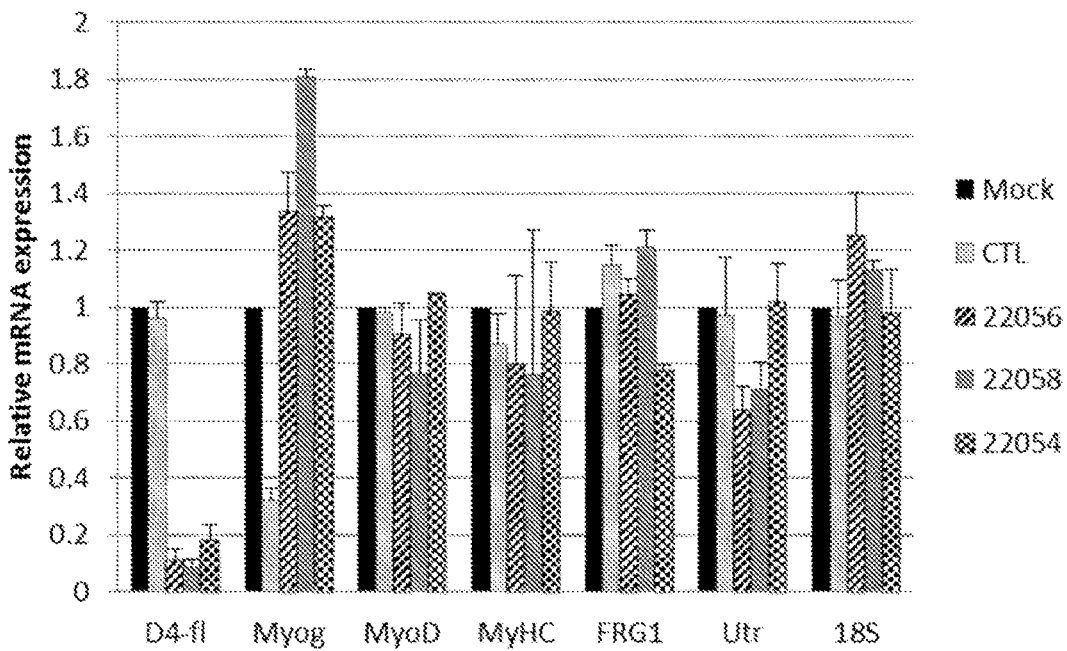
Figure 11E:
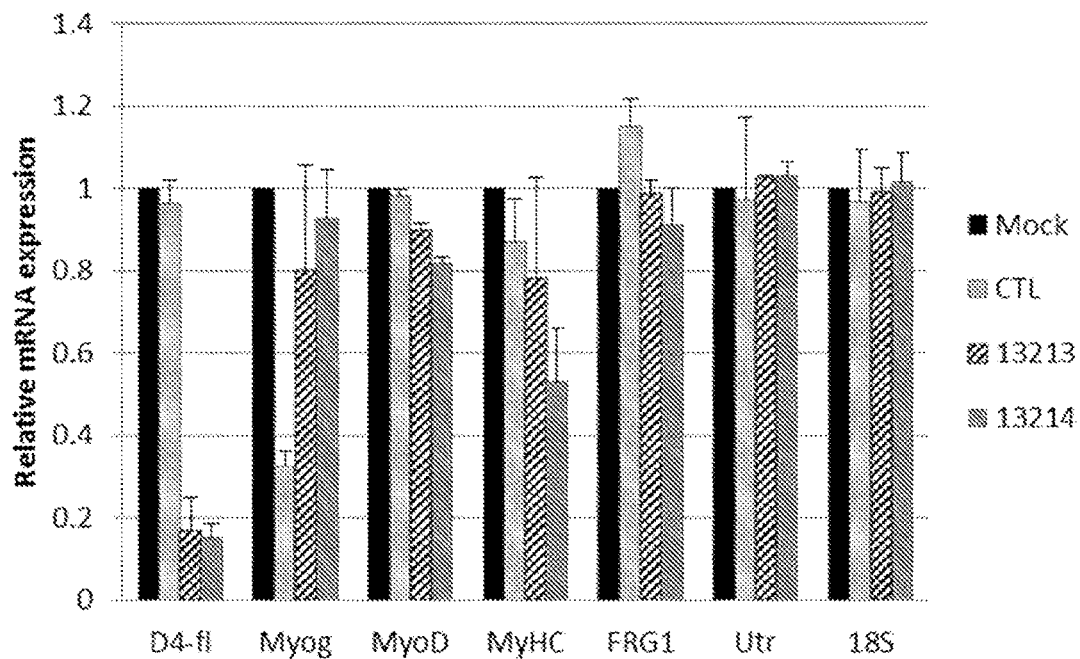

Data indicate that many of these candidates appear to play a role in regulating DUX4 fl expression. For example, ASH1L, the mammalian homologue of the Drosophila Trithorax group protein that counteracts Polycomb-mediated gene silencing, is a histone methyltransferase that is capable of activating DUX4 expression in FSHD. In some embodiments, ASH1L is recruited proximal to the D4Z4 array by the DBE-T lncRNA, resulting in H3K36me2 enrichment and de-repression of the FSHD locus. It was observed that knockdown of ASH1L with three different shRNAs reduced DUX4 fl expression by ~70-80% (FIG. 11A). Likewise, knockdown of the epigenetic reader BRD2 (FIG. 11C), the lysine-specific histone demethylase KDM4C (FIG. 11D), and the chromatin remodeling factors BAZ1A and SMARCA5 substantially reduced levels of DUX4 fl (FIGS. 11B and 11E). Importantly, these knockdowns had minimal effects on expression of the key muscle transcription factors MyoD and Myogenin, or the muscle structural protein Myosin heavy chain 1 (FIGS. 11A-11E). Expression of FRG1, an FSHD candidate gene that lies proximal to the D4Z4 array, was also relatively unchanged (FIGS. 11A-11E). A decrease in expression of Utrophin was also observed following BRD2 knockdown in FSHD myocytes (FIG. 11C).

Figure 11F:
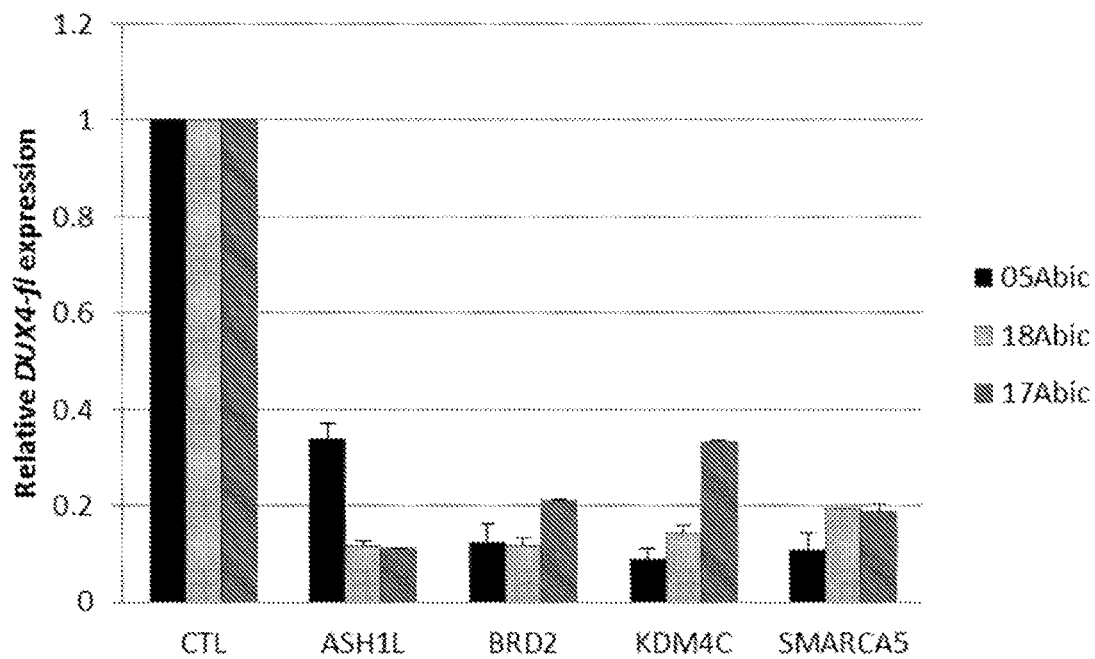
Figure 12A:
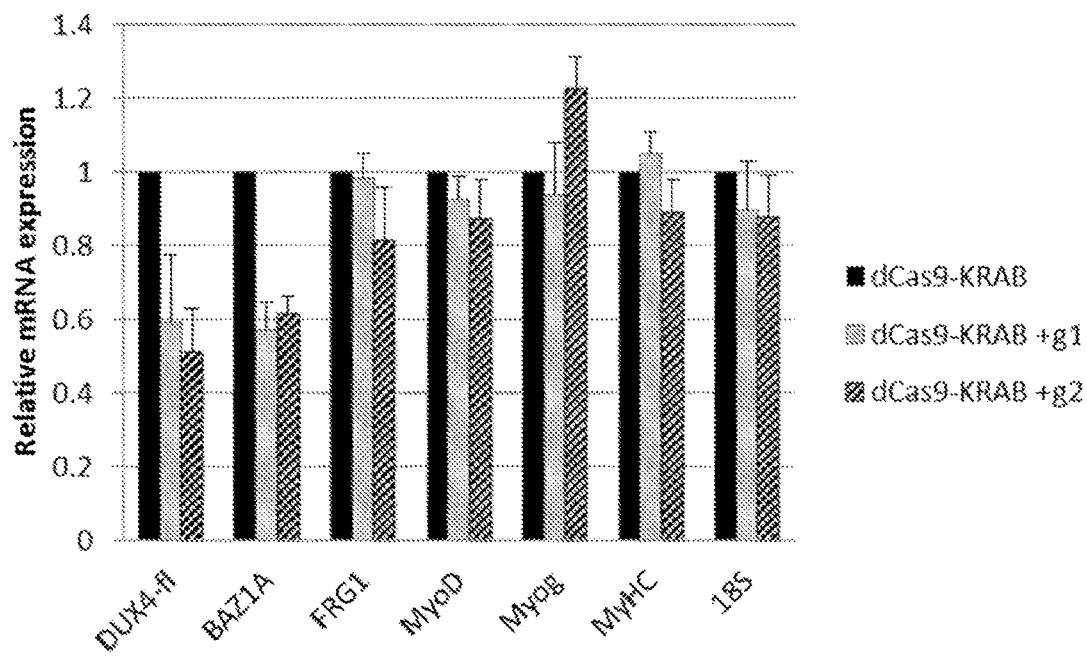
FIGS. 12A-12D show transcriptional repression of epigenetic regulators by dCas9-KRAB reduces expression of DUX4-fl in FSHD myocytes. Differentiated FSHD myocytes were subjected to four serial co-infections with combinations of lentiviral supernatants expressing either dCas9-KRAB or individual sgRNAs (g1-2 for each target gene) targeting BAZ1A (FIG. 12A), BRD2 (FIG. 12B), KDM4C (FIG. 12C), or SMARCA5 (FIG. 12D). Cells were harvested ~72 h later for analysis of gene expression by qRT-PCR (as in FIG. 11A-11F). Data are plotted as the mean+SD value of three independent experiments, with relative mRNA expression for cells infected with dCas9-KRAB alone set to 1.
Figure 12B:
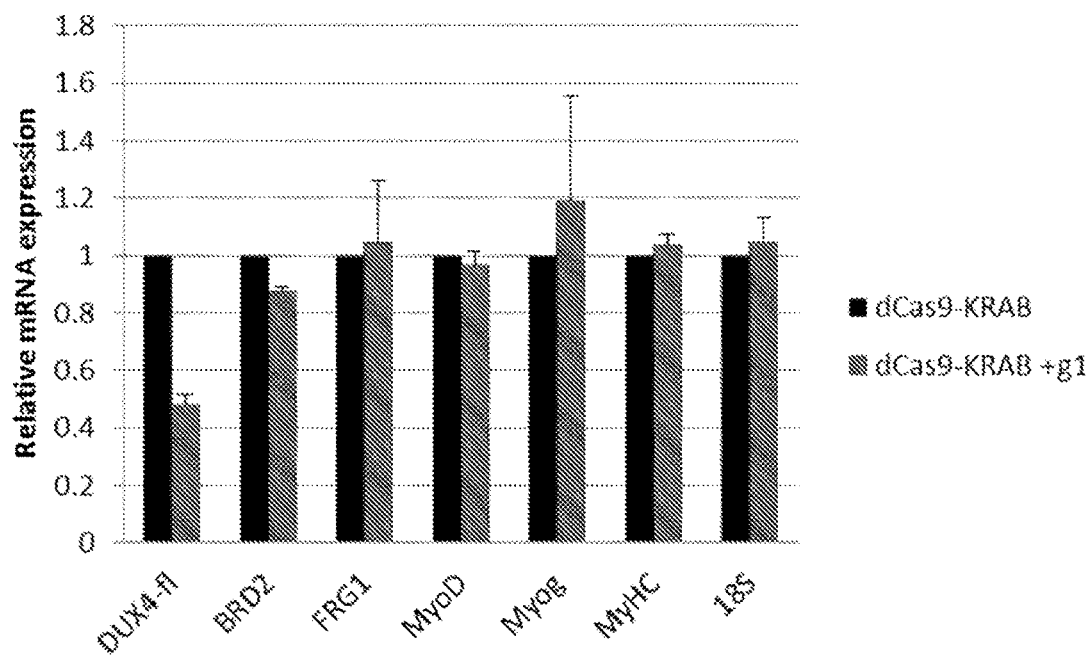
Figure 12C:
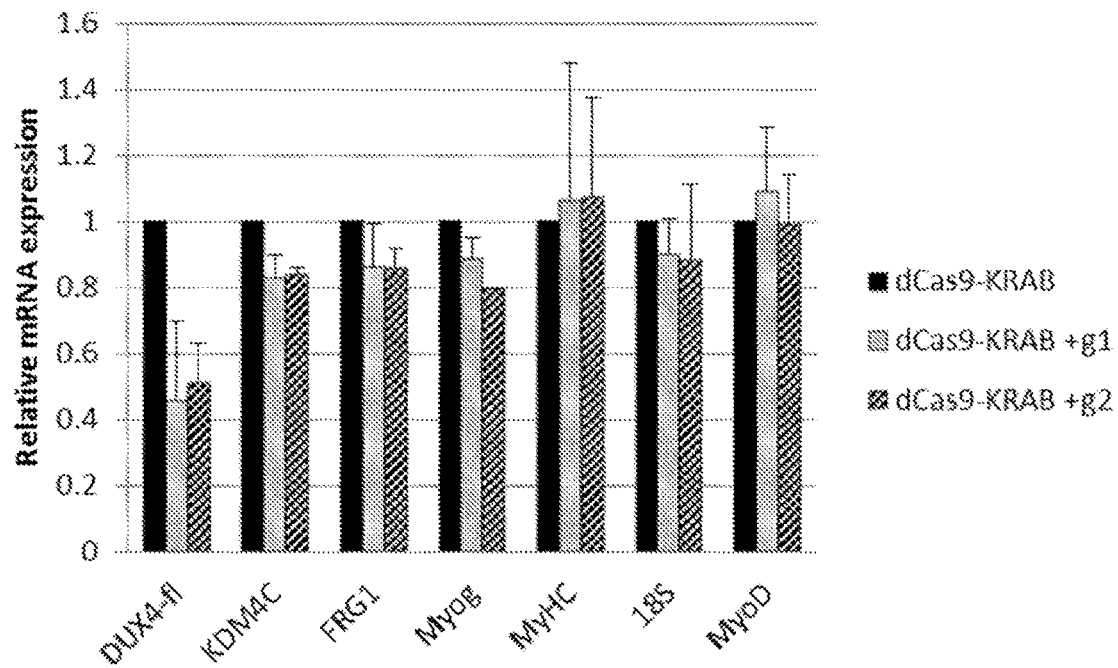
Figure 12D:
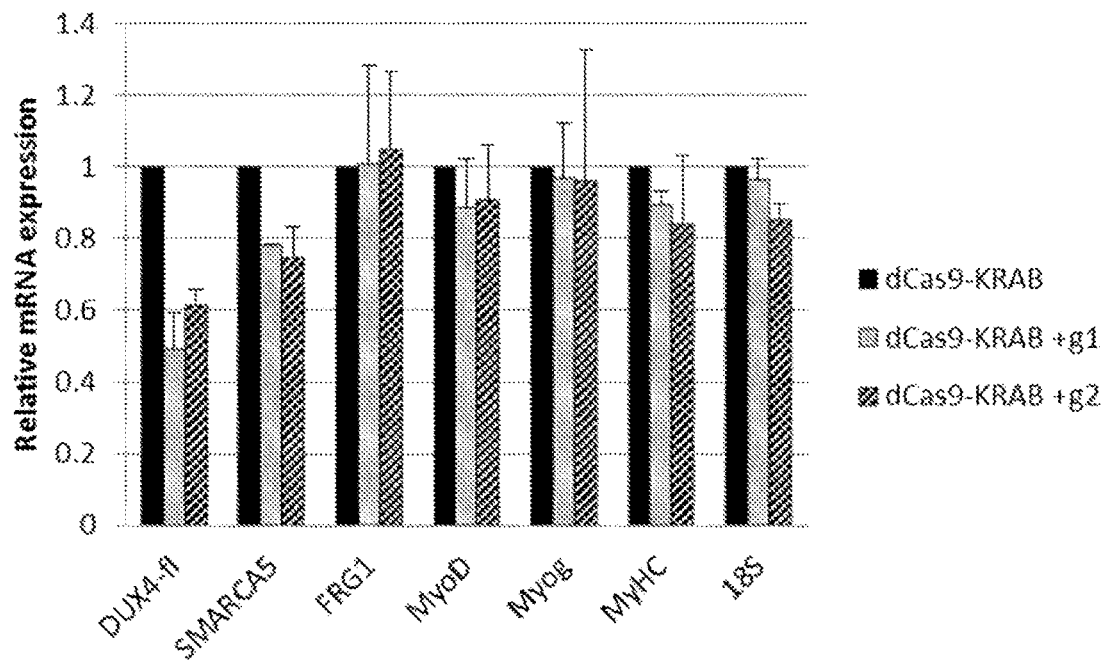
Figure 13A:
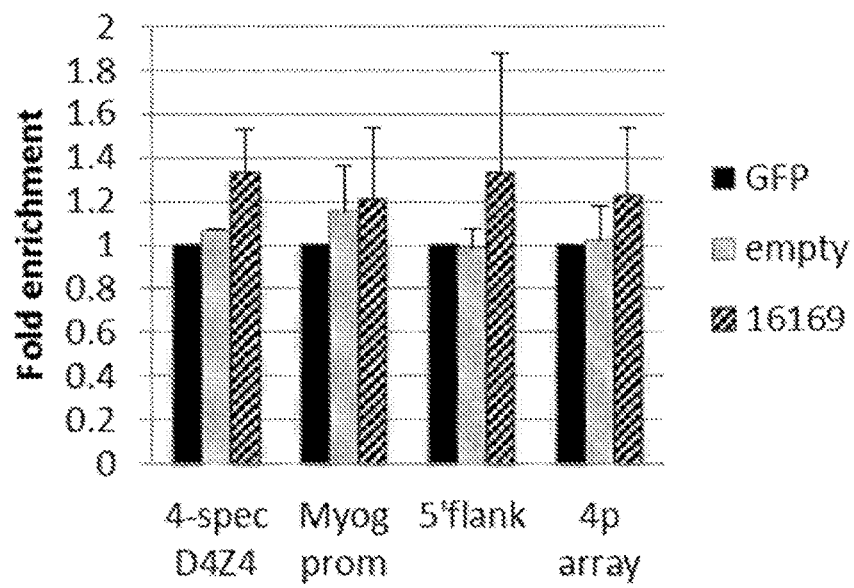
FIGS. 13A-13D show knockdown of candidate regulators increases chromatin repression at the D4Z4 macrosatellite. Differentiated FSHD myocytes were infected in two serial rounds with shRNAs to ASH1L (FIG. 13A), BRD2 (FIG. 13B), KDM4C (FIG. 13C), SMARCA5 (FIG. 13D), a GFP control, or a scrambled control. Four days later, cells were harvested for ChIP analysis. Chromatin was immunoprecipitated using antibodies specific for H3K9me3 or H3 and analyzed by qPCR using primers to the chromosome 4 D4Z4 array (4-spec D4Z4), the Myogenin promoter (Myog prom), a region proximal to D4Z4 (5' flank), and the 4p array on chromosome 4. Data are presented as fold enrichment of the target region by αH3K9me3 normalized to α-histone H3, with enrichment for the GFP shRNA-infected cells set to 1. Data are plotted as the mean+SD value of two independent experiments.
Figure 13B:
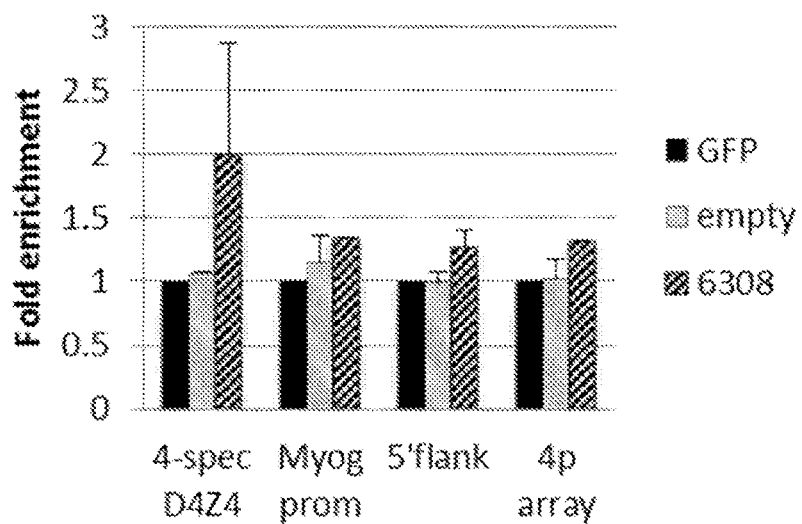
Figure 13C:
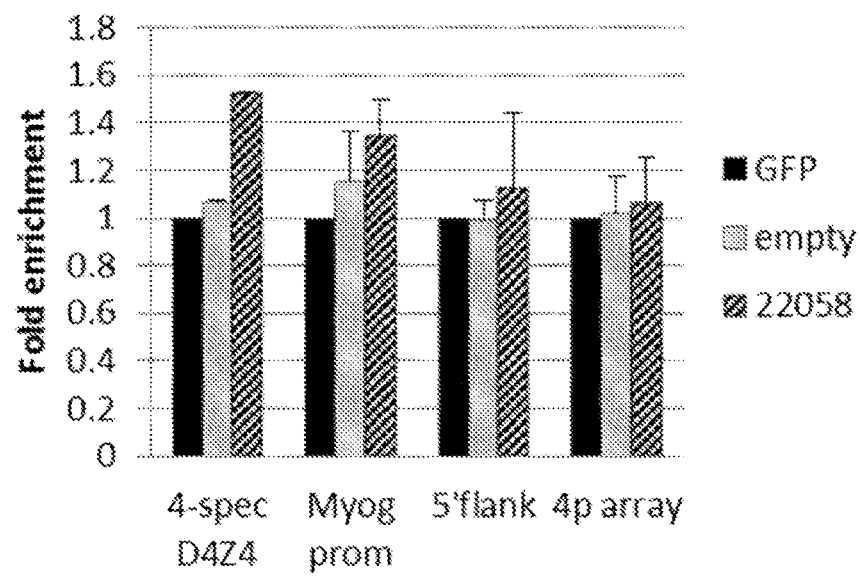
Figure 13D:
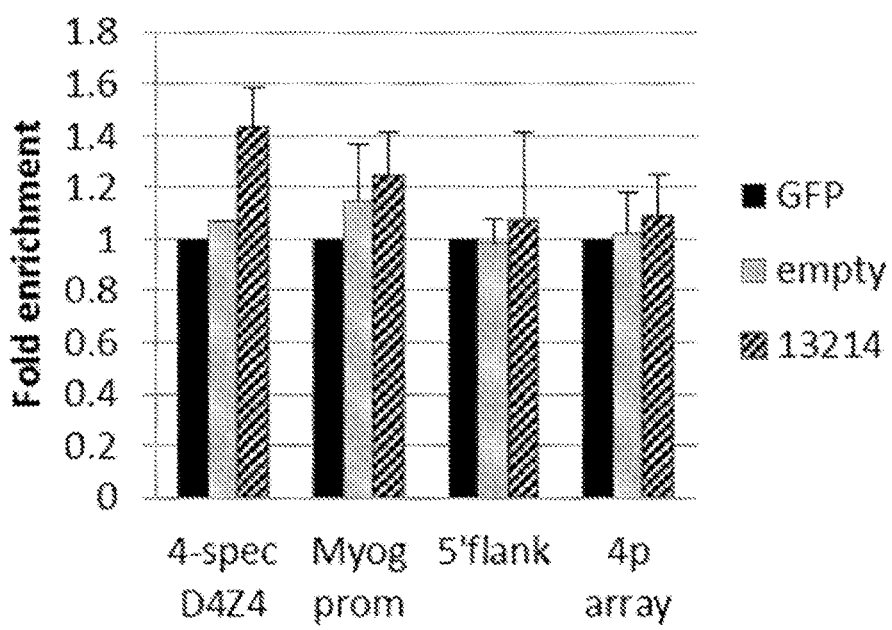

These data indicate that certain epigenetic pathways controlling DUX4-fl expression in FSHD can be modulated without major adverse effects on differentiated myocytes. To confirm candidates across FSHD patient cohorts, shRNA knockdowns of ASH1L, BRD2, KDM4C, and SMARCA5 were tested in myocytes from two other unrelated FSHD1 patients (18Abic and 17Abic), with similar results. Despite variations in viral preps, which are likely responsible for occasions when an shRNA failed to reduce DUX4-fl expression, at least one shRNA for each target substantially reduced levels of DUX4-fl in myocytes from all three patient cohorts (FIG. 11F).

Transcriptional Repression of Candidate Regulators by dCas9-KRAB Reduces DUX4-Fl Expression in FSHD Myocytes.

Knockdown of eight candidates by at least two shRNAs (e.g., two shRNAs per candidate) resulted in >70% reduction of DUX4-fl expression, with minimal effects on other tested genes. Five of the candidates, ASH1L, BAZ1A, BRD2, KDM4C, and SMARCA5, were selected for investigation by a second gene silencing modality. Guided by appropriate sgRNA(s), the enzymatically inactive dCas9 fused to transcriptional effectors (KRAB, LSD1, VP64, p300) can modulate endogenous target gene expression in mammalian cells. When recruited to regions near the transcriptional start site (TSS) of active genes (e.g., −50 to +250 base pairs), dCas9-KRAB can be an effective transcriptional repressor. Thus, for each candidate, 6-8 sgRNAs targeting the promoter or exon 1 were designed. The sgRNAs and dCas9-KRAB were transduced into 17Abic myocytes using four serial co-infections with centrifugation. Cells were harvested 72 h later and assayed for changes in gene expression.

None of the tested sgRNAs targeting ASH1L consistently affected expression of this candidate gene. One functional sgRNA targeting BRD2 (FIG. 12B), and two independently functional sgRNAs for BAZ1A (FIG. 12A), KDM4C (FIG. 12C), and SMARCA5 (FIG. 12D) were identified. As with the shRNA knockdowns, however, even a small reduction of target gene expression proved sufficient to substantially reduce levels of DUX4-fl (by ~30-60%) (FIGS. 12A-12D). By contrast, the expression levels of other genes (FRG1, MyoD, Myogenin, Myosin heavy chain 1, and 18S) were not significantly impacted by reduction of the candidate regulator (FIGS. 12A-12D). DUX4 fl was the only tested gene to be substantially reduced by both methods of repression (shRNA knockdown and CRISPR inhibition).

Knockdown of Candidate Regulators Increases Chromatin Repression at the D4Z4 Macrosatellite.

Changes in chromatin at the pathogenic locus were investigated. Although DUX4 is present in every D4Z4 repeat unit at both 4q and 10q alleles, the chromatin at three of these alleles is already in a compacted, heterochromatic state. Thus, attempts to assess repression at the contracted allele may be dampened by the presence of the other three alleles. To remove 10q alleles from the analysis, a chromosome 4- vs 10-specific sequence polymorphism in the DUX4 exon 2 was accounted for when designing primers.

Chromatin immunoprecipitation (ChIP) was performed for several histone modifications following shRNA knockdown of either ASH1L (FIG. 13A), BRD2 (FIG. 13B), KDM4C (FIG. 13C), or SMARCA5 (FIG. 13D) in 17Abic FSHD myocytes. shRNAs that gave strong, consistent knockdowns of each target gene across all FSHD cohorts tested were assessed. Relative occupancy of the promoter H3K4me3 mark, the active H3K27ac mark, and the repressive H3K9me3 mark were investigated at the chromosome 4 DUX4 exon1/intron1, the region proximal to the D4Z4 array, the heterochromatic 4p macrosatellite array, and the active Myogenin promoter. While knockdown of each epigenetic target had no detectable effect on levels of H3K4me3 or H3K27ac at the D4Z4 locus, levels of the repressive H3K9me3 mark were increased (FIGS. 13A-13D). Levels of enrichment were ~40%-2-fold, and indicate an increase in repression at the distal de-repressed pathogenic repeat among a background of heterochromatic 4q repeats. With regard to this, patient 17A has ~5 repeat units on the contracted 4A161 allele and ~26 repeat units on the non-contracted 4A-L161 allele.

In cells where BRD2, KDM4C, or SMARCA5, was knocked down, enhanced repression appeared to be largely specific to the D4Z4 macrosatellite, as H3K9me3 levels at the other tested regions were not enriched above those seen using control shRNAs (FIGS. 13A-13D). This indicates that knockdown of these DUX4 regulators has very little effect on other genes, including Myogenin.

Figure 14A:
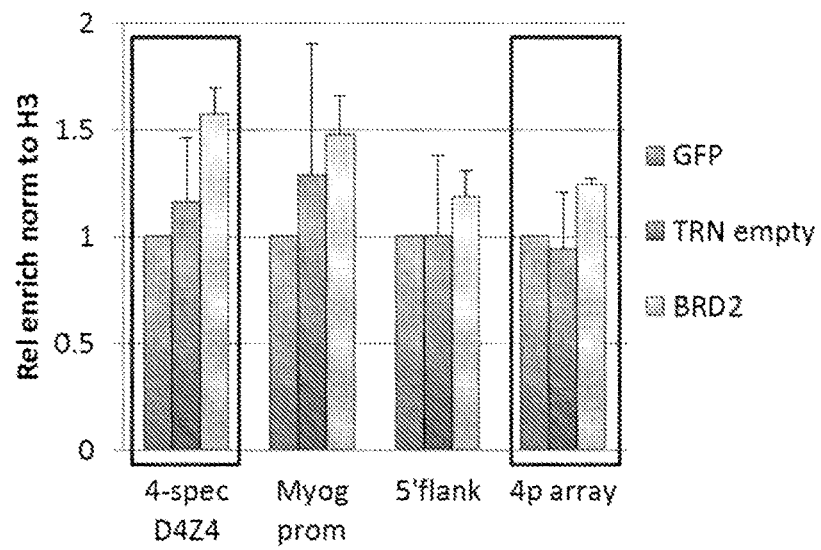
FIGS. 14A-14D show knockdown of candidate regulators increases chromatin repression at the D4Z4 macrosatellite. Differentiated FSHD myocytes were infected in two serial rounds with shRNAs to BRD2 (FIG. 14A), ASH1L (FIG. 14B), SMARCA5 (FIG. 14C), KDM4C (FIG. 14D), a GFP control, or a scrambled control. Four days later, cells were harvested for ChIP analysis. Chromatin was immunoprecipitated using antibodies specific for H3K36me3 and analyzed by qPCR using primers to the chromosome 4 D4Z4 array (4-spec D4Z4), the Myogenin promoter (Myog prom), a region proximal to D4Z4 (5' flank), and the 4p array on chromosome 4. Data are presented as fold enrichment of the target region by αH3K9me3 normalized to α-histone H3, with enrichment for the GFP shRNA-infected cells set to 1.
Figure 14B:
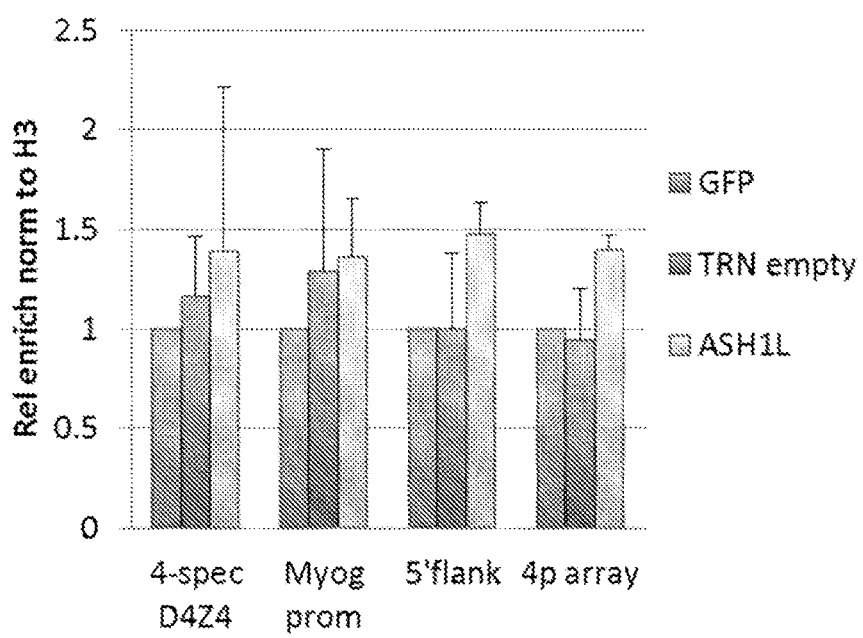
Figure 14C:
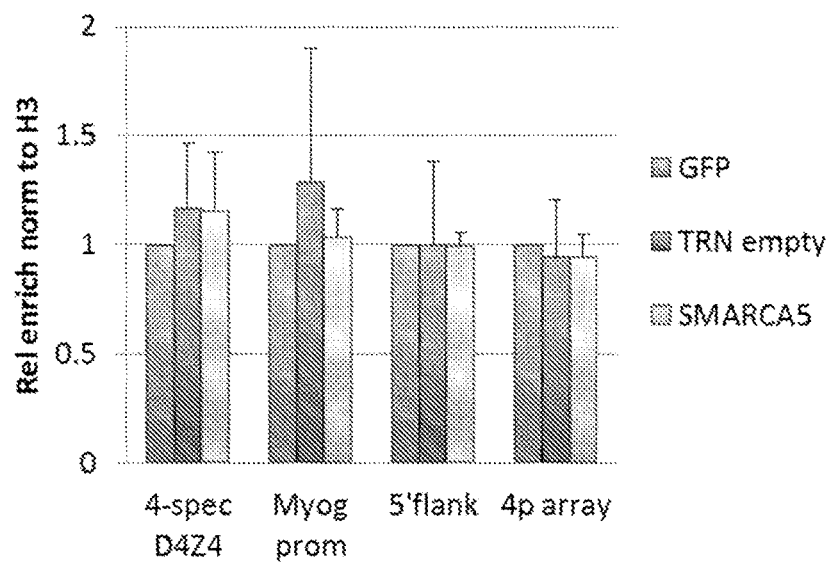
Figure 14D:
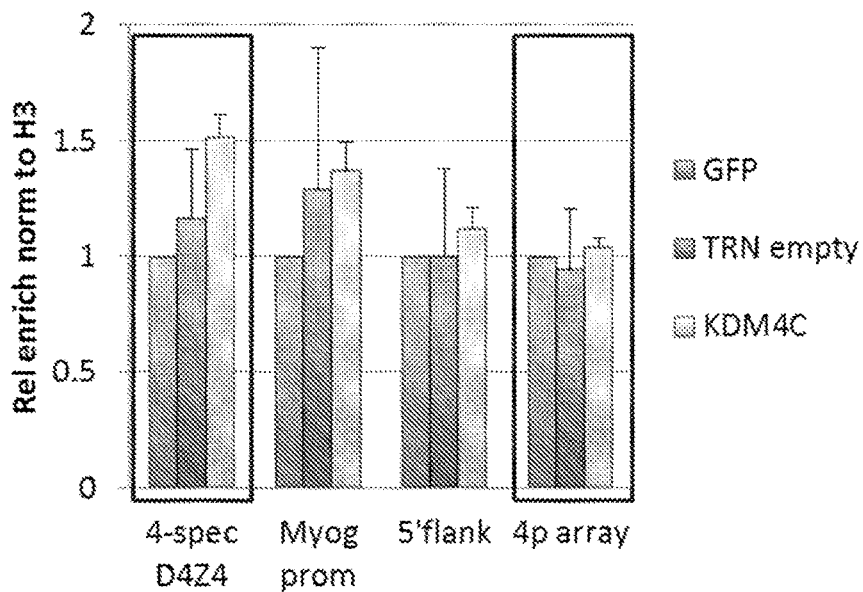

Relative occupancy of H3K36me3 at 4-specific D4Z4 (e.g., chromosome 4 vs 10 specific polymorphism at 3' end of R primer), D4Z4 5' flank (upstream of array), Myogenin promoter (active, muscle-specific gene promoter), and 4p array (another heterochromatic array on ch 4) was also assessed after knockdown of BRD2 (FIG. 14A), ASH1L (FIG. 14B), SMARCA5 (FIG. 14C), and KDM4C (FIG. 14D). Data indicate a significant enrichment at 4-specific D4Z4 in BRD2 and KDMC4 knockdown cells (FIGS. 14A and 14D). Enrichment at the Myogenin promoter was not significant compared to empty vector controls, and there was little to no enrichment at the heterochromatic 4p array.

In summary, data described in this example indicate that independent knockdown of multiple chromatin regulators results in chromatin repression at D4Z4 and a substantial decrease in DUX4 fl expression in FSHD myocytes, and that modest inhibition of certain epigenetic pathways can substantially reduce levels of DUX4-fl, demonstrating their potential as novel drug targets for FSHD.

Example 4

This example describes that small molecules targeting epigenetic factors can modulate DUX4 expression. Trichostatin A (TSA) is a histone deacetylase inhibitor, 5-aza-2'-deoxycytidine (5'ADC) is a DNA methylation inhibitor and chaetocin (CH) is a histone methyltransferase inhibitor. Treatment of primary myoblasts isolated from FSHD1-affected (e.g., Cohort 28A, 29A, 30A, and 15A) and FSHD-asymptomatic (e.g., Cohort 28B, 29B, 30B, and 15B) patients with small molecules alone, or in combination, that affect the epigenetic state of the D4Z4 repeat affect DUX4 expression (FIG. 15).

Small Molecules that Affect DUX4 Expression by Altering Myogenic Differentiation are Acting Indirectly and are not Viable Candidates for FSHD.

JQ1 is a small molecule epigenetic drug that appears to inhibit DUX4 expression and downstream genes TRIM43 and ZSCAN4 in primary FSHD muscle cells (09Abic). However, a time course of treatment shows that JQ1 regulation of DUX4 is indirect and achieved by inhibiting the expression of several key myogenic regulatory genes myogenin (Myog), myoD, myosin heavy chain (MyHC), and myostatin (Myost) (FIG. 16). DUX4 expression is induced during myogenic differentiation, and blocking or slowing down this process, as the case with JQ1, give the appearance of inhibiting DUX4 expression, when in fact it is merely altering the kinetics of myoginc differentiation. Importantly, these genes are misregulated by JQ1 in both FSHD and healthy human skeletal muscle myoblasts (HSMM) (FIG. 17). Therefore, JQ1 is an example of a non-specific small molecule and not appropriate for use as an FSHD therapeutic.

Example 5

This example describes modulation of ZSCAN4 expression by knockdown of DUX-4, SMARCA5, and KDM4C. ZSCAN4 plays a role in telomere maintenance and regulation of embryonic stem cell pluripotency. Briefly, FSHD skeletal muscle myotubes were treated with antisense oligonucleotides that target DUX-4, SMARCA5, or KDM4C and the relative expression of the indicated gene was determined using RT-PCR.

The following materials were used in Example 5. Cells included: FTCE-00016-01 (immortalized FSDH myoblast line, 6.3 repeats), isogenic lines A4 control healthy normal, and C12 FSHD myoblasts.

Media components and tissue culture materials included: Skeletal Muscle Growth Medium (PromoCell, C-23160) supplemented with 15% FBS (Hyclone, SH30071) and Pen/Strep (Gibco, 15140148). Skeletal Muscle Cell Differentiation Medium (PromoCell, C-23061) supplemented with 20% KnockOut Serum Replacement (Gibco, 10828010) and Pen/Strep (Differentiation media). EmbryoMax 0.1% Gelatin Solution (EMDmillipore ES-006-B). PBS (Gibco, 10010023), Tissue culture treated 96-well microplate (Corning, CLS3595), TC-Treated Multiwell Cell Culture Plat (Falcon, 353046).

Real Time PCR reagents included: Lysis buffer-Roche Realtime Ready lysis buffer 19.5 uL. (for 20 uL) (Roche, 07248431001), DNAse I (Ambion, AM2222) 0.25 uL, Protector RNase Inhibitor (Roche, 3335402001) 0.25 uL. RNeasy Micro Kit (Qiagen, 74004), Taqman Preamp Master Mix (ThermoFisher Scientific, 4391128), Taqman Multiplex Master Mix (ThermoFisher Scientific, 4484262), ZSCAN4 Taqman Assay (ThermoFisher Scientific, Hs00537549_m1, FAM-MGB), MYOG Taqman Assay (ThermoFisher Scientific, Hs01072232_m1, JUN-QSY), RPLP0 Taqman Assay (ThermoFisher Scientific, Hs99999902_m1), LEUTX Taqman Assay (ThermoFisher Scientific, Hs00418470_m1).

Antisense oligonucleotide sequences are shown in Table 5.

TABLE 6

| Gene | SEQ ID NO: | Antisense Oligonucleotides |
|---|---|---|
| KDM4C | 24 | ATGCTTCGTGATGACC |
| SMARCA5 | 25 | ATCAGCCTTAATTCGA |
| DUX-4 | 26 | CAGCGTCGGAAGGTGG |
| Non-targeting | 27 | AACACGTCTATACGC |

FIG. 11 shows that ZSCAN4 expression in FSHD skeletal muscle myotubes was reduced by knockdown of DUX-4 using antisense oligonucleotides. DMSO treated FSHD skeletal muscle myotubes and wild type myotubes were used as controls.

FIG. 12 shows that ZSCAN4 expression in FSHD skeletal muscle myotubes was reduced by knockdown of SMARCA5 and KDM4C. Non-targeting antisense oligonucleotides were used as a control.

Taken together, these results demonstrated that the inhibition or knock-down of DUX-4, SMARCA5, or KDM4C can reduce expression of ZSCAN4.

SEQUENCES

SaCas9 Protein (SEQ ID NO: 20)
MAPKKKRKVGIHGVPAAKRNYILGLDIGITSVGYGIIDYETRDVIDAGVRLFKEANVEN
NEGRRSKRGARRLKRRRRHRIQRVKKLLFDYNLLTDHSELSGINPYEARVKGLSQKLSE
EEFSAALLHLAKRRGVHNVNEVEEDTGNELSTKEQISRNSKALEEKYVAELQLERLKK
DGEVRGSINRFKTSDYVKEAKQLLKVQKAYHQLDQSFIDTYIDLLETRRTYYEGPGEGS
PFWKDIKEWYEMLMGHCTYFPEELRSVKYAYNADLYNALNDLNNLVITRDENEKLE
YYEKFQIIENVFKQKKKPTLKQIAKEILVNEEDIKGYRVTSTGKPEFTNLKVYHDIKDITA
RKEIIENAELLDQIAKILTIYQSSEDIQEELTNLNSELTQEEIEQISNLKGYTGTHNLSLKAI
NLILDELWHTNDNQIAIFNRLKLVPKKVDLSQQKEIPTTLVDDFILSPVVKRSFIQSIKVIN
AIIKKYGLPNDIIIELAREKNSKDAQKMINEMQKRNRQTNERIEEIIRTTGKENAKYLIEKI
KLHDMQEGKCLYSLEAIPLEDLLNNPFNYEVDHIIPRSVSFDNSFNNKVLVKQEENSKK
GNRTPFQYLSSSDSKISYETFKKHILNLAKGKGRISKTKKEYLLEERDINRFSVQKDFINR
NLVDTRYATRGLMNLLRSYFRVNNLDVKVKSINGGFTSFLRRKWKFKKERNKGYKHH
AEDALIIANADFIFKEWKKLDKAKKVMENQMFEEKQAESMPEIETEQEYKEIFITPHQIK
HIKDFKDYKYSHRVDKKPNRELINDTLYSTRKDDKGNTLIVNNLNGLYDKDNDKLKKL
INKSPEKLLMYHHDPQTYQKLKLIMEQYGDEKNPLYKYYEETGNYLTKYSKKDNGPVI
KKIKYYGNKLNAHLDITDDYPNSRNKVVKLSLKPYRFDVYLDNGVYKFVTVKNLDVIK
KENYYEVNSKCYEEAKKLKKISNQAEFIASFYNNDLIKINGELYRVIGVNNDLLNRIEVN
MIDITYREYLENMNDKRPPRIIKTIASKTQSIKKYSTDILGNLYEVKSKKHPQIIKKGKRP
AATKKAGQAK Sa-dCas9-KRAB (SEQ ID NO: 21)
MAPKKKRKVGIHGVPAAKRNYILGLAIGITSVGYGIIDYETRDVIDAGVRLFKEANVEN
NEGRRSKRGARRLKRRRRHRIQRVKKLLFDYNLLTDHSELSGINPYEARVKGLSQKLSE
EEFSAALLHLAKRRGVHNVNEVEEDTGNELSTKEQISRNSKALEEKYVAELQLERLKK
DGEVRGSINRFKTSDYVKEAKQLLKVQKAYHQLDQSFIDTYIDLLETRRTYYEGPGEGS
PFGWKDIKEWYEMLMGHCTYFPEELRSVKYAYNADLYNALNDLNNLVITRDENEKLE
YYEKFQIIENVFKQKKKPTLKQIAKEILVNEEDIKGYRVTSTGKPEFTNLKVYHDIKDITA
RKEIIENAELLDQIAKILTIYQSSEDIQEELTNLNSELTQEEIEQISNLKGYTGTHNLSLKAI
NLILDELWHTNDNQIAIFNRLKLVPKKVDLSQQKEIPTTLVDDFILSPVVKRSFIQSIKVIN
AIIKKYGLPNDIIIELAREKNSKDAQKMINEMQKRNRQTNERIEEIIRTTGKENAKYLIEKI
KLHDMQEGKCLYSLEAIPLEDLLNNPFNYEVDHIIPRSVSFDNSFNNKVLVKQEEASKK
GNRTPFQYLSSSDSKISYETFKKHILNLAKGKGRISKTKKEYLLEERDINRFSVQKDFINR
NLVDTRYATRGLMNLLRSYFRVNNLDVKVKSINGGFTSFLRRKWKFKKERNKGYKHH
AEDALIIANADFIFKEWKKLDKAKKVMENQMFEEKQAESMPEIETEQEYKEIFITPHQIK
HIKDFKDYKYSHRVDKKPNRELINDTLYSTRKDDKGNTLIVNNLNGLYDKDNDKLKKL
INKSPEKLLMYHHDPQTYQKLKLIMEQYGDEKNPLYKYYEETGNYLTKYSKKDNGPVI
KKIKYYGNKLNAHLDITDDYPNSRNKVVKLSLKPYRFDVYLDNGVYKFVTVKNLDVIK
KENYYEVNSKCYEEAKKLKKISNQAEFIASFYNNDLIKINGELYRVIGVNNDLLNRIEVN
MIDITYREYLENMNDKRPPRIIKTIASKTQSIKKYSTDILGNLYEVKSKKHPQIIKKGKRP
AATKKAGQAKKKKGSDAKSLTAWSRTLVTFKDVFVDFTREEWKLLDTAQQIVYRNV
MLENYKNLVSLGYQLTKPDVILRLEKGEEP Sp-dCas9-KRAB (SEQ ID NO: 22)
MDKKYSIGLAIGTNSVGWAVITDEYKVPSKKFKVLGNTDRHSIKKNLIGALLFDSGETA
EATRLKRTARRRYTRRKNRICYLQEIFSNEMAKVDDSFFHRLEESFLVEEDKKHERHPIF
GNIVDEVAYHEKYPTIYHLRKKLVDSTDKADLRLIYLALAHMIKFRGHFLIEGDLNPDN
SDVDKLFIQLVQTYNQLFEENPINASGVDAKAILSARLSKSRRLENLIAQLPGEKKNGLF
GNLIALSLGLTPNFKSNFDLAEDAKLQLSKDTYDDDLDNLLAQIGDQYADLFLAAKNLS
DAILLSDILRVNTEITKAPLSASMIKRYDEHHQDLTLLKALVRQQLPEKYKEIFFDQSKN
GYAGYIDGGASQEEFYKFIKPILEKMDGTEELLVKLNREDLLRKQRTFDNGSIPHQIHLG
ELHAILRRQEDFYPFLKDNREKIEKILTFRIPYYVGPLARGNSRFAWMTRKSEETITPWN
FEEVVDKGASAQSFIERMTNFDKNLPNEKVLPKHSLLYEYFTVYNELTKVKYVTEGMR
KPAFLSGEQKKAIVDLLFKTNRKVTVKQLKEDYFKKIECFDSVETSGVEDRFNASLGTY
HDLLKIIKDKDFLDNEENEDILEDIVLTLTLFEDREMIEERLKTYAHLFDDKVMKQLKRR
RYTGWGRLSRKLINGIRDKQSGKTILDFLKSDGFANRNFMQLIHDDSLTFKEDIQKAQV
SGQGDSLHEHIANLAGSPAIKKGILQTVKVVDELVKVMGRHKPENIVIEMARENQTTQK
GQKNSRERMKRIEEGIKELGSQILKEHPVENTQLQNEKLYLYYLQNGRDMYVDQELDI

SEQUENCES

NRLSDYDVDAIVPQSFLKDDSIDNKVLTRSDKNRGKSDNVPSEEVVKKMKNYWRQLL
NAKLITQRKFDNLTKAERGGLSELDKAGFIKRQLVETRQITKHVAQILDSRMNTKYDEN
DKLIREVKVITLKSKLVSDFRKDFQFYKVREINNYHHAHDAYLNAVVGTALIKKYPKLE
SEFVYGDYKVYDVRKMIAKSEQEIGKATAKYFFYSNIMNFFKTEITLANGEIRKRPLIET
NGETGEIVWDKGRDFATVRKVLSMPQVNIVKKTEVQTGGFSKESILPKRNSDKLIARKK
DWDPKKYGGFDSPTVAYSVLVVAKVEKGKSKKLKSVKELLGITIMERSSFEKNPIDFLE
AKGYKEVKKDLIIKLPKYSLFELENGRKRMLASAGELQKGNELALPSKYVNFLYLASH
YEKLKGSPEDNEQKQLFVEQHKHYLDEIIEQISEFSKRVILADANLDKVLSAYNKHRDK
PIREQAENIIHLFTLTNLGAPAAFKYFDTTIDRKRYTSTKEVLDATLIHQSITGLYETRIDL
SQLGGDGTGGPKKKRKVYPYDVPDYAGYPYDVPDYAGSYPYDVPDYAGSMDAKSLT
AWSRTLVTFKDVFVDFTREEWKLLDTAQQIVYRNVMLENYKNLVSLGYQLTKPDVILR
LEKGEEP

Sa-dCas9 (SEQ ID NO: 23)
MAPKKKRKVGIHGVPAAKRNYILGLAIGITSVGYGIIDYETRDVIDAGVRLFKEANVEN
NEGRRSKRGARRLKRRRRHRIQRVKKLLFDYNLLTDHSELSGINPYEARVKGLSQKLSE
EEFSAALLHLAKRRGVHNVEVEEDTGNELSTKEQISRNSKALEEKYVAELQLERLKK
DGEVRGSINRFKTSDYVKEAKQLLKVQKAYHQLDQSFIDTYIDLLETRRTYYEGPGEGS
PFGWKDIKEWYEMLMGHCTYFPEELRSVKYAYNADLYNALNDLNNLVITRDENKLE
YYEKFQIIENVFKQKKKPTLKQIAKEILVNEEDIKGYRVTSGKPEFTNLKVYHDIKDITA
RKEIIENAELLDQIAKILTIYQSSEDIQEELTNLNSELTQEEIEQISNLKGYTGTHNLSLKAI
NLILDELWHTNDNQIAIFNRLKLVPKKVDLSQQKEIPTTLVDDFILSPVVKRSFIQSIKVIN
AIIKKYGLPNDIIIELAREKNSKDAQKMINEMQKRNRQTNERIEEIIRTTGKENAKYLIEKI
KLHDMQEGKCLYSLEAIPLEDLLNNPFNYEVDHIIPRSVSFDNSFNNKVLVKQEEASKK
GNRTPFQYLSSSDSKISYETFKKHILNLAKGKGRISKTKKEYLLEERDINRFSVQKDFINR
NLVDTRYATRGLMNLLRSYFRVNNLDVKVKSINGGFTSFLRRKWKFKKERNKGYKHH
AEDALIIANADFIFKEWKKLDKAKKVMENQMFEEKQAESMPEIETEQEYKEIFITPHQIK
HIKDFKDYKYSHRVDKKPNRELINDTLYSTRKDDKGNTLIVNNLNGLYDKDNDKLKKL
INKSPEKLLMYHHDPQTYQKLKLIMEQYGDEKNPLYKYYEETGNYLTKYSKKDNGPVI
KKIKYYGNKLNAHLDITDDYPNSRNKVVKLSLKPYRFDVYLDNGVYKFVTVKNLDVIK
KENYYEVNSKCYEEAKKLKKISNQAEFIASFYNNDLIKINGELYRVIGVNNDLLNRIEVN
MIDITYREYLENMNDKRPPRIIKTIASKTQSIKKYSTDILGNLYEVKSKKHPQIIKKG

What is claimed is:

1. A method for ameliorating facioscapulohumeral muscular dystrophy (FSHD) in a subject, the method comprising administering to the subject an epigenetic modulator of DUX4 gene expression, wherein the epigenetic modulator reduces DUX4 gene expression in the muscle cells of the subject, and wherein the epigenetic modulator of DUX 4 is a nucleic acid that is a direct inhibitor of CARM1, and wherein the nucleic acid is an interfering nucleic acid selected from the group consisting of double stranded RNA (dsRNA), siRNA, shRNA, and antisense oligonucleotide (ASO).

2. The method of claim 1, wherein the muscle cell is a terminally differentiated muscle cell.

3. The method of claim 1, wherein the subject is identified as having FSHD based upon the presence of a transcriptionally active DUX4 gene.

4. The method of claim 1, further comprising assessing the DUX4 expression level of the subject before and/or after the administering, wherein a change in the DUX4 expression level indicates effectiveness of ameliorating FSHD.

5. The method of claim 1, wherein the nucleic acid is an shRNA.

6. The method of claim 1, wherein the nucleic acid is expressed from a viral vector.

7. The method of claim 6, wherein the viral vector is a lentiviral vector.

8. The method of claim 6, wherein the viral vector comprises a promoter operably linked to the nucleotide sequence encoding the inhibitory nucleic acid.

* * * * *